(12) United States Patent
Boyd et al.

(10) Patent No.: US 9,642,658 B2
(45) Date of Patent: May 9, 2017

(54) DEVICE AND METHOD FOR DELIVERY OF THERAPEUTIC AGENTS VIA INTERNAL IMPLANTS

(75) Inventors: Lawrence M. Boyd, Durham, NC (US); Samuel B. Adams, Jr., Durham, NC (US); Matthew R. Penny, Clayton, NC (US); Cody Blazek, High Point, NC (US)

(73) Assignee: OrthoClip LLC, Research Triangle Park, NC (US)

( * ) Notice: Subject to any disclaimer, the term of this patent is extended or adjusted under 35 U.S.C. 154(b) by 403 days.

(21) Appl. No.: 12/908,464

(22) Filed: Oct. 20, 2010

(65) Prior Publication Data

US 2011/0178465 A1    Jul. 21, 2011

Related U.S. Application Data

(63) Continuation-in-part of application No. 12/580,190, filed on Oct. 15, 2009.
(Continued)

(51) Int. Cl.
*A61B 17/80* (2006.01)
*A61B 17/60* (2006.01)
(Continued)

(52) U.S. Cl.
CPC .............. *A61B 17/80* (2013.01); *A61B 17/60* (2013.01); *A61B 17/7061* (2013.01);
(Continued)

(58) Field of Classification Search
CPC ..... A61B 17/80; A61B 17/60; A61B 17/7061; A61B 17/8028; A61B 2017/561;
(Continued)

(56) References Cited

U.S. PATENT DOCUMENTS 2,257,709 A * 9/1941 Anderson .............. A61C 17/00
                                                                128/861
4,297,993 A    11/1981 Harle
(Continued)

FOREIGN PATENT DOCUMENTS

DE    3729253 A1    3/1989
EP    236468 B1    7/1991
(Continued)

OTHER PUBLICATIONS

Montali, Antibacterial coating systems, Injury International Journal of the Care of the Injured, May 2006, vol. 37, Issue 2, Supplement.
(Continued)

*Primary Examiner* — Imani Hayman
*Assistant Examiner* — Laura Schell
(74) *Attorney, Agent, or Firm* — Michael G. Johnston; Moore & Van Allen PLLC

(57) ABSTRACT

A device is provided for use with a medical implant for delivering an agent to a designated site of action in a body of a patient. The agent-delivery device comprises a body member having an inner surface and a projection on the inner surface of the body member. An agent-delivery medium is associated with the body member. The agent-delivery medium includes a therapeutic agent for treating the body of the patient. The body member is adapted to be secured to the medical implant such that the projection operatively engages the medical implant for spacing the inner surface of the body member from the implant, and the agent-delivery medium is configured to release the therapeutic agent after implantation in the body of the patient. In alternative embodiments, the agent-delivery device comprises a first body member having an inner surface and a second body member having an inner surface. When connected, the inner surfaces of the first body member and the
(Continued)

second body member define a cavity adapted to receive the medical implant. The body member may also define an opening therethrough, the opening configured to receive an anchor member for fixing the body member in a body of a patient.

9 Claims, 46 Drawing Sheets

Related U.S. Application Data

(60) Provisional application No. 61/105,659, filed on Oct. 15, 2008.

(51) Int. Cl.
| | | |
|---|---|---|
| *A61B 17/70* | (2006.01) | |
| *A61F 2/30* | (2006.01) | |
| *A61K 9/00* | (2006.01) | |
| *A61K 9/06* | (2006.01) | |

(52) U.S. Cl.
CPC ............ *A61F 2002/3068* (2013.01); *A61F 2002/30677* (2013.01); *A61F 2250/0068* (2013.01); *A61K 9/0024* (2013.01); *A61K 9/06* (2013.01)

(58) Field of Classification Search
CPC ............ A61M 31/002; A61M 2205/04; A61M 2210/02; A61F 2002/30677; A61F 2002/30678; A61F 2002/3068
USPC ............................................ 604/890.1, 891.1
See application file for complete search history.

(56) References Cited

U.S. PATENT DOCUMENTS

| | | |
|---|---|---|
| 4,365,356 A | 12/1982 | Broemer et al. |
| 4,512,038 A | 4/1985 | Alexander et al. |
| 4,550,449 A | 11/1985 | Tunc |
| 4,781,183 A | 11/1988 | Casey et al. |
| 4,863,444 A | 9/1989 | Blomer |
| 4,919,666 A | 4/1990 | Buchhorn et al. |
| 5,013,315 A | 5/1991 | Barrows |
| 5,057,111 A | 10/1991 | Park |
| 5,084,050 A | 1/1992 | Draenert |
| 5,084,051 A | 1/1992 | Tormala et al. |
| 5,085,585 A * | 2/1992 | Zimble ............... A61C 19/063 |
| | | 433/215 |
| 5,108,399 A | 4/1992 | Eitenmuller et al. |
| 5,123,927 A | 6/1992 | Duncan et al. |
| 5,146,933 A | 9/1992 | Boyd |
| 5,268,178 A | 12/1993 | Calhoun et al. |
| 5,281,419 A | 1/1994 | Tuan et al. |
| 5,433,718 A | 7/1995 | Brinker |
| 5,458,653 A | 10/1995 | Davidson |
| 5,466,262 A | 11/1995 | Saffran |
| 5,569,250 A | 10/1996 | Sarver et al. |
| 5,607,474 A | 3/1997 | Athanasiou et al. |
| 5,618,286 A | 4/1997 | Brinker |
| 5,632,745 A | 5/1997 | Schwartz |
| 5,653,760 A | 8/1997 | Saffran |
| 5,676,699 A | 10/1997 | Gogolewski et al. |
| 5,681,289 A | 10/1997 | Wilcox et al. |
| 5,702,449 A | 12/1997 | McKay |
| 5,730,130 A | 3/1998 | Fitzpatrick et al. |
| 5,769,899 A | 6/1998 | Schwartz et al. |
| 6,039,762 A | 3/2000 | McKay |
| 6,102,914 A | 8/2000 | Bulstra et al. |
| 6,251,143 B1 | 6/2001 | Schwartz et al. |
| 6,296,645 B1 | 10/2001 | Hover et al. |
| 6,350,284 B1 | 2/2002 | Tormala et al. |
| 6,387,098 B1 | 5/2002 | Cole et al. |
| 6,447,515 B1 | 9/2002 | Meldrum |
| 6,468,314 B2 | 10/2002 | Schwartz et al. |
| 6,530,956 B1 | 3/2003 | Mansmann |
| 6,540,746 B1 | 4/2003 | Buhler et al. |
| 6,544,266 B1 | 4/2003 | Roger et al. |
| 6,572,623 B1 | 6/2003 | Birchall, Jr. et al. |
| 6,575,986 B2 | 6/2003 | Overaker |
| 6,579,533 B1 | 6/2003 | Tormala et al. |
| 6,596,296 B1 | 7/2003 | Nelson et al. |
| 6,663,634 B2 | 12/2003 | Ahrens et al. |
| 6,709,436 B1 | 3/2004 | Hover et al. |
| 6,716,957 B2 | 4/2004 | Tunc |
| 6,755,831 B2 | 6/2004 | Putnam et al. |
| 6,783,529 B2 | 8/2004 | Hover et al. |
| 6,786,908 B2 | 9/2004 | Hover et al. |
| 6,846,313 B1 | 1/2005 | Rogers et al. |
| 6,916,483 B2 | 7/2005 | Ralph et al. |
| 7,037,339 B2 | 5/2006 | Houfburg |
| 7,090,668 B1 | 8/2006 | U et al. |
| 7,090,688 B2 | 8/2006 | Nishtala et al. |
| 7,101,566 B2 | 9/2006 | Rosenblatt et al. |
| 7,192,604 B2 | 3/2007 | Brown et al. |
| 7,252,838 B2 | 8/2007 | O'Conner et al. |
| 7,255,713 B2 | 8/2007 | Malek |
| 7,316,822 B2 | 1/2008 | Binette et al. |
| 7,329,283 B2 | 2/2008 | Estes et al. |
| 7,361,195 B2 | 4/2008 | Schwartz et al. |
| 7,445,627 B2 | 11/2008 | Hawkes et al. |
| 7,517,362 B2 | 4/2009 | Shanley et al. |
| 7,517,914 B2 | 4/2009 | Richard |
| 7,527,611 B2 | 5/2009 | Sweeney |
| 7,534,264 B2 | 5/2009 | Fischer |
| 7,547,306 B2 | 6/2009 | Michelson |
| 7,550,011 B2 | 6/2009 | McKay et al. |
| 7,563,255 B2 | 7/2009 | Adamis et al. |
| 7,575,572 B2 | 8/2009 | Sweeney |
| 7,575,780 B2 | 8/2009 | Alexander et al. |
| 7,582,080 B2 | 9/2009 | Santini, Jr. et al. |
| 7,596,408 B2 | 9/2009 | Singhal et al. |
| 7,608,062 B2 | 10/2009 | Sweeney |
| 7,618,567 B2 | 11/2009 | Chi Sing et al. |
| 7,625,582 B2 | 12/2009 | Wong |
| 7,632,307 B2 | 12/2009 | Pacetti et al. |
| 7,648,504 B2 | 1/2010 | Heino et al. |
| 7,655,615 B2 | 2/2010 | Baumgartner |
| 7,658,727 B1 | 2/2010 | Fernandes et al. |
| 7,662,142 B2 | 2/2010 | Eaton et al. |
| 2003/0036761 A1* | 2/2003 | Smothers ............... A61B 17/60 |
| | | 424/426 |
| 2004/0009228 A1 | 1/2004 | Tormala et al. |
| 2004/0013703 A1 | 1/2004 | Ralph et al. |
| 2005/0090828 A1 | 4/2005 | Alford |
| 2005/0177162 A1* | 8/2005 | McLeod ............ A61B 17/8028 |
| | | 606/70 |
| 2006/0052782 A1 | 3/2006 | Morgan et al. |
| 2006/0058791 A1 | 3/2006 | Broman et al. |
| 2006/0188542 A1 | 8/2006 | Bobyn et al. |
| 2006/0241601 A1 | 10/2006 | Trautwein et al. |
| 2006/0247623 A1 | 11/2006 | Anderson et al. |
| 2006/0286140 A1 | 12/2006 | Wickstrom et al. |
| 2007/0173843 A1 | 7/2007 | Matityahu |
| 2007/0219556 A1 | 9/2007 | Altarac et al. |
| 2007/0219628 A1 | 9/2007 | Shanley et al. |
| 2007/0260324 A1 | 11/2007 | Joshi et al. |
| 2008/0015691 A1* | 1/2008 | Wyss ..................... A61F 2/3603 |
| | | 623/16.11 |
| 2008/0097432 A1 | 4/2008 | Schulze |
| 2008/0097441 A1 | 4/2008 | Hayes et al. |
| 2008/0119945 A1* | 5/2008 | Frigg ................... A61B 17/686 |
| | | 623/23.48 |
| 2008/0269893 A1 | 10/2008 | Bhatnagar et al. |
| 2008/0317812 A1 | 12/2008 | Zhang et al. |
| 2009/0005869 A1 | 1/2009 | Laurencin et al. |
| 2009/0010989 A1 | 1/2009 | Peters |
| 2009/0030399 A1 | 1/2009 | Raiszadeh |
| 2009/0047413 A1 | 2/2009 | Yang |
| 2009/0048675 A1 | 2/2009 | Bhatnagar |
| 2009/0048677 A1 | 2/2009 | McLeod et al. |
| 2009/0060971 A1 | 3/2009 | McKay |
| 2009/0062922 A1 | 3/2009 | McKay |

(56) References Cited

U.S. PATENT DOCUMENTS

| | | | |
|---|---|---|---|
| 2009/0087472 A1 | 4/2009 | Murphy et al. | |
| 2009/0088809 A1 | 4/2009 | Fisher | |
| 2009/0112315 A1 | 4/2009 | Fang | |
| 2009/0130167 A1* | 5/2009 | Shelton | A61F 2/30721 424/423 |
| 2009/0163919 A1 | 6/2009 | Tarcha et al. | |
| 2009/0163965 A1 | 6/2009 | Boyden | |
| 2009/0169595 A1 | 7/2009 | Dumont et al. | |
| 2009/0192500 A1 | 7/2009 | Cortez | |
| 2009/0198344 A1 | 8/2009 | Prentice et al. | |
| 2009/0292327 A1 | 11/2009 | Singhal et al. | |
| 2010/0015196 A1 | 1/2010 | Kimble et al. | |
| 2010/0021516 A1 | 1/2010 | McKay | |
| 2010/0028403 A1 | 2/2010 | Scheuermann et al. | |
| 2010/0042206 A1 | 2/2010 | Yadav et al. | |
| 2010/0055151 A1 | 3/2010 | Flanagan | |

FOREIGN PATENT DOCUMENTS

| | | |
|---|---|---|
| EP | 0236468 B1 | 7/1991 |
| EP | 0523926 A2 | 1/1993 |
| EP | 0523926 A3 | 1/1993 |
| EP | 0523926 A2 | 7/1997 |
| EP | 2052700 A1 | 4/2009 |
| WO | 8701595 | 3/1987 |
| WO | 02098307 A1 | 12/2002 |
| WO | 03005916 A1 | 1/2003 |
| WO | 2005027990 A1 | 3/2005 |
| WO | 2005027990 A3 | 3/2005 |
| WO | 2007014119 A2 | 2/2007 |
| WO | 2007014119 A3 | 2/2007 |
| WO | 2008035089 A1 | 3/2008 |
| WO | 2009015238 A1 | 1/2009 |
| WO | 2010045487 A1 | 4/2010 |

OTHER PUBLICATIONS

Gupta, at al. Bioactive materials for biomedical applications using so-gel technology, IOP electronic journals, 2008, Issue 3.

Schmidmaier, et al., Carrier systems and application of growth factors in orthopaedics, PubMed for Medline, 2008.

Palmetto Biomedical, Inc., International Search Report, International Patent Application No. PCT/US09/60889; filed Oct. 15, 2009, dated Feb. 4, 2010.

Palmetto Biomedical, Inc., Written Opinion of the International Searching Authority, International Patent Application No. PCT/US09/60889, filed Oct. 15, 2009, dated Feb. 4, 2010.

Trampuz, Andrej, at al , Diagnosis and treatment of infections associated with fracture-fixation devices, Injury, 2006, vol. 37, pp. S59-S66.

Gallo, J., et al, Pathogenesis of Prosthesis-Related Infection, Biomed. Papers, 2003, vol. 147, No. 1, pp. 27-35.

Richards, R., Introduction: Implants and infection in fracture fixation "ten years on", Injury, 2006, vol. 37, pp. S1-S2.

Kalicke, T., et al., Effect on Infection Resistance of a Local Antiseptic and Antibiotic Coating on Osteosynthesis Implants: An In Vitro and In Vivo Study, Journal of Orthopaedic Research, Aug. 2006, pp. 1622-1640.

Diefenbeck, Michael, et al., Prophylaxis and treatment of implant-related infections by local application of antibiotics, Injury, 2006, vol. 37, pp. S95-S104.

Darouiche, R., M.D. Treatment, of Infections Associated with Surgical Implants, The New England Journal of Medicine, 2004, vol. 250, pp. 1422-1429.

Harris, LG., et al., Staphylococci and implant surfaces: a review, Injury, 2006, vol. 37, pp. S3-S14.

Wu, P., et al., Drug/device combinations for local drug therapies and infection prophylaxis, Biomaterials, 2006, vol. 27, pp. 2450-2487.

Zalavras, C.G., M.D., et al., Local Antibiotic Therapy in the Treatment of Open Fractures and Osteomyelitis, Clinical Orthopaedics and Related Research, 2004, No. 427, pp. 86-93.

Palmetto Biomedical, Inc., International Preliminary Examining Authority, International Preliminary Report on Patentability issued for Application No. PCT/US2009/060899, Jan. 14, 2001, 19 pages.

Bioshape Solutions Inc., International Search Report and Written Opinion issued for International Application No. PCT/US2011/057114, Mar. 12, 2012, 16 pages.

Bioshape Solutions, Inc., European Application No. 09752559.6, Office Action, Jul. 31, 2013.

Bioshape Solutions Inc., European Application No. 09752559.6, Office Action, Jul. 16, 2014.

Bioshape Solutions Inc., European Application No. 11779911.4, Office Action, Oct. 31, 2014.

Bioshape Solutions Inc., European Application No. 11779911.4, Office Action, Aug. 21, 2015.

\* cited by examiner

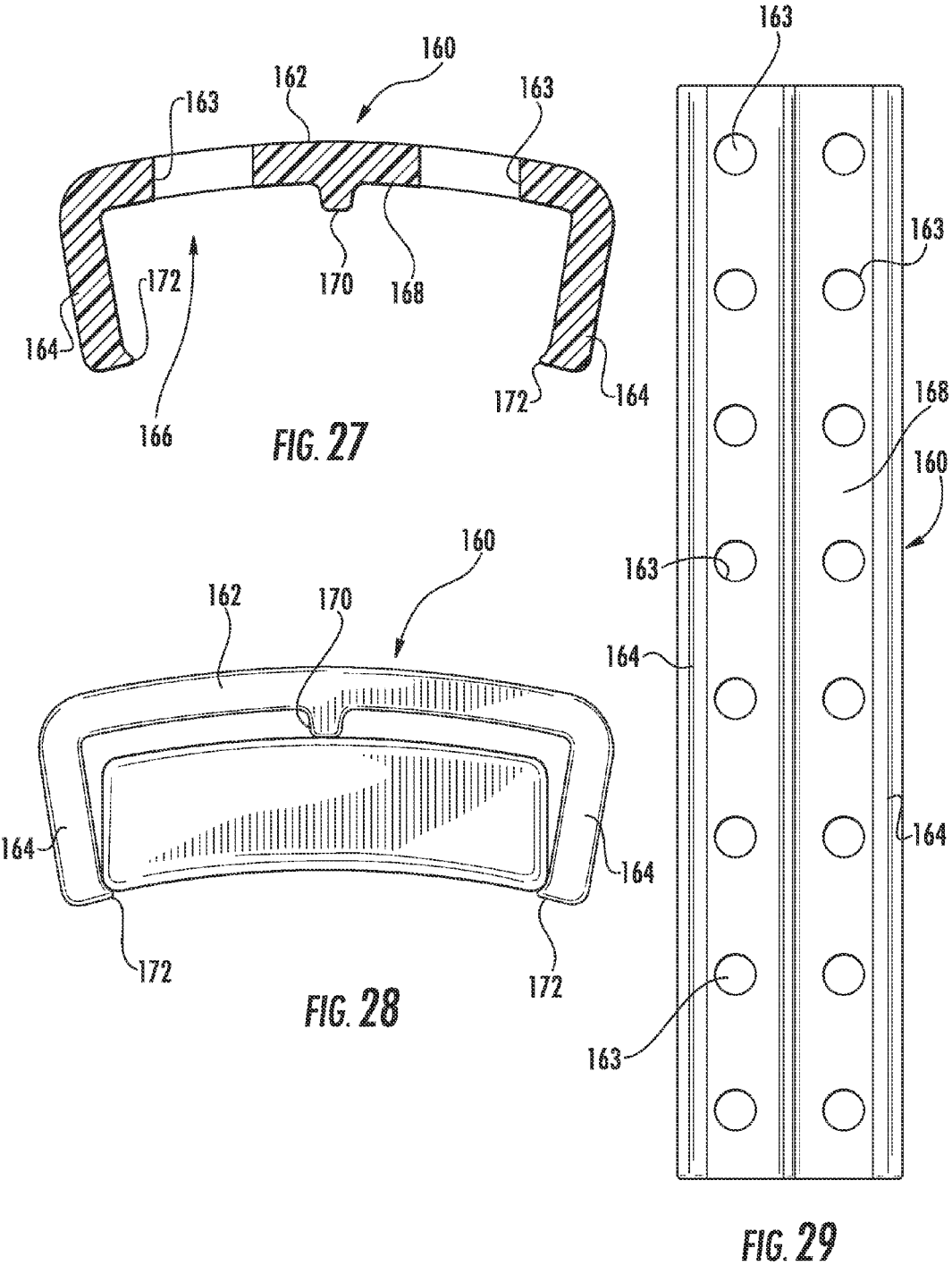

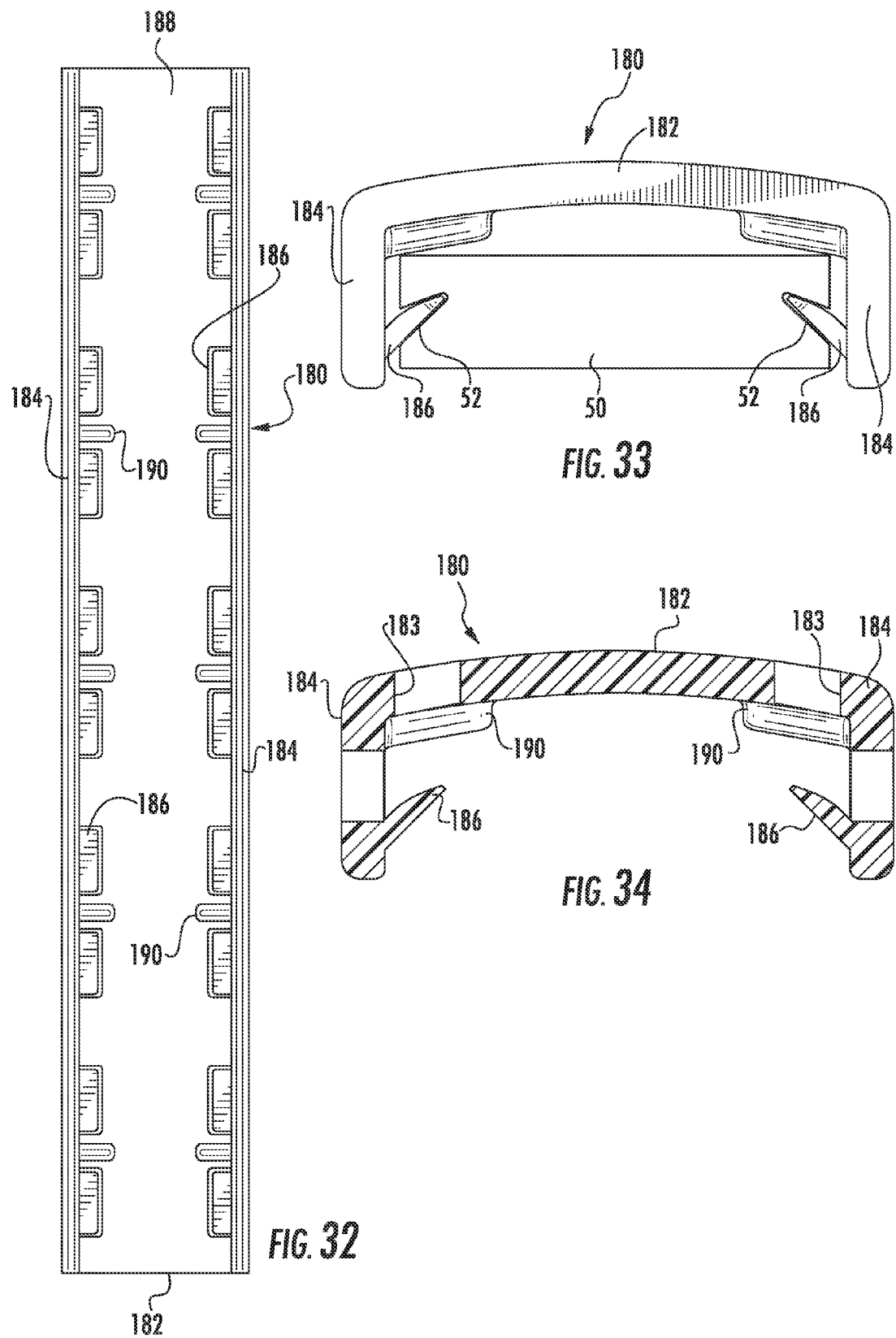

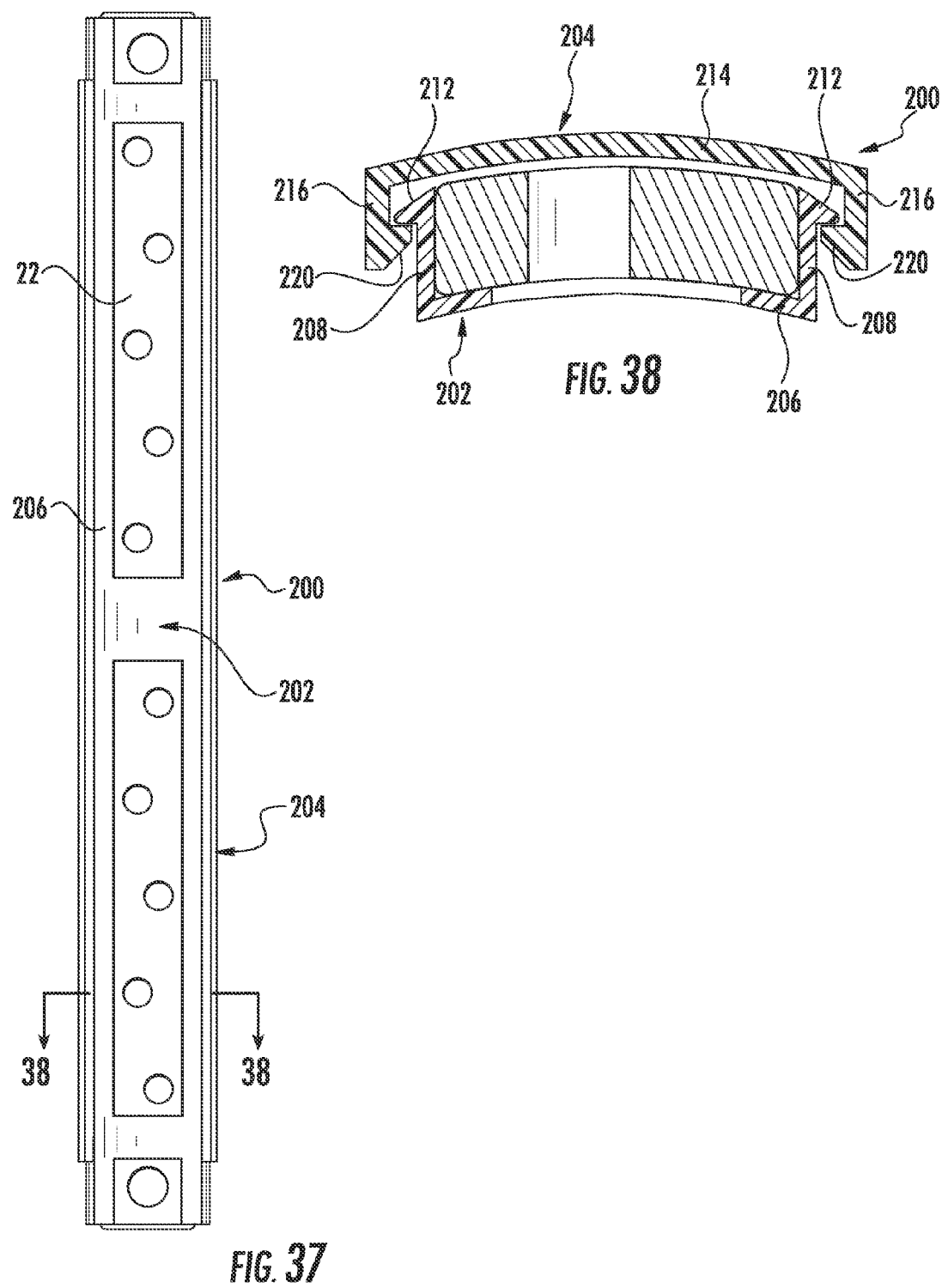

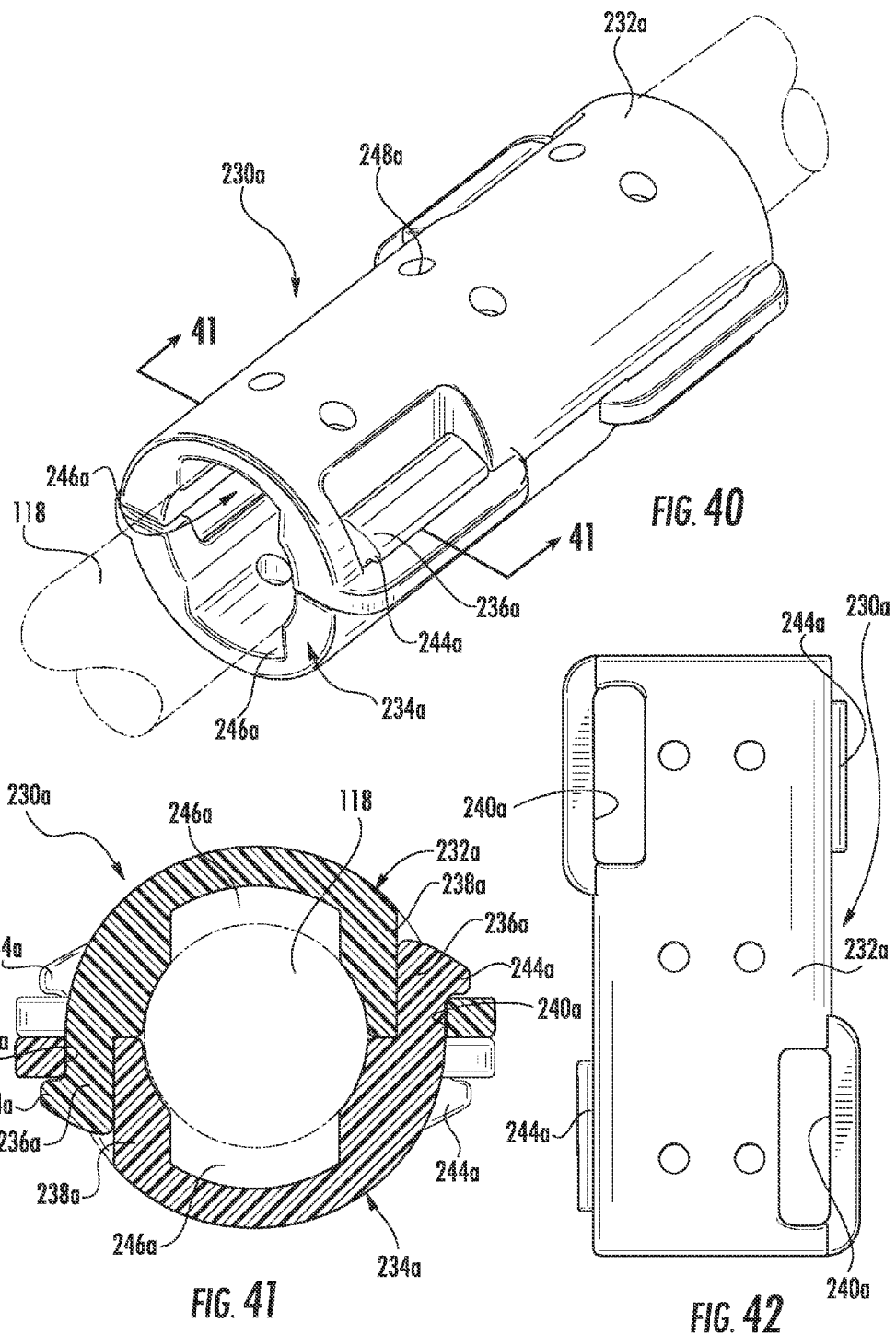

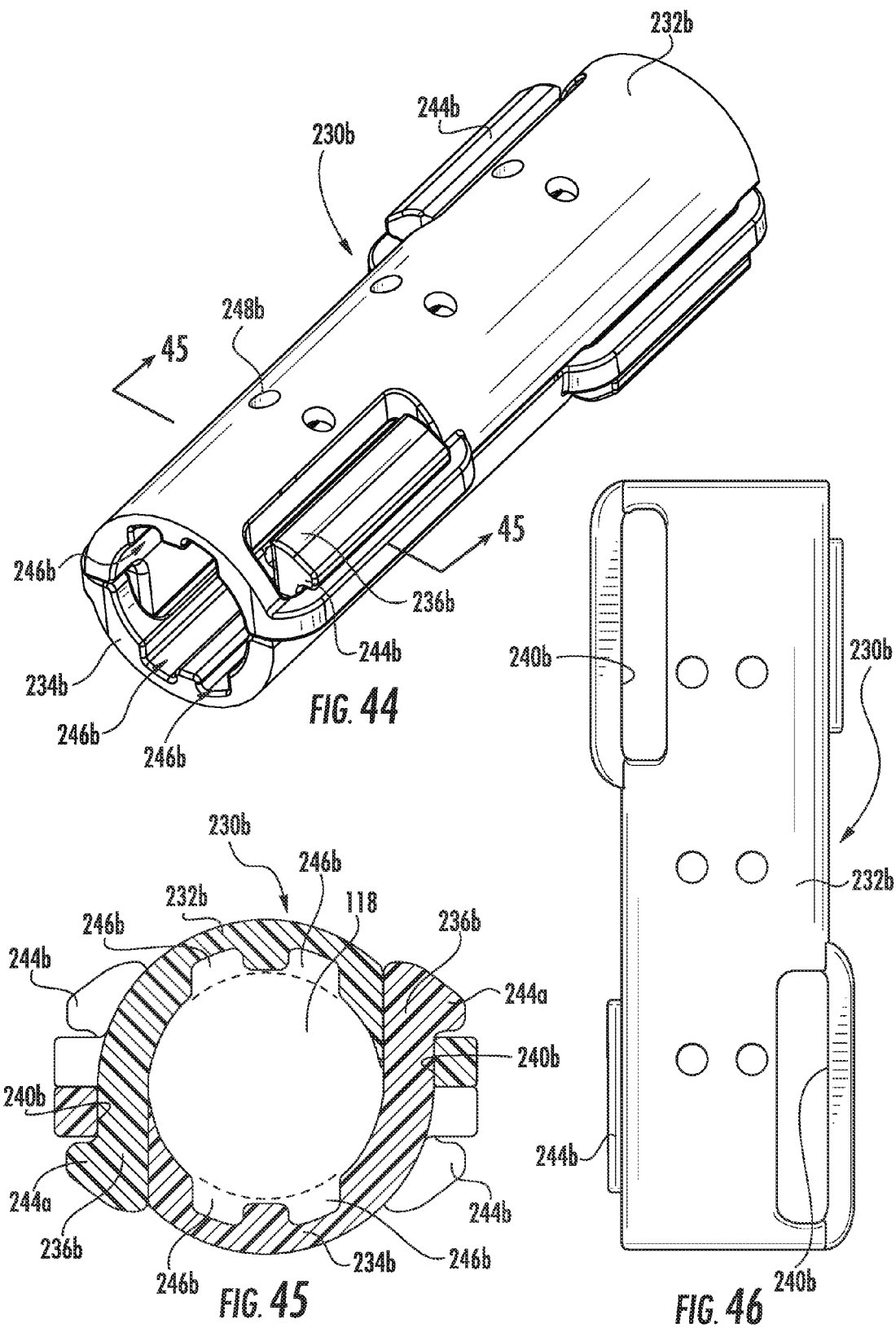

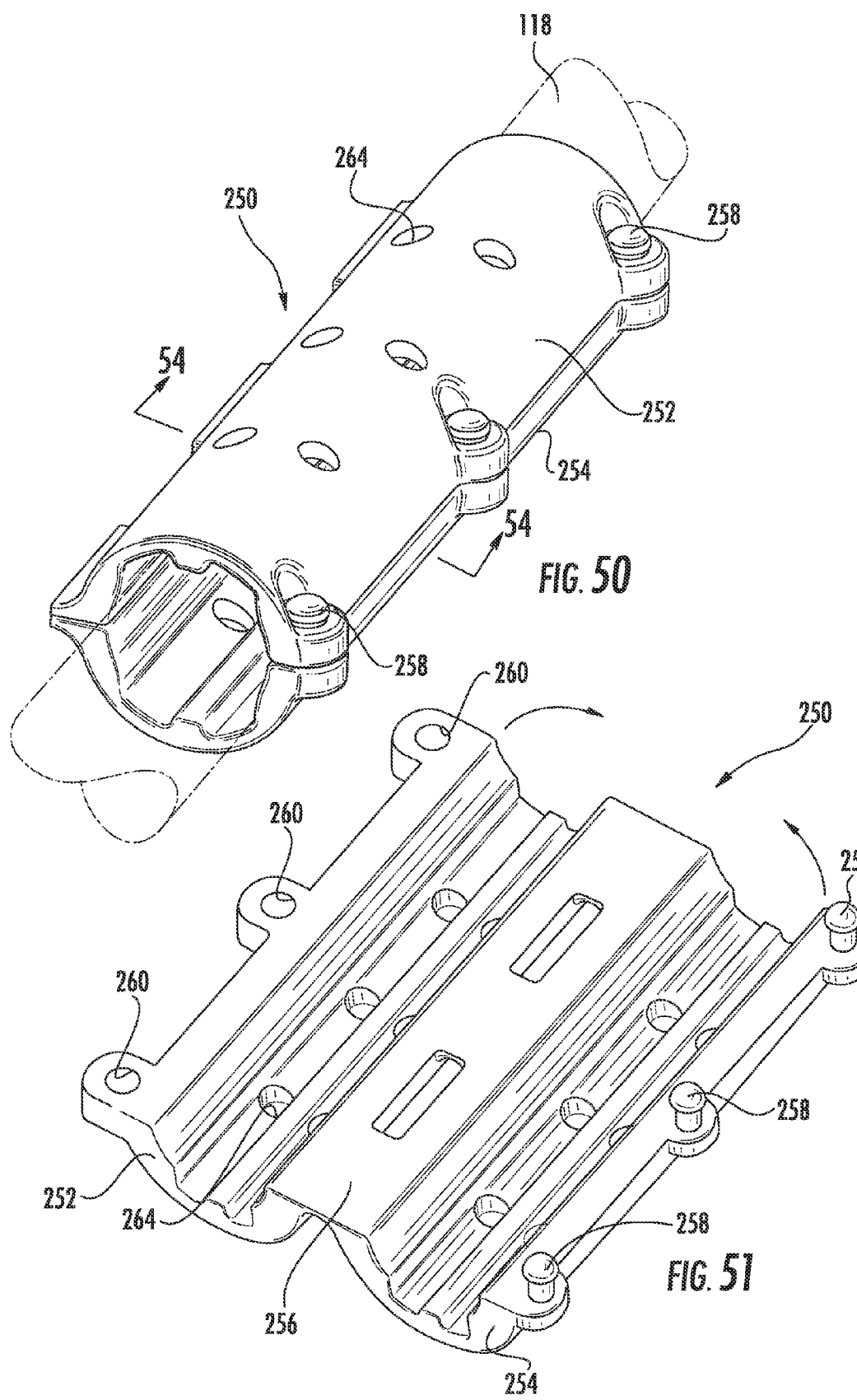

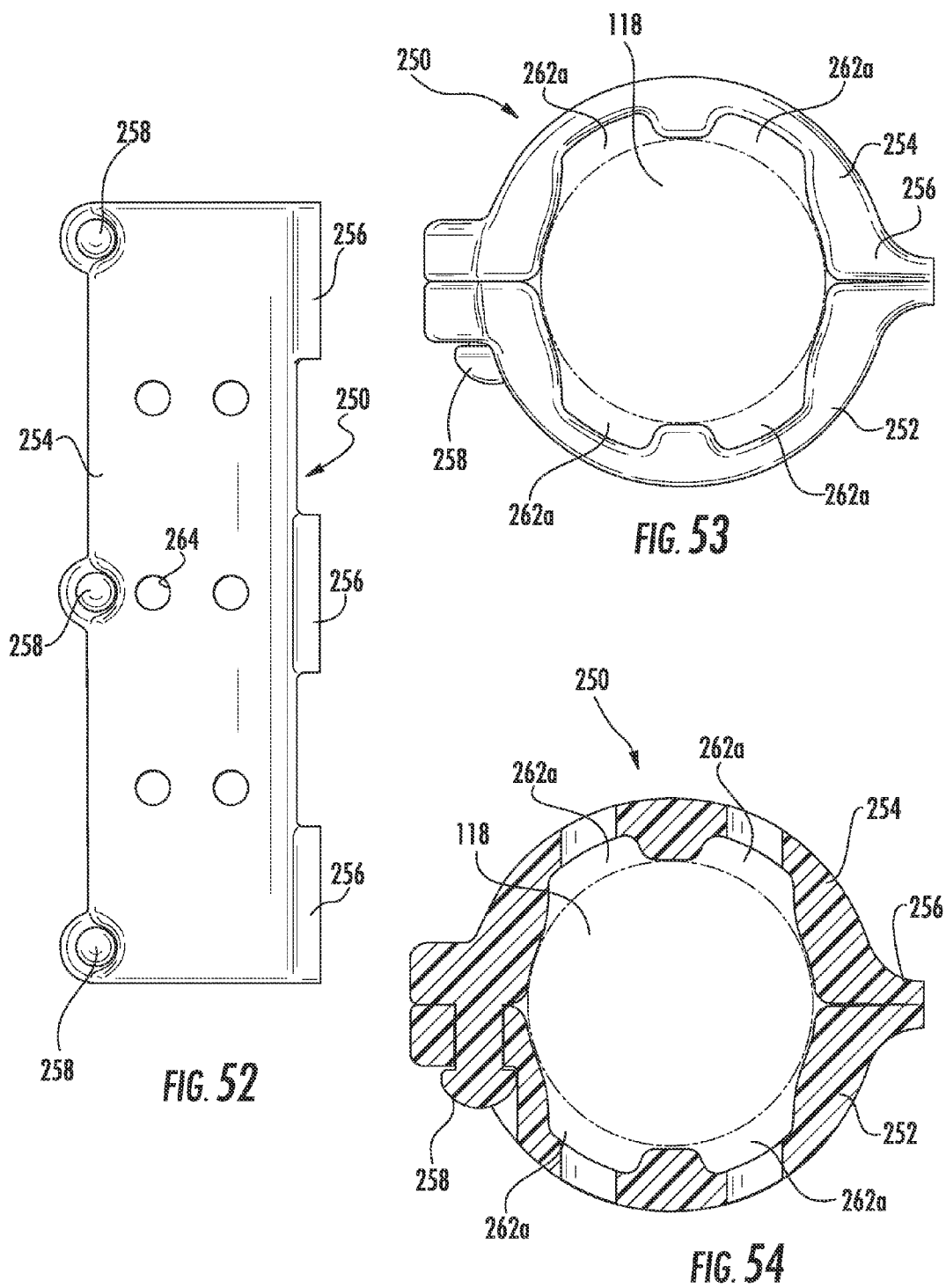

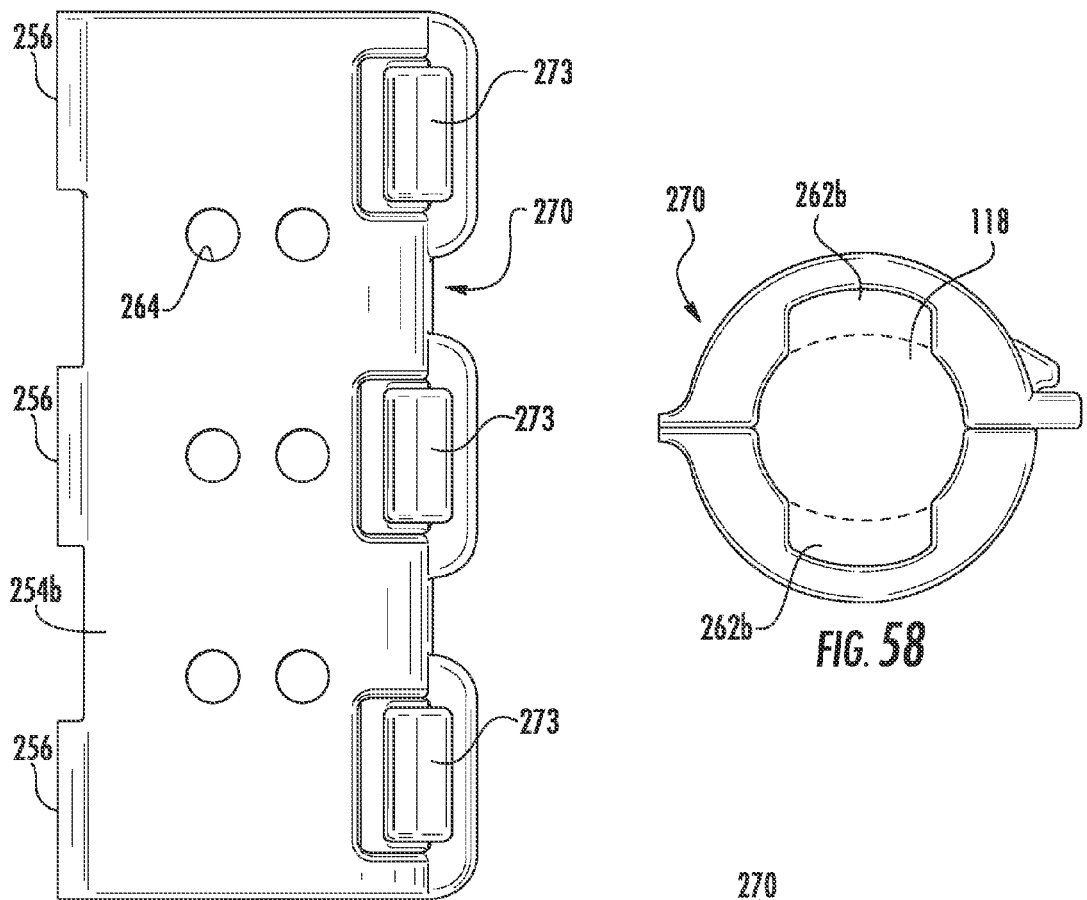
FIG. 57
FIG. 58
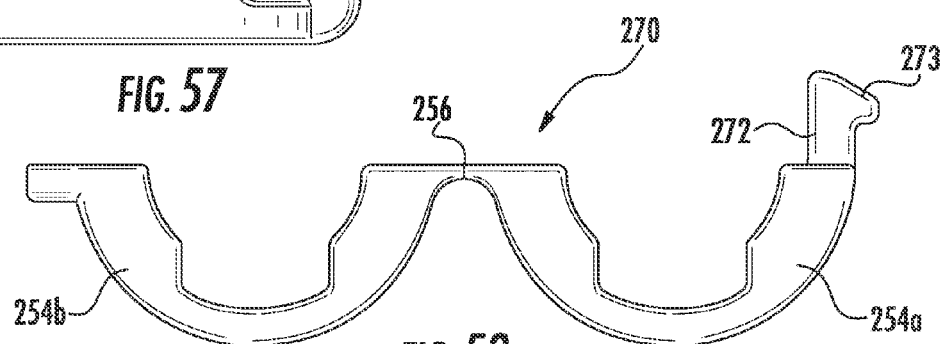
FIG. 59
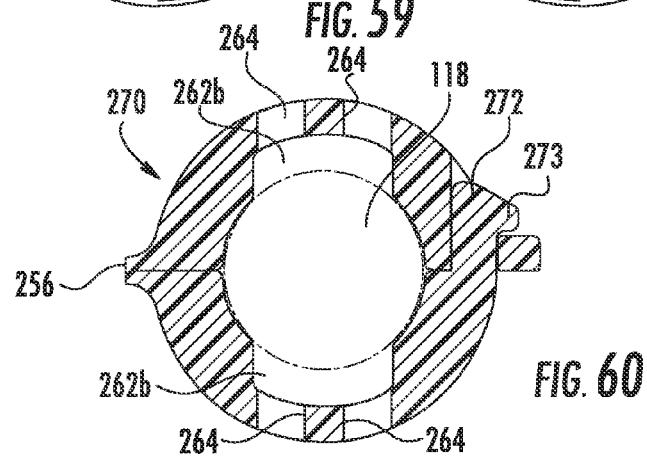
FIG. 60

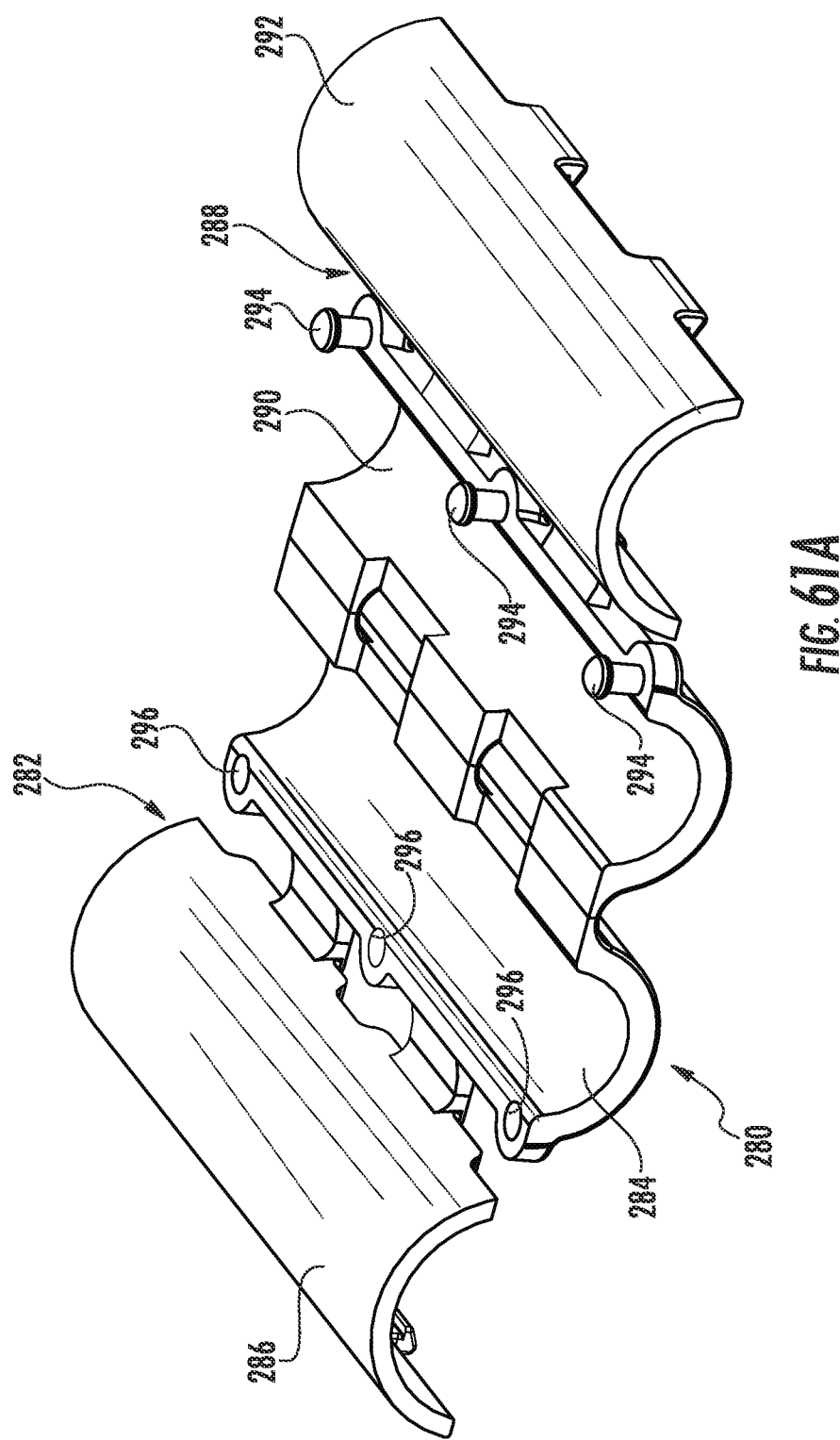

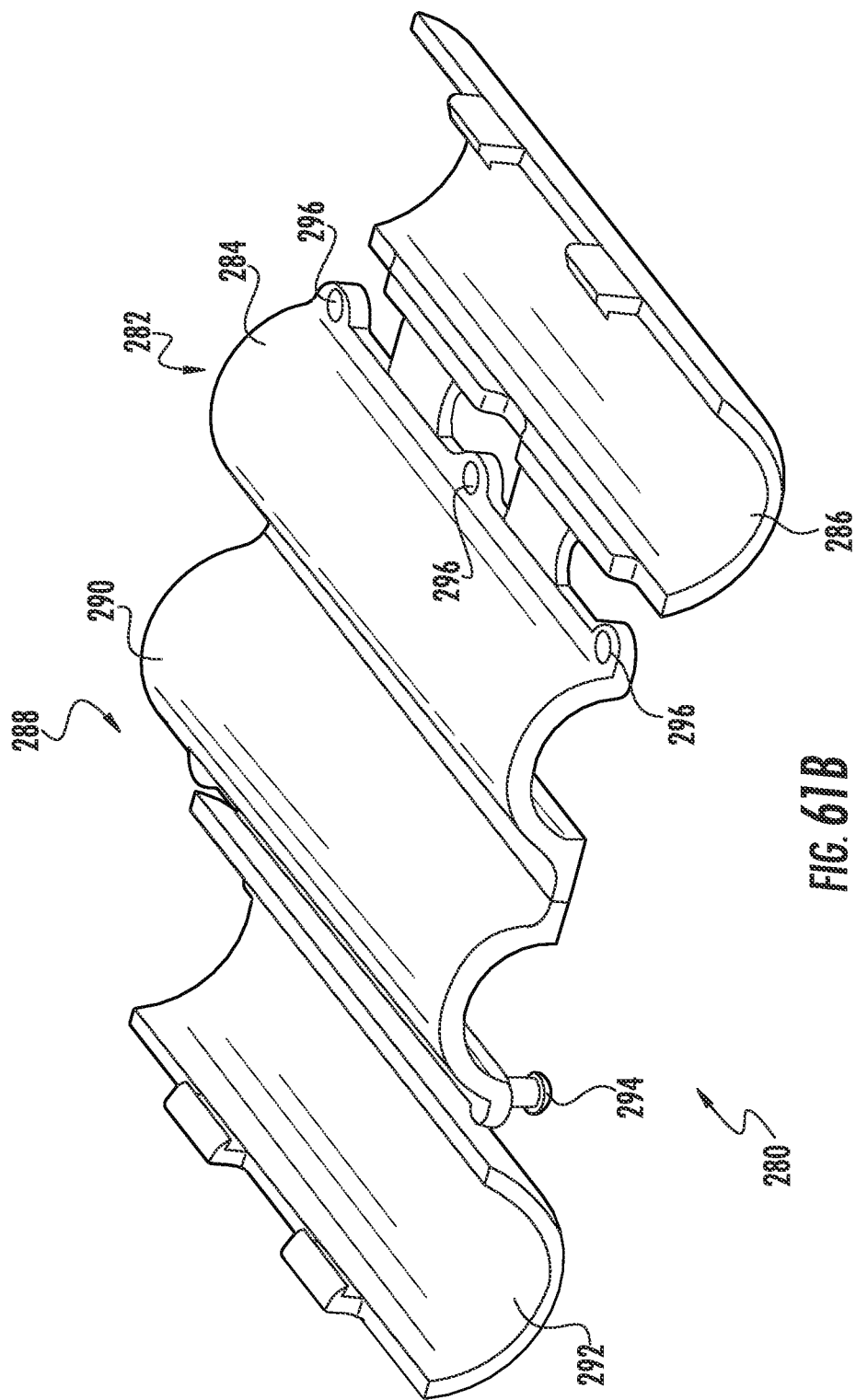

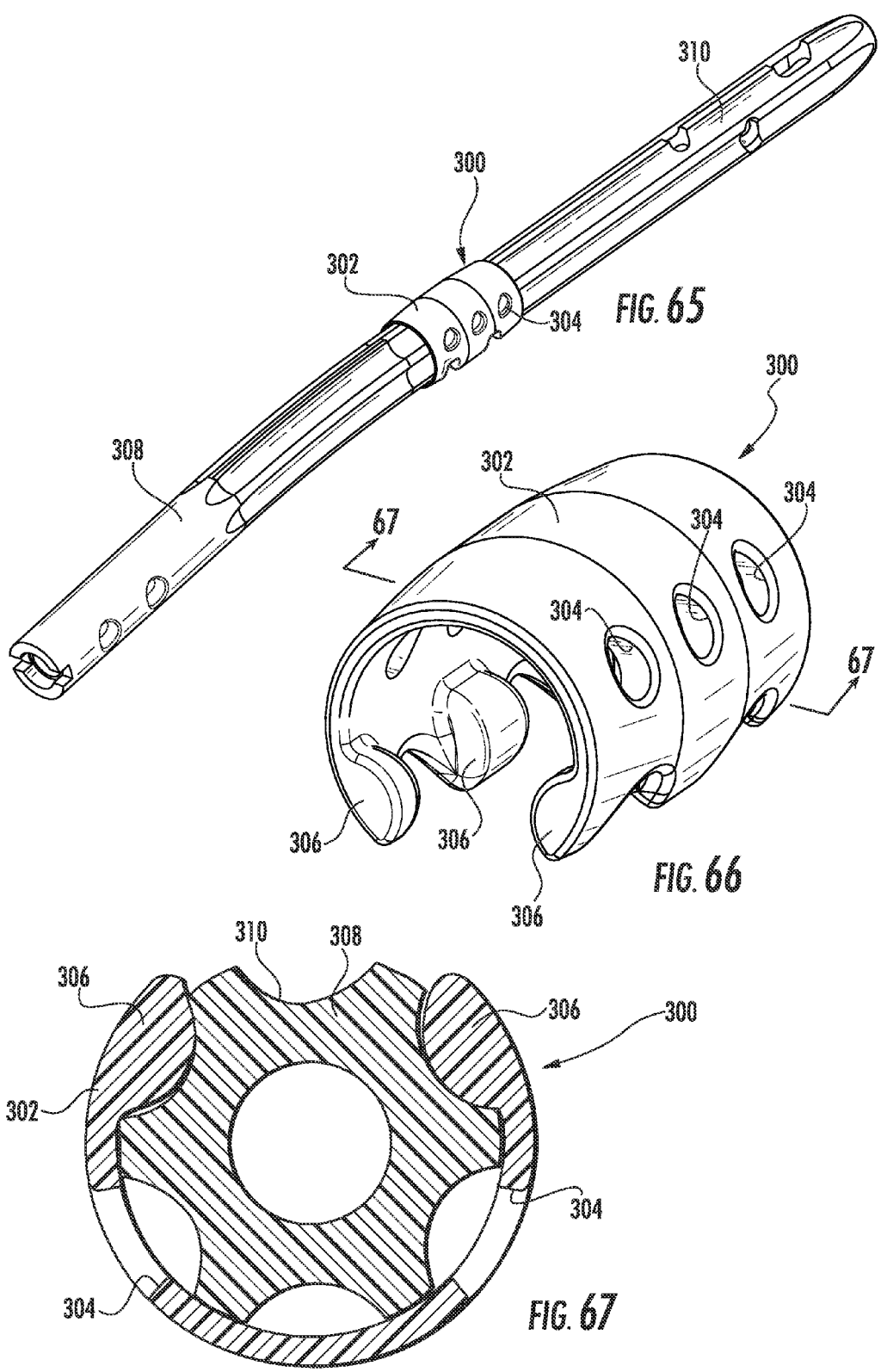

DEVICE AND METHOD FOR DELIVERY OF THERAPEUTIC AGENTS VIA INTERNAL IMPLANTS

CROSS-REFERENCES

This application is a continuation-in-part application of U.S. patent application Ser. No. 12/580,190, filed Oct. 15, 2009, entitled "Device And Method For Delivery of Therapeutic Agents Via Internal Implants," naming Lawrence M. Boyd, Samuel B. Adams, Jr., and Matthew R. Penny as inventors, currently pending, which claims the benefit of U.S. provisional application No. 61/105,659, filed Oct. 15, 2008. The contents of all of the above-listed applications are incorporated herein by reference in their entirety.

BACKGROUND

This invention relates generally to the delivery of therapeutic agents via artificial biomedical implants, and more particularly to an agent-delivery device adaptable to an internal biomedical implant.

There are many applications in which it is desirable to locally deliver a therapeutic agent adjacent to a biomedical implant such as a fracture plate, spinal rod or total joint prosthesis. For example, for growth factor delivery to secure accelerated bony fusion in a spinal fusion or fracture repair application, local delivery is necessary to concentrate the inductive agent at the site at which bone healing is desired. Another area in which local delivery would be advantageous involves the local delivery of an agent capable of reducing local pain and inflammation (e.g., an analgesic agent, therapeutic protein or antibody) alone or in concert with a surgical procedure such as a bony fusion. Finally, one area of great need involves local delivery of antibiotics for the treatment of implant associated infections.

Infections associated with surgical implants are generally difficult to manage because they require long periods of antibiotic therapy and repeated surgical procedures. Infections related to orthopedic devices and ventricular shunts often result in serious disabilities. Infected joint prosthesis occur in more than ten thousand clinical cases per year in the United States, while infected fracture fixation devices (e.g., fracture plates and intremedullary rods) are even more widespread, as there were nearly 100,000 infected fracture fixation implants in the United States in 2004 (Darouche, 2004). On average, about 5% of initially inserted internal fixation devices become infected. The infection rate for open fractures (those that involve compromise of the skin barrier) may exceed 30%. The cost to treat these infected implant sites is a significant cost to the healthcare system. For example, costs to treat spinal implant infection range from $40,000 to $400,000, depending on the severity and duration of the infection.

One significant challenge associated with the treatment of implant associated infections is the formation of a bacterial biofilm on the surface of the prosthesis. Bacteria biofilms involve the clustering of the microorganisms together in a highly hydrated extracellular matrix called a glycocalyx. Implants may be colonized acutely by perioperative airborne, skin- or surgeon-related bacteria seeded during surgery, or may adhere to the prosthesis via blood borne (hematogenous) pathogens at a later time. After attachment on the biomaterial surface, bacteria multiply and physiologically transform into a "biofilm" community. These biofilms are difficult to treat with systemic antibiotics for multiple reasons, including the quiescent nature of the bacteria in the biofilm community, poor vascularity of the biofilm, and its resistance to drug diffusion into the protein matrix (glycocalyx) formed by bacteria on the implant surface. Depletion of metabolic substances or waste product accumulation in biofilms also causes the microbes to enter into a slow growing or stationary phase, rendering them up to 1,000 times more resistant to most antimicrobial agents.

The nature of the surgical intervention to treat the infected device depends on the type of device, the presence or absence of bony union (for fracture fixation and spinal instrumentation devices) and the patient's underlying condition. For stable implants, debridement of the implant site, copious irrigation, high dose parenteral antibiotics and retention of the device with long-term (sometimes lifetime) oral antibiotic treatment is common. Surgical removal of the implant may be necessary to remove the source of the infection in the absence of a means of locally delivering high doses of therapeutic antibiotics, even in cases where the implant is still required for structural or functional performance. An additional follow-up procedure may be required to place a second implant once the infection is adequately treated.

Implant associated infections are often acquired in the hospital or surgical center. Federal (Medicare and Medicaid) and private insurers expend upwards of $1 billion treating hospital acquired, implant associated infections. This provides strong incentive and motivation for developing systems and methods for treating active infections and for preventing infection around medical devices.

A variety of methods are currently utilized to treat implant associated infection. These include the use of systemic prophylactic (pre- and post-operative) and post-infection antibiotics, delivery of antibiotic loaded PMMA bone cement, delivery of antibiotic loaded biomaterials, and active and passive surface coatings of the medical device prior to insertion. The most common method is to use systemic antibiotic therapy. However, these have been found to be expensive, prone to complications and very often not successful. One concern in delivering an antibiotic via the systemic route (oral, parenteral) involves the generally poor vascularity of the implant site, such as a bone fracture in the case of internal fixation implants. In order to deliver local therapeutic doses, it may be necessary to deliver high, and potentially toxic, levels of the antibiotic. The literature strongly supports the effectiveness of local treatment compared to systemic routes. This has been a major driving force toward developing methods to locally deliver a therapeutic agent. The local concentrations of antibiotic that can be achieved with local application cannot be achieved with systemic delivery, due to the toxic side effects that most antibiotics produce at such high systemic concentrations.

Another common method for treating implant associated infection, especially for joint replacement arthroplasty and large bony defects, has been the use of antibiotic impregnated bone cement (e.g., polymethylmethacrylate, PMMA). The antibiotic loaded cement may be mixed at the time of surgery, or a specially sized PMMA spacer may be used following removal of the prosthetic hip or knee replacement. In bone defects, for example with osteomyelitis, bone cement beads may be packed into the defect to increase surface-to-volume ratio for antibiotic delivery. For joint replacements, a two-stage replacement approach may be used, where the infected implant is removed and replaced by a biomaterial spacer until the infection is treated and a second prosthesis can be placed.

There are multiple concerns associated with the use of antibiotic-containing bone cement. Antibiotics may be slowly released over the first 4 weeks, after which a subtherapeutic dose of the antibiotic may be locally present. There are concerns that the lower dose of antibiotic in later time points, below the minimal inhibitory concentration (MIC) of resident bacteria, may lead to the formation of antibiotic-resistant strains of bacteria around the implant. Also, the bone cement is a two part system that may have residual toxic components, which also undergoes a highly exothermic reaction, both aspects capable of killing local bone cells needed for healing.

Other biomaterials have also been proposed for local delivery of antibiotics. These carriers include collagen scaffolds, bone substitutes (calcium based biomaterials) and allograft bone with incorporated antibiotic agents. For fracture treatment, placing these biomaterials in addition to the extensive hardware used to treat the fracture, and the need to maintain the material adjacent the implant site, have limited their utility in trauma and spine applications.

Implant coatings have been proposed as a means of reducing bacterial biofilm formation. Providing metal implants commonly used for internal fixation or spine surgery with a coating that contains and releases an antibacterial or antiseptic substance after surgery has been an appealing solution to the problem of implant associated infection. Antiseptic coatings such as silver ions and chlorhexidine/chloroxylenol may be immobilized on the implant surface. The main rationale for the use of an antiseptic instead of an antibiotic is the lower potential for developing resistant bacterial strains. Other efforts have involved the coating of the implant with a resorbable polymer coating or film loaded with an antibiotic or antiseptic agent. Animal studies have demonstrated the potential utility of the use of a resorbable biomaterial for local delivery. For example, Kalicke and coauthors reported in 2006 that the use of an antibacterial (Rifampicin and fusidic acid) and biodegradable (poly-1-lactide) coating on titanium fracture fixation plates resulted in a significant reduction in infection rate in an animal model ("Effect of infection resistance of a local antiseptic and antibiotic coating on osteosynthesis implants: an in vitro and in vivo study" *Journal of Orthopaedic Research* August 2006, pp. 1622-1640). Pilot clinical studies have been performed using polymer/antibiotic coated intramedullary nails for enhanced fracture repair (Schmidmaier, et al., 2006).

Others have proposed to modify the implant by adding channels or openings in the implant that can be filled with a drug-eluting biomaterial. The concept of machining channels into the implant for receipt of a drug eluting biomaterial or gel has been proposed. Concerns with these methods involve the need to prospectively modify the implants, the potential effect of these material modifications on the strength of the device and the potential for pockets or channels to harbor microbes.

For the foregoing reasons, there is a need for local and sustained delivery of therapeutic agents within the body of a patient. The new device should be easily adaptable to medical implants, such as bone fixation implants, spinal fixation implants or reconstructive prostheses.

SUMMARY

A device is provided for use with a medical implant for delivering an agent to a designated site of action in a body of a patient. The agent-delivery device comprises a body member having an inner surface and a projection on the inner surface of the body member. An agent-delivery medium is associated with the body member. The agent-delivery medium includes a therapeutic agent for treating the body of the patient. The body member is adapted to be secured to the medical implant such that the projection operatively engages the medical implant for spacing the inner surface of the body member from the implant, and the agent-delivery medium is configured to release the therapeutic agent after implantation in the body of the patient.

Another device is provided for use with a medical implant for delivering an agent to a designated site of action in a body of a patient. The agent-delivery device comprises a first body member having an inner surface and a second body member having an inner surface. Means are provided for connecting the first body member and the second body member. When connected, the inner surfaces of the first body member and the second body member define a cavity adapted to receive the medical implant.

Yet another device is provided for delivering an agent to a designated site of action in a body of a patient. The agent-delivery device comprises a body member defining an opening therethrough, the opening configured to receive an anchor member for fixing the body member in a body of a patient. An agent-delivery medium is associated with the body member. The agent-delivery medium includes a therapeutic agent for treating the body of a patient and is configured to release the therapeutic agent after implantation in the body of the patient.

BRIEF DESCRIPTION OF THE FIGURES

For a more complete understanding of the present invention, reference should now be had to the embodiments shown in the accompanying drawings and described below. In the drawings:

FIG. 27 is a cross-section view of the agent-delivery device taken along line 27-27 of FIG. 26

FIG. 28 is an end elevation view of the agent-delivery device shown in FIG. 26 adapted to an internal fracture fixation plate.

FIG. 29 is a bottom plan view of the agent-delivery device shown in FIG. 26.

FIG. 32 is a bottom plan view of the agent-delivery device shown in FIG. 30.

FIG. 33 is an end elevation view of the agent-delivery device shown in FIG. 30 adapted to an internal fracture fixation plate.

FIG. 34 is a cross-section view of the agent-delivery device taken along line 34-34 of FIG. 30.

FIG. 37 is a bottom plan view of the agent-delivery device shown in FIG. 35 adapted to the internal fracture fixation plate.

FIG. 38 is a cross-section view of the agent-delivery device taken along line 38-38 of FIG. 37.

FIG. 40 is a perspective view of the agent-delivery device shown in FIG. 39 adapted to the rod.

FIG. 41 is a cross-section view of the agent-delivery device taken along line 41-41 of FIG. 40.

FIG. 42 is a top plan view of one part of the two identical parts of the agent-delivery device shown in FIG. 39.

FIG. 44 is a perspective view of the agent-delivery device shown in FIG. 43 adapted to receive the rod.

FIG. 45 is a cross-section view of the agent-delivery device take along line 45-45 of FIG. 44.

FIG. 46 is a top plan view of one part of the two identical parts of the agent-delivery device shown in FIG. 43.

FIG. 50 is a perspective view of another embodiment of an agent-delivery device adapted to a rod for a spinal fusion construct.

FIG. 51 is a perspective view of the agent-delivery device shown in FIG. 50 in an open position.

FIG. 52 is a bottom plan view of the agent-delivery device shown in FIG. 50 when in a closed position.

FIG. 53 is an end elevation view of the agent-delivery device shown in FIG. 50 adapted to the rod, in the closed position.

FIG. 54 is a cross-section view of the agent-delivery device taken along line 54-54 of FIG. 52 in the closed position.

FIG. 57 is a top plan view of the agent-delivery device shown in FIG. 55 when in the closed position.

FIG. 58 is an end elevation view of the agent-delivery device shown in FIG. 55 adapted to the rod when in the closed position.

FIG. 59 is an end elevation view of the agent-delivery device shown in FIG. 55 adapted to the rod when in the open position.

FIG. 60 is a cross-section view of the agent-delivery device shown in FIG. 55 taken along line 60-60 when in the closed position.

FIGS. 61A and 61B are top and bottom perspective views, respectively, of another embodiment of an agent-delivery device when in an open position.

FIG. 65 is a perspective view of another embodiment of an agent-delivery device adapted to an intermedulary nail.

FIG. 66 is a perspective view of the agent-delivery device shown in FIG. 66.

FIG. 67 is a cross-section view of the agent-delivery device shown in FIGS. 65 and 66.

DESCRIPTION

Figure 1:
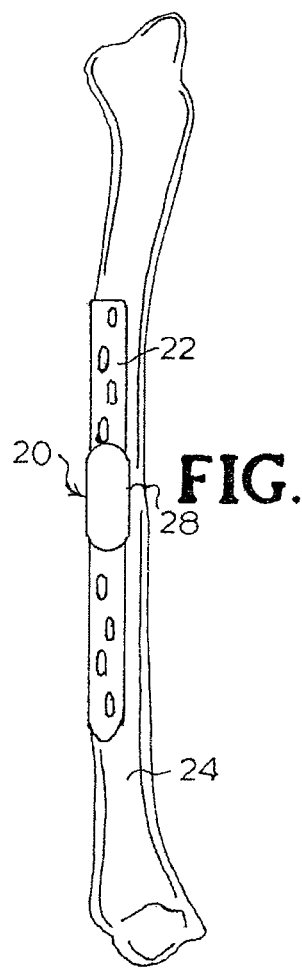
FIG. 1 is an elevation view of an embodiment of an agent-delivery device adapted to an internal fracture fixation plate secured to a bone fracture.

As used herein, the terms "therapeutic agent" or "agent" are used interchangeably and refer to a compound or composition of matter which, when presented to an organism, human or animal, induces a desired pharmacologic or physiologic effect by local or systemic action. For example, the therapeutic agent includes one or more compounds or composition of matter providing enhanced bone density or bone growth, anti-infection, anti-inflammation, chemotaxis (cellular attraction), cellular differentiation (such as stem cell differentiation down different lineages) or pain relief to the area in proximity to the implant. The term therapeutic agent also includes biological substances such as cells and cell-derived substances found to have a potentially beneficial therapeutic effect at the site of the implant. Cell derived substances may include blood platelet-derived preparations and concentrations, such as platelet rich plasma (PRP). PRP and other cell derived preparations have been shown to have potential therapeutic benefit such as bone osteoinduction for fracture repair. Cells may also be the therapeutic agent of interest, such cells delivered into or onto the devices and migrating to nearby sites for repair and regeneration. These include both cells directly harvested from the patient (autogeneous) and those from donor sources (allogenic). Cells types may be of a range of adult or juvenile cell types and may include both already differentiated cells or undifferentiated multipotent stem cells. Stem cells may be from a range of cell lineages, including mesenchymal cells from bone marrow, adipogenic cells from fatty tissues and also those from umbilical cord blood, among others. In addition, these cells may be treated outside the patient, such as via gene therapy, prior to reintroduction at the repair site of interest.

As used herein, the term "therapeutically effective amount" refers to an amount of a therapeutic agent that is nontoxic but sufficient to provide a desired effect. For example, a therapeutically effective amount is an amount sufficient to measurably decrease the symptom or etiology of a bone tissue trauma or to measurably enhance the rate of the targeted cell division, cell migration or cell attachment as necessary to accelerate bone healing and quality of the bone formed in response to injury. The therapeutically effective amount varies according to the patient's presentation, sex, age and weight, the rate of administration, the nature of the condition and any treatments which may be associated therewith, or any concurrent related or unrelated treatments or conditions of the patient. Therapeutically effective amounts can be determined without undue experimentation by any person skilled in the art or by following the exemplary guidelines set forth herein.

As used herein, the term "absorbable" or variations thereof mean the ability of a tissue-compatible material to degrade or biodegrade at some time after implantation into products that are eliminated from the body or metabolized therein. Thus, as used herein, "absorbability" means that the material is capable of being absorbed, either fully or partially, by tissue by cellular or biochemical means when implanted into a human or animal. The absorption time may vary depending on the particular uses and tissues involved.

As used herein, the term "non-absorbable" or variations thereof mean completely or substantially incapable of being absorbed, either fully or partially, by tissue after introduction to the subject.

Certain terminology is used herein for convenience only and is not to be taken as a limitation on the invention. For example, words such as "upper," "lower," "left," "right," "horizontal," "vertical," "upward," and "downward" merely describe the configuration shown in the FIGs. Indeed, the components may be oriented in any direction and the terminology, therefore, should be understood as encompassing such variations unless specified otherwise.

Described herein are devices and methods for the local delivery of therapeutic agents to a site of bone fracture, healing or fixation and to surrounding tissues, allowing for immediate, continuous or sustained delivery of therapeutic agents, such as those used to prevent infection or to enhance the tissue healing process. In one aspect, an agent-delivery device is provided that securely adapts to an internal medical implant. Adaptation of the agent-delivery device to the medical implant may be implemented prior to or following implantation (at any time, including a separate surgical procedure at a later date) of the medical implant or other medical device, and may involve secure or reversible fixation.

Referring now to the drawings, wherein like reference numerals designate corresponding or similar elements throughout the several views, an agent-delivery device for delivering therapeutic agents for use with an internal fracture fixation plate is shown in FIG. 1, and generally designated at 20. As is conventional, the plate 22 is fastened to a bone 24 using screws 26 such that the plate 22 spans either side of a fracture 28 or repair site. The agent-delivery device 20 is securely adaptable to the plate, allowing for a highly localized delivery of one or more therapeutic agents in the area around the plate 22. The term "securely adaptable" includes any fastening or securing means. Thus, it is understood that multiple means of adaptation are anticipated that can be used to attach the agent-delivery device to a wide range of medical implants, and is inclusive of securement means providing relative motion of the agent-delivery device relative to the medical implant, such as sliding along an axis of the plate 22 shown in FIG. 1.

The agent-delivery device can be formed of either synthetic or natural materials, including, but not limited to, thermoplastics, thermoset polymers, elastomers, rubbers, or woven or non-woven composite materials. The agent-delivery device may be, for example, any suitable molded form of a polymeric, plastic foam (including open celled foam), woven composite or non-woven composite, mixtures thereof, or the like. In particular, a suitable agent-delivery device may thus be prepared, for example, from Nylon, a polyolefin, such as polyethylene, including UHMW polyethylene, structural plastics such as PEEK (polyetheretherketone), polysulfone, polypropylene, ethylene propylene copolymers, and ethylene butylene copolymers, polyurethanes, polyurethane foams, polystyrenes, plasticized polyvinylchlorides, polyesters, Delrin polyacetal, and polyamides, and homopolymer and copolymers of the above. It is understood that the agent-delivery device may assume a variety of shapes as necessary to accommodate and adapt to a variety of fixation plates.

The agent-delivery device may be absorbable or non-absorbable. In one aspect, the agent-delivery device may be formed from an absorbable polymer, such as a polymer, copolymer, or homopolymer of glycolide, lactide, caprolactone, trimethylene carbonate, or dioxanone, such as a copolymer of caprolactone and L-lactide, and may include absorbable polyester such as PGA, PLA, PLLA and others like PGLA. In one embodiment, the agent-delivery device may be fabricated out of an absorbable polymer that comprises a therapeutic agent via incorporation of a drug or other therapeutic agent into the base polymer for elution following implantation.

The agent-delivery device may also be fabricated from known biocompatible metals or their alloys such as titanium, stainless steel, cobalt chromium or a combination of multiple types of the materials listed herein.

The agent-delivery device may comprise an amount of a therapeutic agent effective in obtaining a desired local or systemic physiological or pharmacological effect. Suitable therapeutic agents include, but are not limited to, medicaments such as analgesics, anesthetics, antibiotics, antibacterial agents, antifungal agents, anti-inflammatory agents, antimicrobials, antiseptics, bacteriocins, bacteriostats, disinfectants, steroids, antiviral agents, antitumor agents, growth promoting substances, protein antibodies, antioxidants, or mixtures thereof.

Such therapeutic agents for use in combination with the agent-delivery device further include, but are not limited to, acetic acid, aluminum acetate, bacitracin, bacitracin zinc, benzalkonium chloride, benzethonium chloride, betadine, calcium chloroplatinate, certrimide, cloramine T, chlorhexidine phosphanilate, chlorhexidine, chlorhexidine sulfate, chloropenidine, chloroplatinatic acid, ciprofloxacin, clindamycin, clioquinol, cysostaphin, gentamicin sulfate, hydrogen peroxide, iodinated polyvinylidone, iodine, iodophor, minocycline, mupirocin, neomycin, neomycin sulfate, nitrofurazone, non-onynol 9, potassium permanganate, penicillin, polymycin, polymycin B, polymyxin, polymyxin B sulfate, polyvinylpyrrolidone iodine, povidone iodine, 8-hydroxyquinoline, quinolone thioureas, rifampin, rifamycin, copper chloride, copper sulfate, copper peptides, silver acetate, silver benzoate, silver carbonate, silver chloride, silver citrate, silver iodide, silver nitrate, silver oxide, silver sulfate, sodium chloroplatinate, sodium hypochlorite, sphingolipids, tetracycline, zinc oxide, salts of sulfadiazine (such as silver, sodium, and zinc), vitamins such as vitamin E, other agents mentioned above, and mixtures thereof. Preferable bioactive materials are USP approved, more preferably USP monographed.

Additional examples of agents include one or more members selected from the group consisting of anabolic agents, analgesic agents, antiresorptive agents aromatase inhibitors, chondroitin sulphate, COX-2 inhibitors, COX-3 inhibitors, disease modifying anti-rheumatic compounds (DMARDs), glucocorticoids, glucosamine, glycine antagonists, inhibitors of inducible nitric oxide synthetase (iNOS), inhibitors of interleukin-1 converting enzyme, inhibitors of matrix metallo-proteinases (MMPs), inhibitors/antagonists of IL-1, inhibitors/antagonists of RANK-ligand, inhibitors/antagonists of TNF-oc, N-acetylcholine receptor agonists, neurokinin antagonists, neuroleptic agents, NMDA receptor antagonists, non-steroidal anti-inflammatory agents (NSAIDs), opioids, pallitative agents, PAR2 receptor antagonists, selective estrogen receptor modulators (SERMs), vanilloid receptor antagonists, anti-infectives, anti-inflammatories, antioxidants, chlorhexidine, silver sulfadiazine, glycosaminoglycans, natural and truncated forms of parathyroid hormone (PTH), aminated natural and truncated forms of parathyroid hormone (PTH), parathyroid hormone related peptide (PTHrP), anabolic Vitamin D analogs, low-density lipoprotein receptor-related protein 5, non-genomic estrogen-like signaling activator, bone morphogenic protein (BMP), insulin-like growth factor (IGF), fibroblast growth factor (FGF), sclerostin, leptin, a prostaglandin, statin, growth hormone, growth hormone releasing factor (GHRF), hepatocyte growth factor (HGF), calcitonin gene related peptide (CGRP), transforming growth factor (TGF)-.beta.1, human calcitonin, non-human calcitonin, calcitonin gene related peptide (CGRP), hormone replacement therapy (HRT) agents, selective estrogen receptor modulators, bisphosphonates, divalent sources of strontium, fusidic acid, cathepsin-K inhibitors, and antibiotics such as rifampicin, gentamicin, vancomycin and others broadly including bacteriocidal antibiotics such as those which target the bacterial cell wall (penicillins, cephalosporins), or cell membrane (polymixins), or interfere with essential bacterial enzymes (quinolones, sulfonamides), bacteriostatic antibiotics which target protein synthesis, such as the aminoglycosides, macrolides and tetracyclines, and newer antibiotics including the three classes: cyclic lipopeptides (daptomycin), glycylcyclines (tigecycline), and oxazolidinones (linezolid).

Particularly preferred therapeutic agents for use in combination with fracture fixation devices include agents capable of modifying bone healing and remodeling, for example, one or more of calcium salts, strontium salts, vitamin D2 or D3, alphacalcidol, calcitriol or dihydrotachysterol, parathyroid hormone (PTH), bisphosphonates, calcitonin, selective estrogen receptor modulators (SERMs), tissue-specific synthetic steroid analog (a selective tissue estrogenic activity regulator-STEAR), bone morphogenic protein (BMP), glucosamine sulphate and/or other glucosamine containing substances, and/or glucagon like peptide 2 (GLP-2). Other growth factors for bone formation besides BMP may include members of the insulin-like growth factor family, platelet-derived growth factor family, fibroblast growth factor family, transforming growth factor family, proteins important to bone formation including collagens, matrix proteogylcans, osteopontin, alkaline phosphatase, and cell surface attachment molecules like integrins and cadherins. Local regulators of bone include interleukins, prostoglandins, and epidermal growth factor.

Other agents of interest may include, but are not limited to, steroids, pain medication and human monoclonal antibodies such as anti-Tumor Necrosis Factor alpha 1.

One or more therapeutic agents may be located within, or optionally on, the agent-delivery device. For example, the therapeutic agents can be dispersed in the agent-delivery device, such as by being absorbed, or adsorbed, contained, chemically bound, physically bound, or combinations thereof to the agent-delivery device. In addition, the therapeutic agents can be either immobilized on the agent-delivery device, for example so that the agent has a desired effect but is not detached from the material of the device during use, or the agent can be attached to the agent-delivery device in a manner such that the agent becomes detached during use. It is understood that any surface or combination of surfaces, of the agent-delivery device herein described may be the site of the therapeutic agent. Further, the agent-delivery device may be manufactured to provide an immediate, continuous or sustained drug delivery profile.

In another embodiment, the agent-delivery device may comprise at least one portion permeable to the passage of therapeutic agent, allowing diffusion of the agent out of the agent-delivery device. One or more portions of the agent-delivery device may further comprise an impermeable section at least partially surrounding the permeable portion. For example, the agent-delivery device may be formed of an impermeable outer layer at least partially surrounding a permeable portion. A section of the impermeable outer layer may be configured for removal for controlled diffusion of the agent. Alternatively, the impermeable section may contain pores, or openings, of a size capable of providing a targeted agent-delivery profile.

In another embodiment, the agent-delivery device may contain a removable cover or lid to expose the agent or the permeable sections of the agent-delivery device. The cover may be configured to be removed immediately before or after adapting the agent-delivery device to the bone fixation device, for example, just prior to surgically implanting the fixation device.

In one aspect, the agent-delivery device may be configured to adapt to a medical implant, such as a fracture fixation plate, by sliding onto the medical implant. One embodiment of a "slide-on" device is shown in FIGS. 2A-2E and generally designated at 30. The agent-delivery device 30 is an elongated member having a substantially oval profile and comprises a substantially major base portion 32 having a longitudinal axis. The base portion 32 spans between generally planar side walls 34, or legs, two of which depend from the longitudinal edges of each side of the base portion 32. Each of the side walls 34 terminates in longitudinal edges. The base portion and the side walls define an open longitudinal channel 36. As shown in the FIGs., the side walls 34 are angled inwardly relative to the base portion 32.

Figure 3:
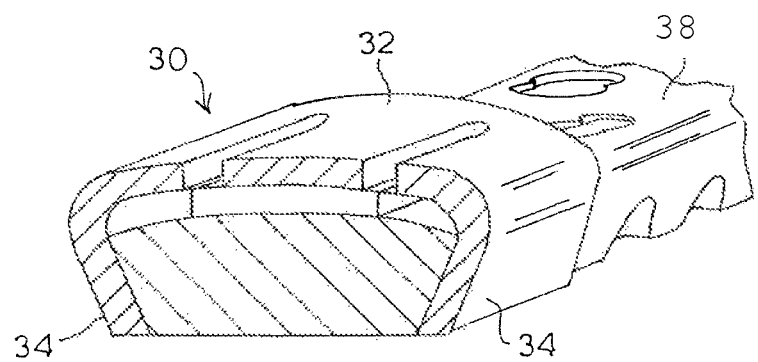
FIG. 3 is a cross-section view of the agent-delivery device shown in FIG. 2A adapted to an internal fracture fixation plate.

Referring to FIG. 3, the agent-delivery device 30 having this configuration is adaptable to a fracture fixation plate 22 having an upper surface that is wider than the lower surface (the surface against the bone). In use, the agent-delivery device 30 is adapted to the fracture fixation plate 38 by sliding the device onto the end of the plate. The agent-delivery device 30 may be moved to a desired location along the length of the plate 38 manually or by an instrument such as facilitated by a blunt tamp.

Figure 4:
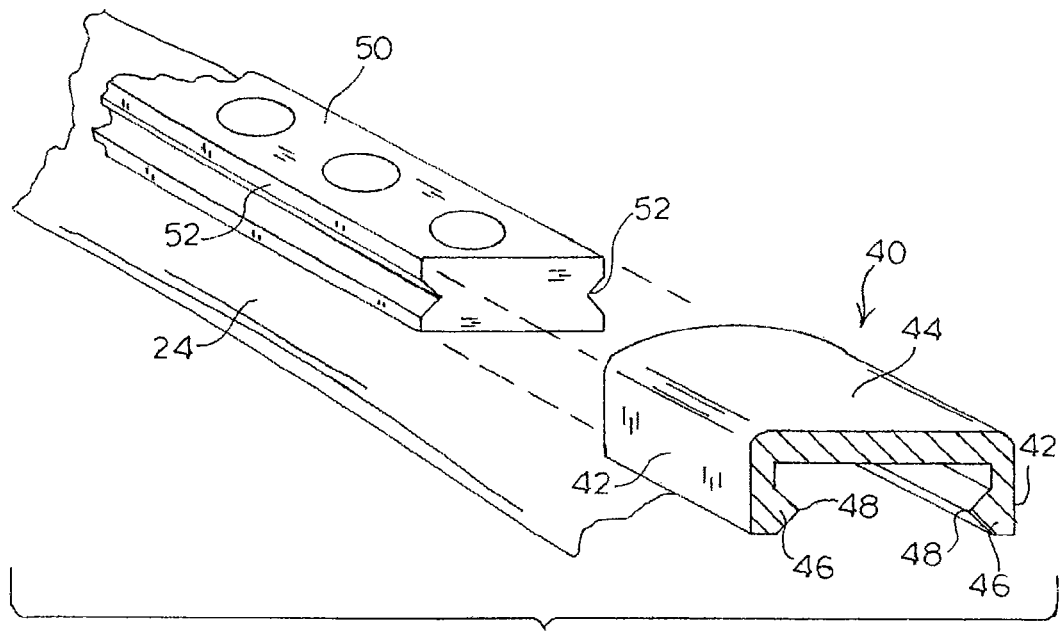
FIG. 4 is an exploded perspective view in partial cross-section of another embodiment agent-delivery device for use with an internal fracture fixation plate secured to a bone fracture.
Figure 5:
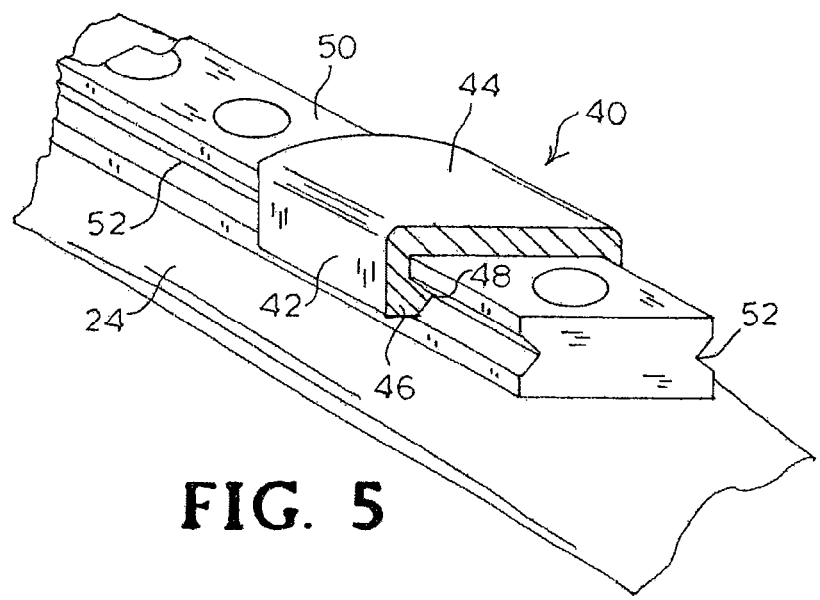
FIG. 5 is a perspective view in partial cross-section of the agent-delivery device as shown in FIG. 4.

FIG. 4 illustrates another embodiment of a slide-on agent-delivery device and is generally designated at 40. In this embodiment, side walls 42 depend generally perpendicularly along the length of the edges of the base portion 44. In addition, the side walls 42 terminate in flanges 46, which extend inwardly substantially normal to the plane of the side walls 42. The distal ends of the flanges 46 are tapered forming opposed pointed terminal edges 48 which are disposed substantially parallel with respect to the side walls 42. As shown in FIGS. 4 and 5, the sides of the fracture fixation plate 50 define longitudinal grooves 52 corresponding to the pointed edges 48 of the agent-delivery device 40 for slidably receiving the agent-delivery device.

Figure 6:
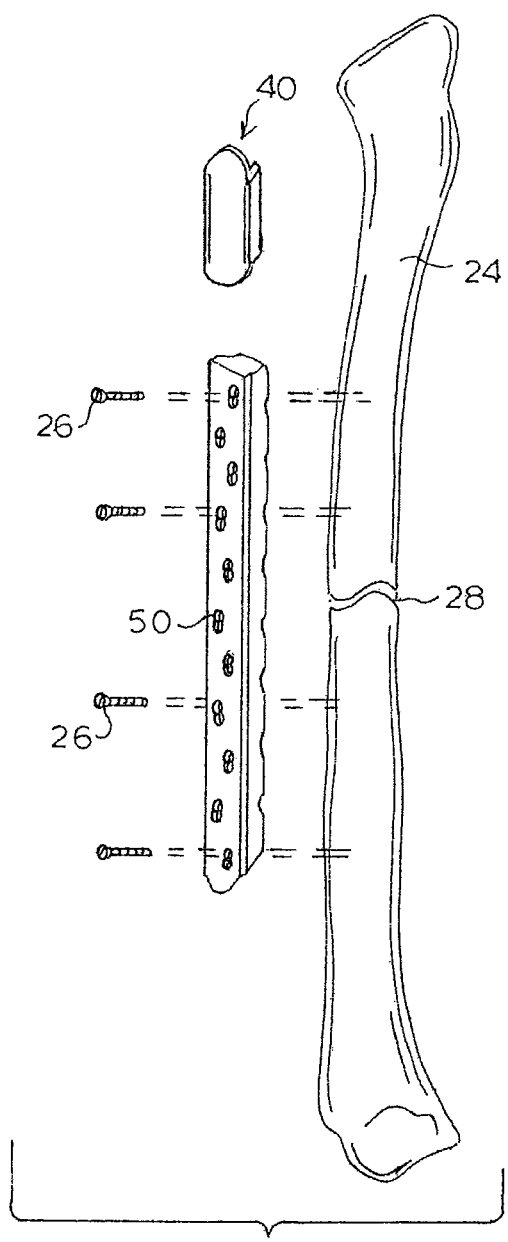
FIG. 6 is a exploded perspective view of the agent-delivery device as shown in FIG. 4 and an internal fracture fixation plate and fasteners for securing to a bone fracture.

Referring to FIG. 6, in use, the fracture fixation plate 50 is fixed, using surgical screws 26 or other fasteners, to each side of a fracture 28, or otherwise surgically altered site, of a bone 24. The agent-delivery device 40 is adapted by sliding the device onto the end of the fracture fixation plate 50 such that the pointed terminal edges 48 of the flanges 46 are slidably received in the longitudinal grooves 52 in the sides of the plate 50. The agent-delivery device 40 may be advanced along the length of the plate 50 manually or by an instrument such as facilitated by a blunt tamp. The agent-delivery device 40 is positioned so that the agent-delivery device is located proximate to the fracture 28 or the surgical alteration site, as shown in FIG. 1. This is to enable one or more therapeutic agents associated with the device 40 to be delivered to the fracture 28 or site as quickly and efficiently as possible with minimal loss to the system and maximum benefit to the patient. It is understood that the agent-delivery device 40 may be adapted to the fracture fixation plate 50 prior to securing the plate to the bone 24.

Figure 7:
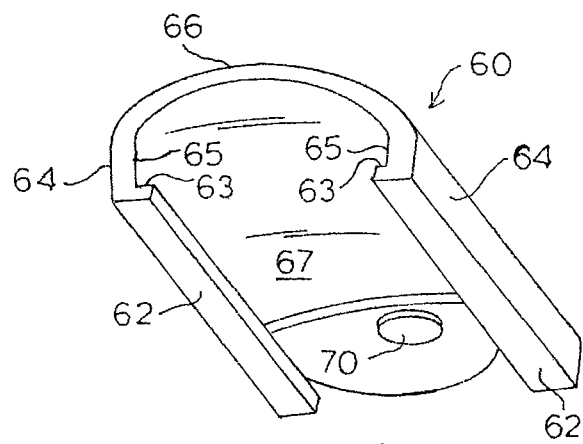
FIG. 7 is a bottom perspective view of another embodiment of an agent-delivery device.

Another embodiment of a slide-on agent-delivery device is shown in FIG. 7 and generally designated at 60. In this embodiment, a continuous inwardly extending flange 62 extends the length of associated side walls 64. The agent-delivery device 60 is sized and shaped such that the distance between the inner surface 65 of the side walls 64 and the distance between the inner surface 67 of the base portion 66 and the upper surface 63 of the flanges 62 is slightly larger than width and thickness, respectively, of the fracture fixation plate 68.

Figure 8:
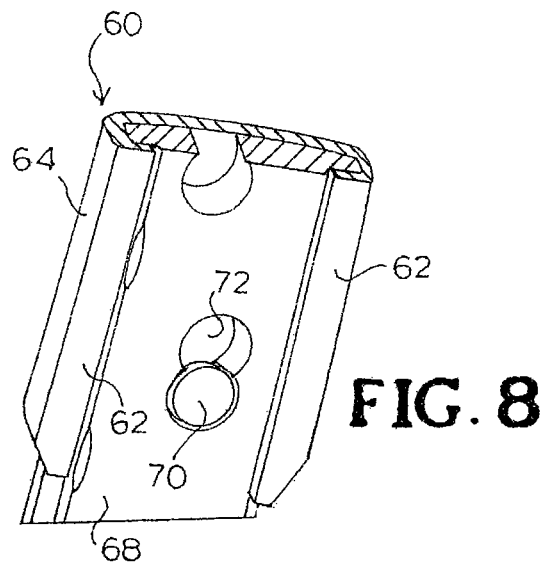
FIG. 8 is a cross-section of a bottom perspective view of the agent-delivery device shown in FIG. 7 in place on a fracture fixation plate.
Figure 9:
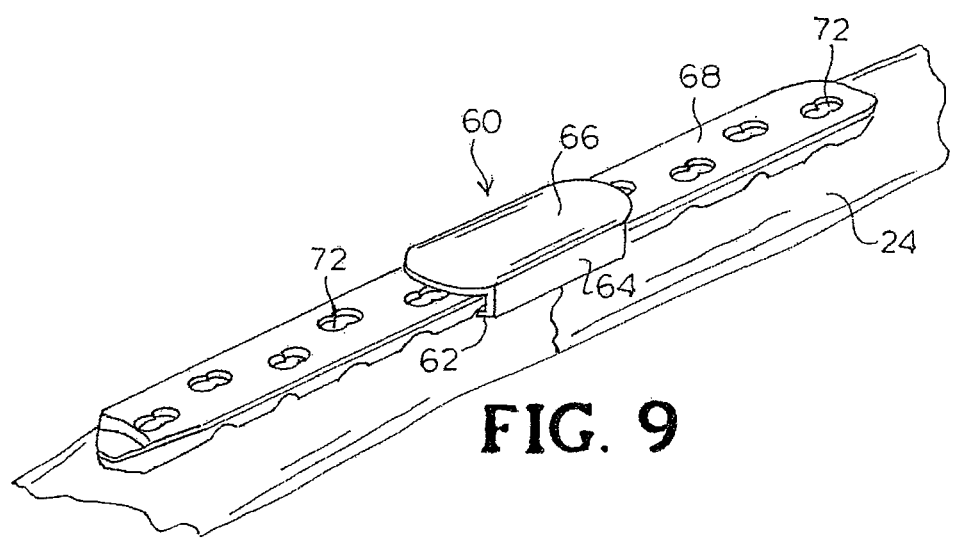
FIG. 9 is a perspective view of the agent-delivery device as shown in FIG. 8.
Figure 10A:
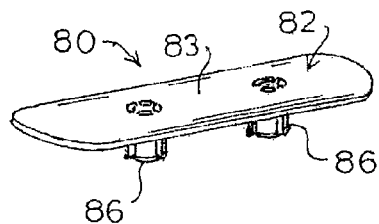
FIG. 10A is a top perspective view of a snap-in embodiment of an agent-delivery device.
Figure 10B:
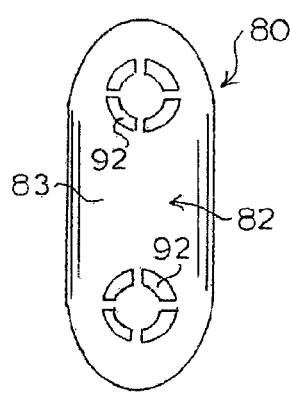
FIG. 10B is a top plan view of the agent-delivery device shown in FIG. 10A.
Figure 10C:
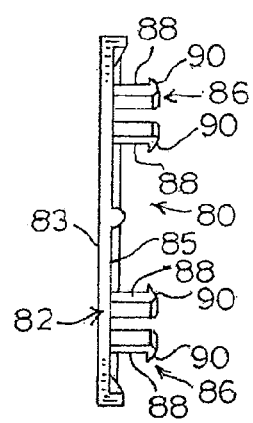
FIG. 10C is a side elevation view of the agent-delivery device shown in FIG. 10A.
Figure 10D:
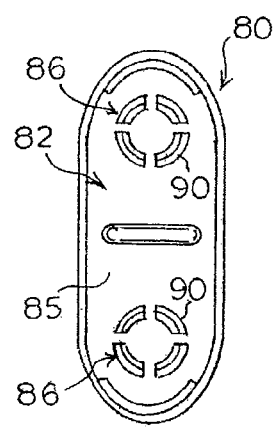
FIG. 10D is a bottom plan view of the agent-delivery device shown in FIG. 10A.
Figure 10E:
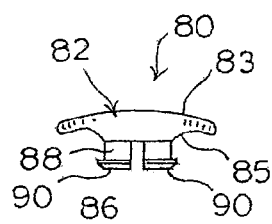
FIG. 10E is an end view of the agent-delivery device shown in FIG. 10A.

Accordingly, the agent-delivery device 60 is adapted to the fracture fixation plate 68 by sliding the device over the end of the plate, as shown in FIG. 8. In this embodiment, the location of the agent-delivery device 60 relative to the fracture fixation plate 68 may be controlled using a button 70 depending from the inner surface 67 of the base portion 66 of the device (FIG. 7). The button 70 results in one or more areas of increased friction between the agent-delivery device 60 and the plate 68. The button 70 may be sized and shaped to be received within a hole 72 in the plate 68 to prevent relative sliding movement from a desired location. In addition, the agent-delivery device 60 may produce an audible snap as the device is advanced along the fracture fixation plate 68, thereby aiding control of the movement of the agent-delivery device 60 along the plate by providing audible and tactile indicia to the user. Corresponding features could also be formed along the sides of the fracture fixation device 68.

It is understood that in any of the slide-on embodiments described herein, that the pairs of opposed side walls may be sized and shaped to correspond to the sides of the fracture fixation plate so that the agent-delivery may optionally snap into place over the plate. For example, a medical grade polymer material can allow the agent-delivery device to flex sufficiently during installation to accomplish a snap-fit.

An embodiment of an agent-delivery device configured to "snap-in" at a desired location on a fracture fixation plate is shown in FIG. 10 and generally designated at 80. The agent-delivery device 80 comprises a base portion 82 having a top surface 83 and a bottom surface 85. Two inserts 86 extend at spaced locations from the bottom surface 85 of the base portion 82. Each insert 86 has a cross-section that is generally circular in shape and includes a length measured from the bottom surface 85 of the base portion 82. Each insert 86 comprises four spaced arcuate legs 88. An outwardly extending flange 90 is located at the distal end of each leg 88. A series of arcuate slots 92 define separate rings on the top surface 83 of the base portion 82.

Figure 11:
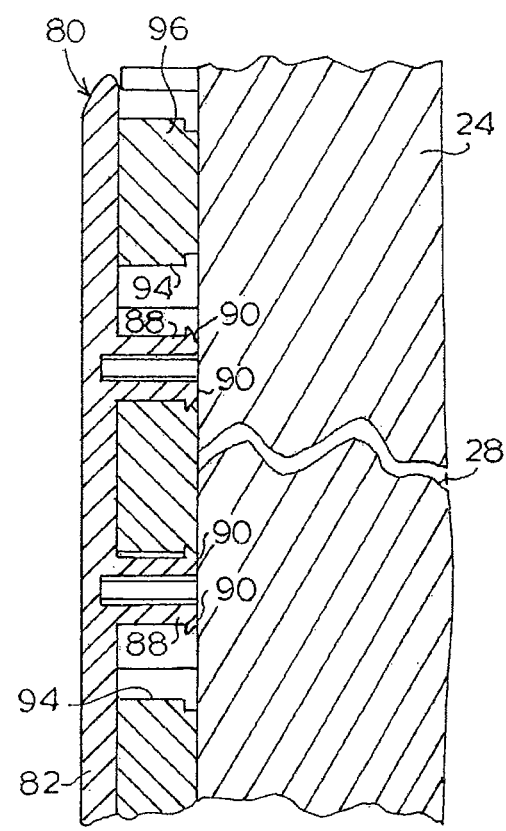
FIG. 11 is a longitudinal cross-section view of the agent-delivery device shown in FIGS. 10A-10E adapted to an internal fracture fixation plate secured to a bone fracture.
Figure 2A:
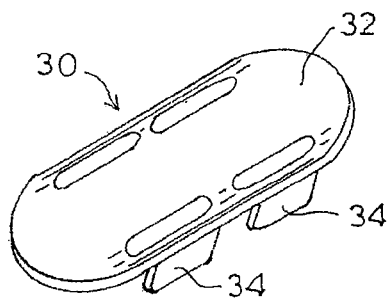
FIG. 2A is a top perspective view of an embodiment of an agent-delivery device.
Figure 2B:
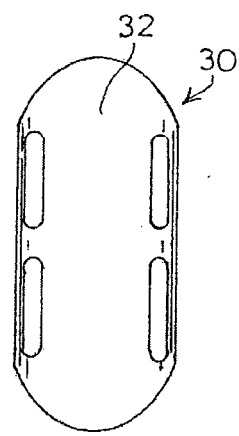
FIG. 2B is a top plan view of the agent-delivery device shown in FIG. 2A.
Figure 2C:
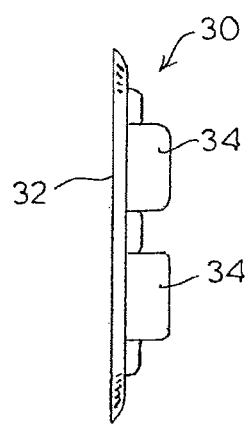
FIG. 2C is a side elevation view of the agent-delivery device shown in FIG. 2A.
Figure 2D:
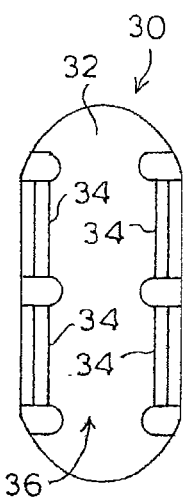
FIG. 2D is a bottom plan view of the agent-delivery device shown in FIG. 2A.
Figure 2E:
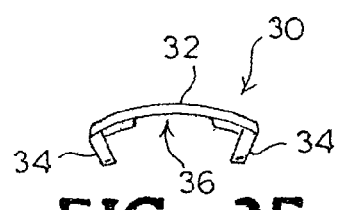
FIG. 2E is an end view of the agent-delivery device shown in FIG. 2A.
Figure 12:
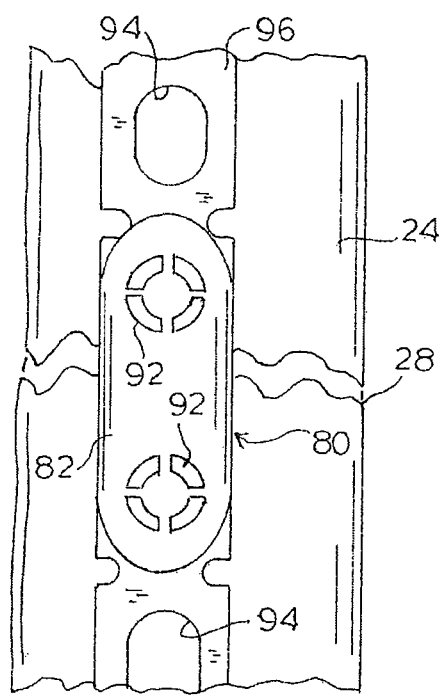
FIG. 12 is an elevation view of the agent-delivery device shown in FIG. 11.

In use, the agent-delivery device 80 is aligned such that the inserts 86 correspond to holes 94 in the fracture fixation plate 96, as shown in FIGS. 11 and 12. The agent-delivery device 80 is then pressed in a direction toward the fracture fixation plate 96. The flanges 90 on the legs 88 engage the plate 96 adjacent the holes 94 and, because of the space between each leg, the legs 88 flex inwardly during the downward movement of the device against the fracture fixation plate 96. The inserts 86 thus advance into and through the holes 94 in the fracture fixation plate 96. Once the flanges 90 clear the holes 94 on the other side of the plate 96, the legs 88 of the inserts 86 flex outwardly and the flanges 90 engage the plate. The flanges 90 thus serve to anchor the inserts 86 securely against the fracture fixation plate 96 and prevent any movement of the agent-delivery device 80 relative to the plate. In this manner, the agent-delivery device 80 may be fixed to a portion of the fracture fixation plate 96 on either side of a fracture or surgically altered bone. It is understood that multiple means of anchorage to the holes in the plate are suitable, including expandable collets that may allow for anchorage to a wide range of hole diameters.

Figure 13:
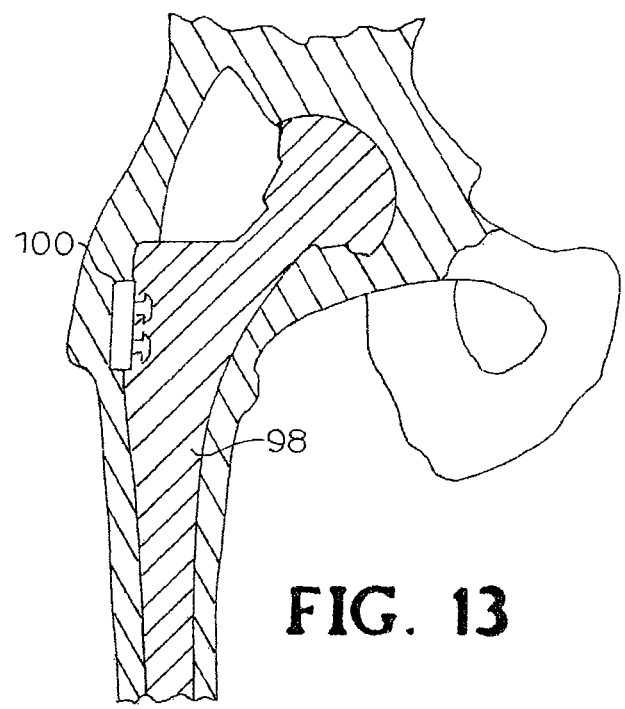
FIG. 13 is an elevation view of a total hip joint arthroplasty implant including the agent-delivery device as shown in FIGS. 10a-10E.

The snap-in agent-delivery device 80 may also be affixed to a long-term implant such as a femoral component 98 of a total hip replacement device, as shown in FIG. 13. In this application, the femoral component 98 of the device may be slightly modified to incorporate an undercut pocket 100 for the snap-in device inserts 86. It is understood that other attachment mechanisms may be used including, but not limited to, a key-way for a slotted insert and the like. In the case of joint arthroplasty, the therapeutic agent may, for example, prevent infection or may accelerate bony ingrowth/ongrowth needed for long-term anchorage in the bone.

Figure 14:
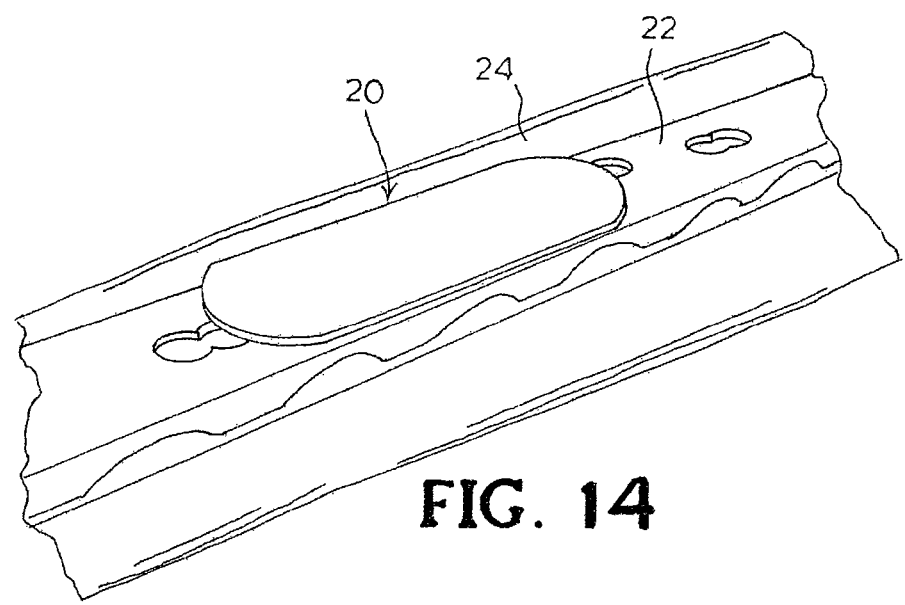
FIG. 14 is perspective view of an embodiment of an agent-delivery device adapted to a fracture fixation plate.

In one embodiment, the agent-delivery device may be configured to securely affix to a fracture fixation plate. In one aspect, adhesives are used to secure the agent-delivery device 10 to the fixation device surface (FIG. 14). The adhesives may be absorbable or non-absorbable. Suitable adhesives for use with the agent-delivery device include cyanoacrylates. Examples of cyanoacrylates include, for example, alkyl ester cyanoacrylates, alkyl ether cyanoacrylates or mixtures thereof. For example, suitable adhesives can be prepared by mixing suitable quantities of an alkyl alpha cyanoacrylate such as 2-octyl alpha-cyanoacrylate with one of butyl lactoyl cyanoacrylate (BLCA), butyl glycoloyl cyanoacrylate (BGCA), isopropyl glycoloyl cyanoacrylate (IPGCA), ethyl lactoyl cyanoacrylate (ELCA), and ethyl glycoloyl cyanoacrylate (EGCA). Such mixtures may range from ratios of about 90:10 to about 10:90 by weight, preferably about 75:25 to about 25:75 by weight such as from about 60:40 to about 40:60 by weight.

In one aspect, the agent-delivery device can include a pressure sensitive adhesive on at least a portion of at least one surface, to assist in initial placement of the agent-delivery device on the desired portion of the fixation device. In other aspects, the agent-delivery device includes a pressure sensitive adhesive on at least one side in combination with one or more mechanical securement means, such as herein disclosed. The pressure sensitive adhesive can be covered by a suitable release layer or liner, if desired, to preserve the adhesiveness of the material until time of use. The pressure sensitive adhesive may also include a therapeutic agent.

Figure 15:
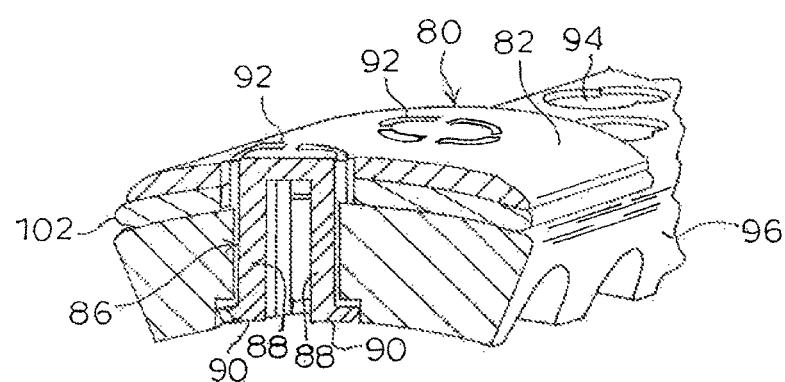
FIG. 15 is a cross-section view of the agent-delivery device shown in FIGS. 10A-10E adapted to an internal fracture fixation plate and including a carrier.
Figure 16:
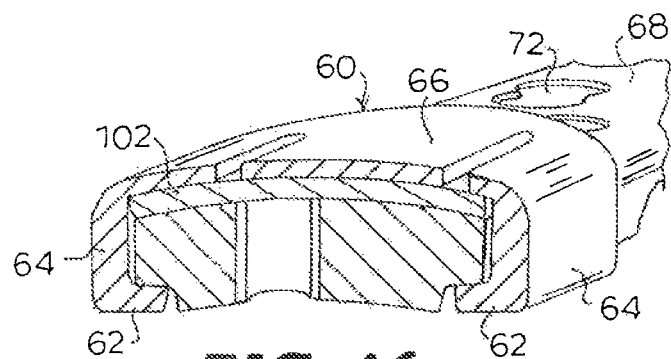
FIG. 16 is a cross-section view of the agent-delivery device shown in FIG. 7 adapted to an internal fracture fixation plate and including a carrier.

Referring to FIGS. 15 and 16, a therapeutic agent-eluting sponge 102 may be placed between the base portion of the agent-delivery device and the fracture fixation plate. This feature is applicable to both the snap-in and slide-on embodiments of the agent-delivery device 60, 80. Openings 104 through the base portion in this and other embodiments provide pathways so that the therapeutic agent within the sponge 102 is immediately available to the localized area to deliver the desired therapeutic effect. As described in detail herein, the eluting sponge 102 may include therapeutic agents that are designed to be released from the sponge 102 at a delayed, sustained, or controlled rate into the surrounding area to achieve a particular delivery profile and provide maximum benefit to the patient. Alternatively, a highly viscous gel or a cross-linked gel may be used as the carrier material to fill the cavity and for local delivery of the therapeutic agent.

FIGS. 15 and 16 also show minor modifications to the fracture fixation plate for accommodating the agent-delivery device. Specifically, the fracture fixation plates may be modified to add a small countersink or a slot/chamfer on the underside of the plate to receive the correspondingly configured agent-delivery device.

Figure 17:
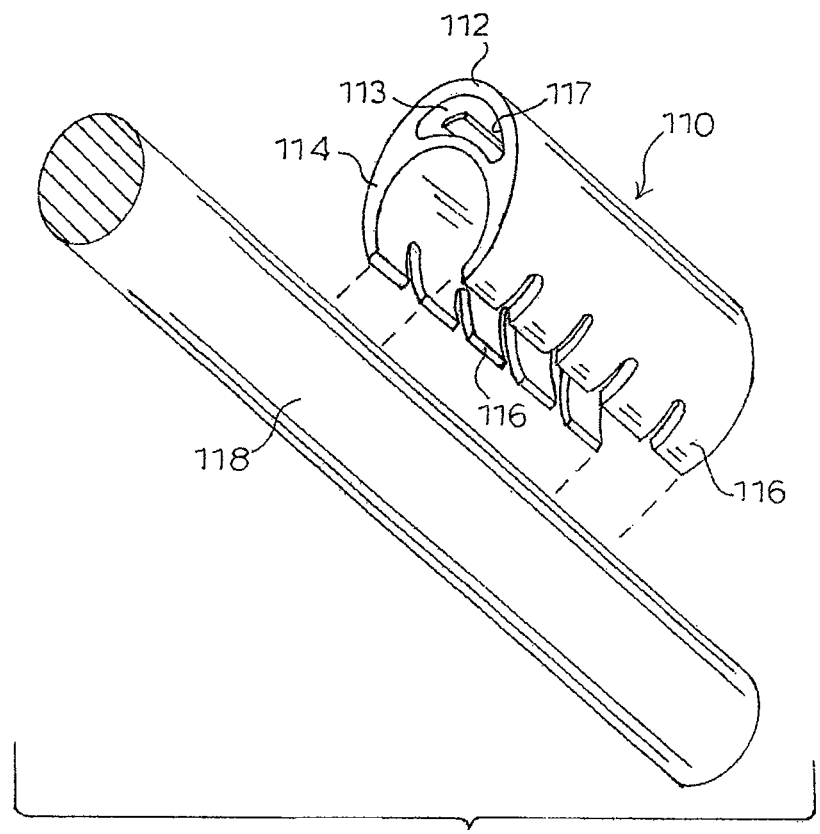
FIG. 17 is an exploded perspective view of an embodiment of an agent-delivery device and a rod for a spinal fusion construct.

Another embodiment of a snap-on agent-delivery device is shown in FIG. 17 and generally designated at 110. This embodiment of the agent-delivery device 110 comprises a compartment portion 112 and a sleeve 114. The compartment portion 112 defines an open-ended cavity 113 extending along at least a portion of the compartment 112 for accommodating a therapeutic agent-eluting sponge (not shown). The compartment 112 has one or more slots 115 therein that open into and extend along the length of the cavity 113. The sleeve 114 includes a first side and a second side, each side having a series of opposed arcuate fingers 116.

Figure 19:
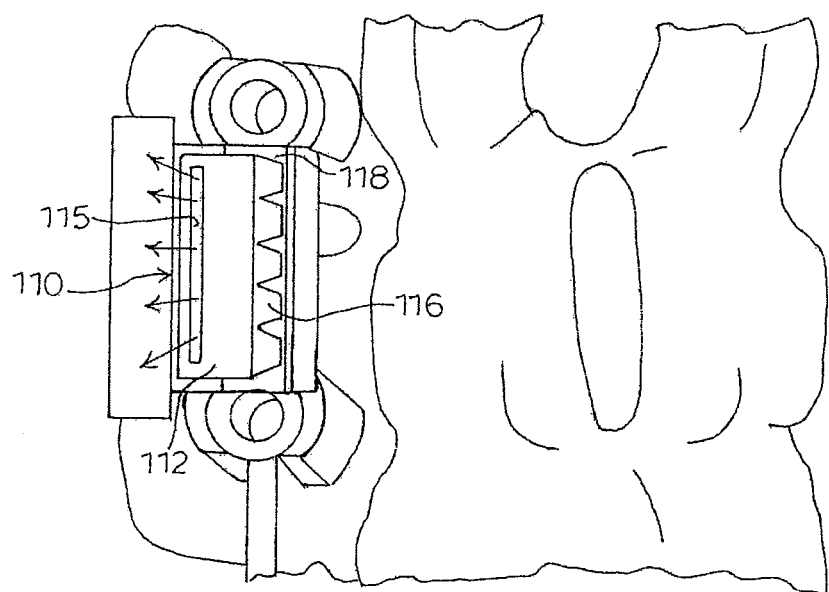
FIG. 19 is an elevation view of the agent-delivery device shown in FIG. 17 adapted to the rod of a spinal fusion construct in an installed position on vertebrae.
Figure 18:
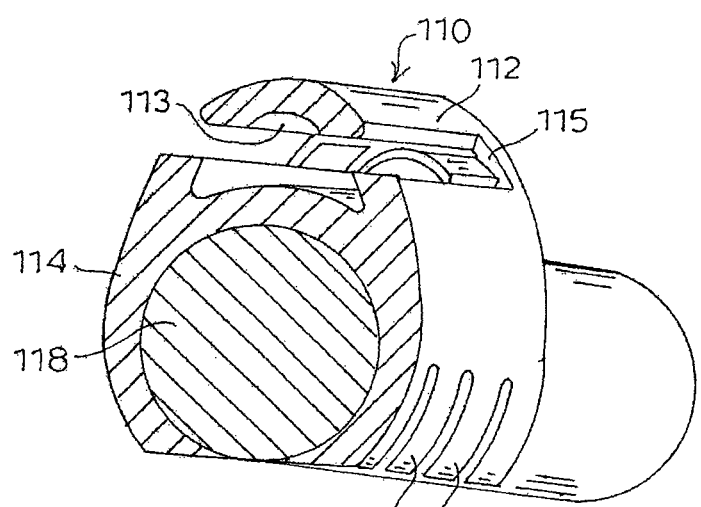
FIG. 18 is a cross-section view of the agent-delivery device shown in FIG. 17 adapted to the rod.
Figure 20A:
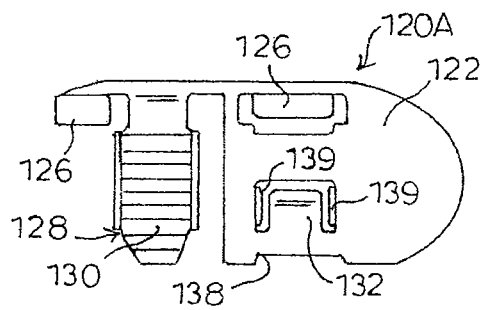
FIG. 20A is a top plan view of a two-part embodiment of an agent-delivery device.
Figure 20D:
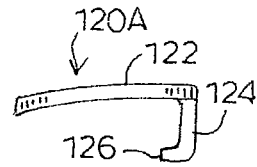
FIG. 20D is an end elevation view of the agent-delivery device shown in FIG. 20A.
Figure 20B:
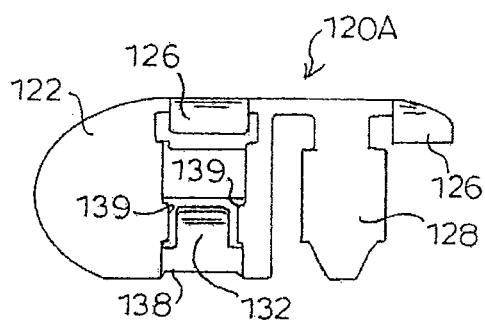
FIG. 20B is a bottom plan view of the agent-delivery device shown in FIG. 20A.
Figure 20E:
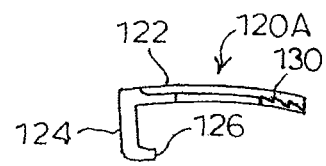
FIG. 20E is another end elevation view of the agent-delivery device shown in FIG. 20A.
Figure 20F:
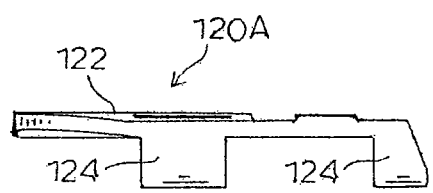
FIG. 20F is another side elevation view of the agent-delivery device shown in FIG. 20A.
Figure 20C:
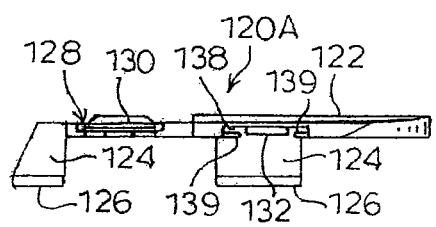
FIG. 20C is a side elevation view of the agent-delivery device shown in FIG. 20A.

The agent-delivery device 110 is configured to snap-on to a rod 118 used for spinal fixation (FIG. 18). Referring to FIG. 19, in use, the rod 118 is set in place within the spinal column at the site of the spinal instrumentation, for example to accelerate bone healing or in order to treat (or prevent) infection. The user places the agent eluting sponge or drug eluting gel within the cavity 113 of the compartment portion 112. The sleeve 114 is then snapped onto a portion of the length of the rod 118 so that the fingers 116 are gripping the circumference of the rod 118 and hold the sleeve 114 in place such that the compartment portion 112 may be positioned in close proximity to the area in which a bony fusion is desired, such as adjacent vertebrae. Therapeutic agents within the sponge are released via the slots 115 in the compartment 112 or through the open ends 117 of the compartment. In this manner, the agents are released into the area of the fracture site, or fusion construct site, to deliver the desired therapeutic value.

FIGS. 20A-24 show an embodiment of an adjustable snap-on device, generally designated at 120A, 120B. The body portions 120A, 120B are generally mirror images of one another and include a base portion 122 and depending side walls 124 and inwardly directed flanges 126 at the edges of the side walls 124. Each body portion 120A, 120B also has an inwardly extending tongue 128 in the plane of the base portion 122. Each tongue 128 has transverse ridges 130 along its upper surface. A tab 132 is spaced longitudinally from the tongue 128 on each body portion 120A, 120B and is integral with the base portion 122. Each tab 132 has ridges 134 on its lower surface. The inner side walls 124 of each body portion 120A, 120B define an opening 136 for receiving the tongue 128.

Figure 21:
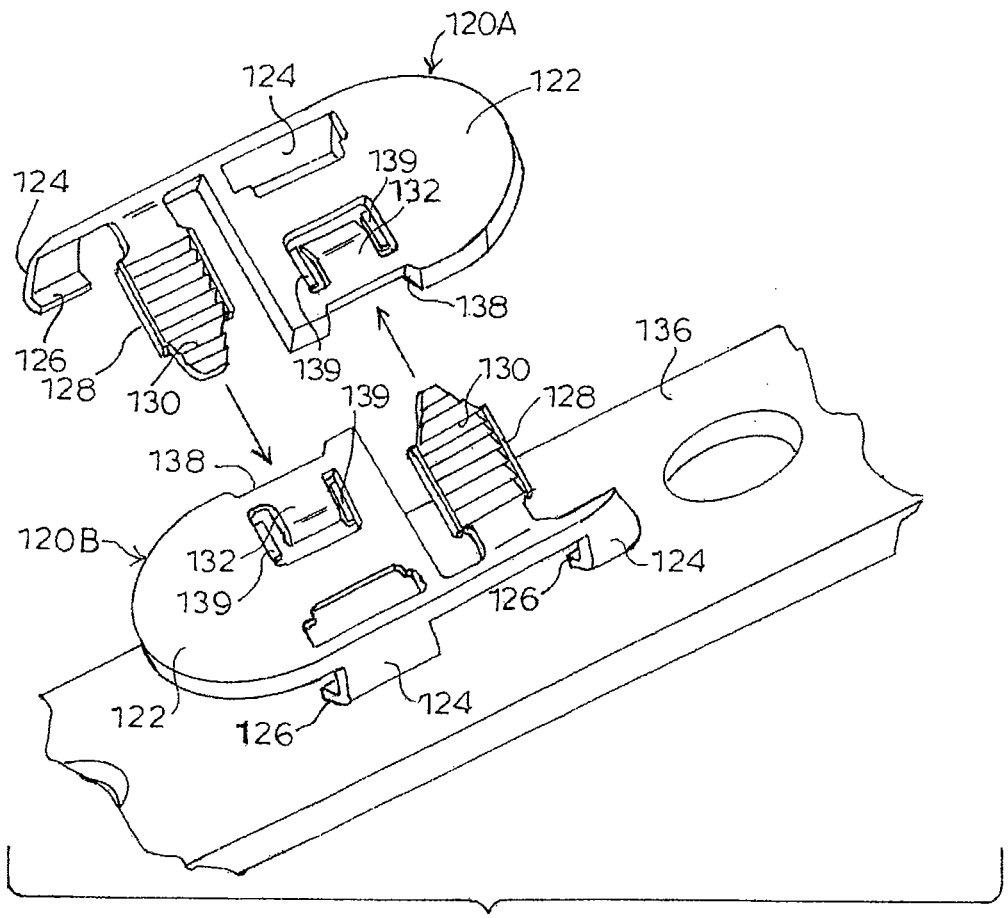
FIG. 21 is an exploded perspective view of the of the agent-delivery device shown in FIGS. 20A-20F.
Figure 22:
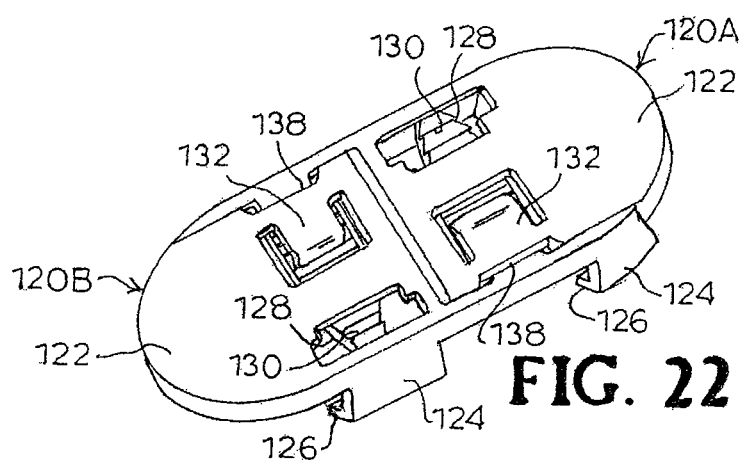
FIG. 22 is a top perspective view of the of the agent-delivery device shown in FIG. 21 when assembled.
Figure 23:
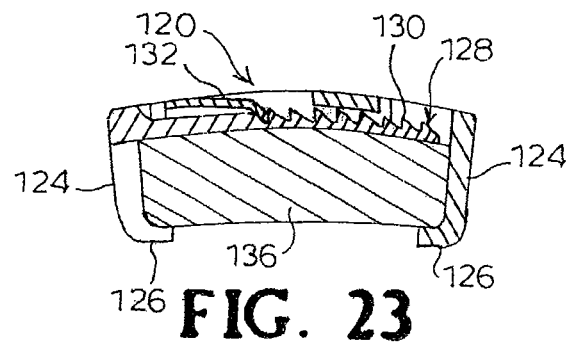
FIG. 23 is a cross-section view of the agent-delivery device shown in FIG. 21 in place on a fracture fixation plate.
Figure 24:
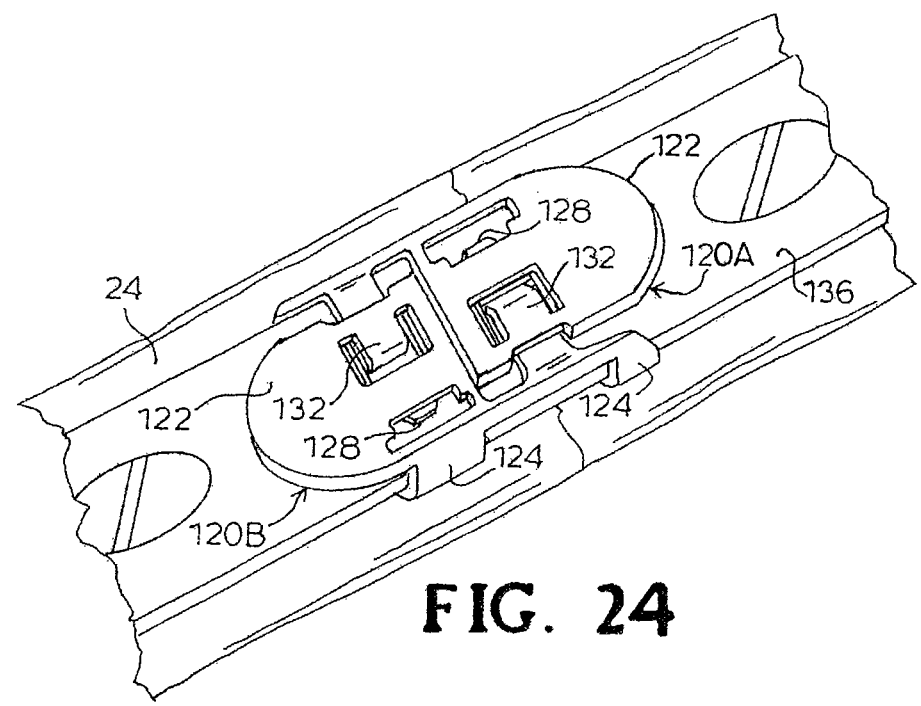
FIG. 24 is a top perspective view of the of the agent-delivery device shown in FIG. 21 in place on a fracture fixation plate secured to a bone fracture.

As shown in FIG. 21, the tongues 128 are aligned with the corresponding opening 136 in the body portions 120A, 120B and advanced towards one another in the direction of the arrows. The ridges 130 on the tongues 128 engage the ridges 134 on the tab 134 for securely joining the two body portions 120A, 120B. As seen in FIG. 22, the configuration of the joined body portions 120A, 120B of the agent-delivery device 120 generally now corresponds to the shape of previous embodiments of the device described herein.

In use, the body portions 120A, 120B of the agent-delivery device 120 can be brought together and secured adjacent the upper surface and sides of a fracture fixation plate 136. The body portions 120A, 120B are advanced towards one another such that the sides of the fracture fixation plate 136 are received in the slots 138 defined by the side walls 124, flanges 126 and lower surface of the base portion 122. As the body portions 120A, 120B are advanced towards one another, the ridges 130 on the tongues 128 engage the ridges 134 on the respective tabs 132 to form a secure fit on the fraction fixation plate 136. This arrangement can be seen in FIGS. 23 and 24.

It is understood that the sizes of the embodiments of agent-delivery device depicted herein are merely exemplary and that the size may vary as suitable for a particular indication. For example, the agent-delivery device may be sized to substantially cover a fracture fixation plate in order to ensure delivery of therapeutic agent locally to the entire area around the plate. Thus, the applicants do not intend to be limited to the relative sizes of the agent-delivery devices shown herein. Similarly, the same goal can be accomplished by using a plurality of agent-delivery devices along the length of the fracture fixation plate, or other medical implant, as desired.

In one embodiment, an agent-delivery device may define a reservoir adapted to contain a therapeutic agent effective in obtaining a desired local or systemic physiological or pharmacological effect. The reservoir may be integral with or separable from the agent-delivery device. The reservoir, or a portion of the reservoir, may comprise a permeable material which is contained in a substantially impermeable portion of the device. For example, the reservoir may comprise an impermeable outer layer around a permeable material comprising the agent, allowing diffusion of the agent out of the reservoir. The impermeable portion of the reservoir may optionally contain pores of a size capable of providing a targeted delivery profile. The reservoir may comprise a carrier, such as a sponge or gel material, capable of absorbing or adsorbing or otherwise containing the therapeutic agent. A removable cover or lid may be adapted to be removed as desired to expose the carrier or a permeable portion of the reservoir. For example, a section of the impermeable outer layer of the reservoir may be configured for removal. The cover may be configured to be removed to introduce one or more agents to the reservoir, or immediately before or after adapting the agent-delivery device to the fixation device, for example, just prior to surgically implanting the fixation device.

An integral, resealable valve may be provided to allow the reservoir to be filled by a physician during a postoperative, outpatient procedure without surgical intervention. Filling of the reservoir may be accomplished by percutaneous injection through the valve into the reservoir. An external valve-location means may be provided to accurately locate the position of the valve among the surrounding tissue.

Figure 25:
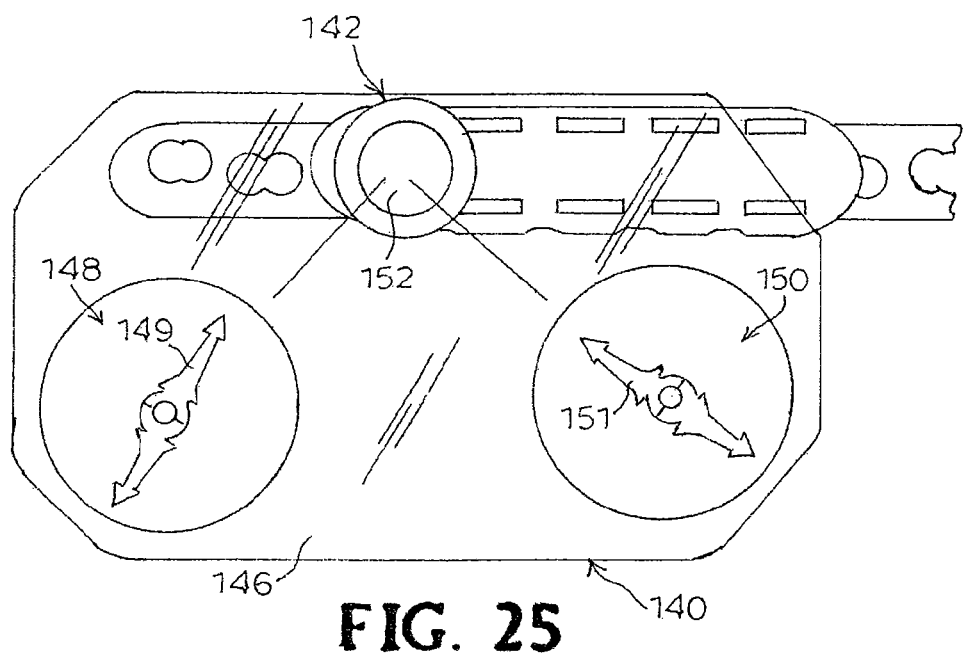
FIG. 25 is schematic top plan view of an embodiment of an agent-delivery device including a reservoir and valve and an external locator.

An embodiment of a resealable valve and valve locator combination is shown in FIG. 25, comprising an agent-delivery device including a reservoir and a locator, generally shown at 140. The agent-delivery device comprises a resealable valve 142 which is designed to operate with the external locator 140, allowing a surgeon to determine the position of the valve for post-operative injections to fill the reservoir with a desired therapeutic agent. The valve 142 is provided with indicia in the form of magnetically-responsive elements, such as magnets, although other metallic elements could be used provided they are magnetically-responsive, as well as any other means to signify the position of the valve which are capable of being determined by external locator devices.

The locator comprises a base 146, including a plurality of sensors 148, 150, each of which may comprise a magnetic compass needle. Each needle is allowed to freely orientate with either the north or south magnetic pole within a closed recess in the base 146. The sensors 148, 150 are spaced from one another such that when the locator 140 is maneuvered into position over the valve 142 the pair of north or south indicating needles 148, 150 orientate with one another and define a third point 152, shown by the target opening which indicates a true position of the valve 142. FIG. 25 shows the needles 148, 150 pointing toward the target 152 to signify the true location of the underlying valve 142. Thus, a physician (or nurse) is able to precisely locate the injection valve.

It is understood that the injection valve may be situated at a location remote from the medical implant, and the valve coupled with a fill tube feeding into the reservoir, whereby agent injected into the valve flows through the fill-tube into the reservoir.

A suitable arrangement of this type, including a resealable valve and locator means, is described in U.S. Pat. No. 5,146,933, the contents of which are hereby incorporated by reference in their entirety.

Figure 26:
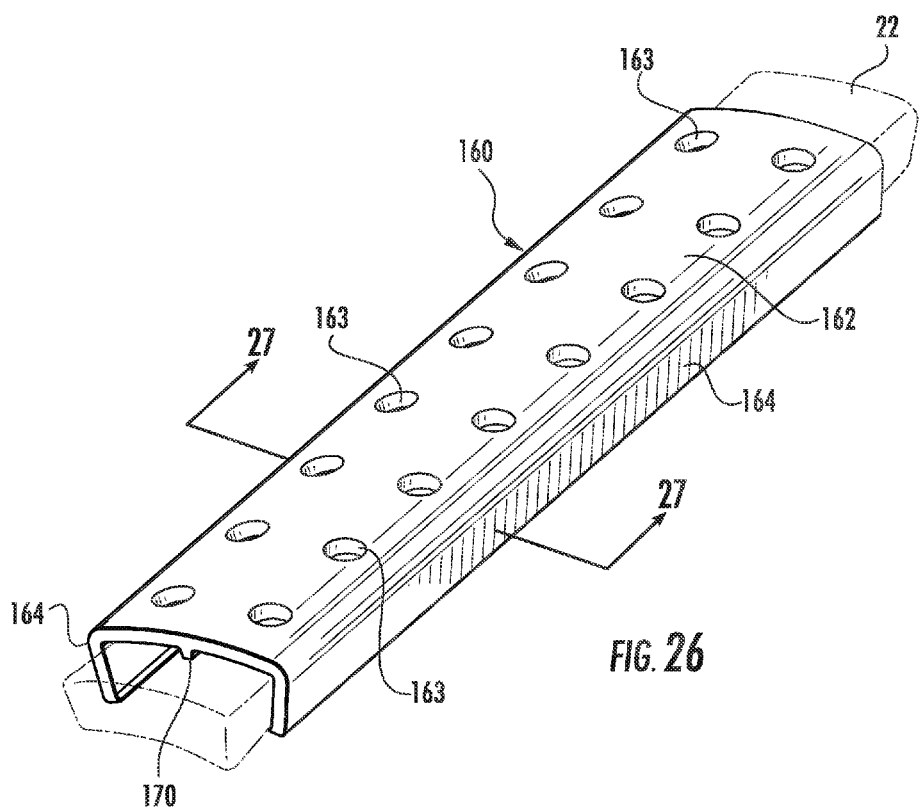
FIG. 26 is a perspective view of another embodiment of an agent-delivery device adapted to an internal fracture fixation plate.

Another embodiment of an agent-delivery device configured to adapt to a fracture fixation plate by sliding onto the medical implant is shown in FIGS. 26-29 and generally designated at 160. The agent-delivery device 160 is an elongated member having a substantially rectangular profile and comprises a major base portion 162 having a longitudinal axis and a plurality of openings 163 therethrough. The base portion 162 spans between generally planar side walls 164, or legs, depending from the longitudinal edges of each side of the base portion 162. Each of the side walls 164 terminates in longitudinal edges. The base portion 162 and the side walls 164 define an open longitudinal channel 166. The inner surface 168 of the agent-delivery device 160 has a central longitudinal ridge 170 or projection (FIG. 29). As shown in FIGS. 26-28, the side walls 164 are angled inwardly relative to the base portion 162. The terminal edges of the side walls 164 include a continuous inwardly directed shoulder 172 extending along the length of the associated side walls. The agent-delivery device 160 is sized and shaped such that the distance between the inner surface of the side walls 164 and the distance between the inner surface 168 of the base portion 162 and the shoulders 172 is slightly larger than width and thickness, respectively, of the fracture fixation plate 22.

Referring to FIGS. 26 and 28, the agent-delivery device 160 having this configuration is adapted to a generally planar rectangular fracture fixation plate 22 by sliding the device 160 onto the end of the plate. The agent-delivery device 160 may be moved to a desired location along the length of the plate 22 manually or by an instrument such as facilitated by a blunt tamp. As best seen in FIG. 28, the ridge 170 engages the upper surface of the plate 22 for providing space between the inner surface 168 of the agent-delivery device 160 and the fracture fixation plate 22 for disposing a carrier, such as a sponge or gel. The openings 163 through the base portion 162 provide pathways so that the therapeutic agent within the carrier is immediately available to the localized area to deliver the desired therapeutic effect. Alternatively, the device may be snapped onto the plate 22, the sidewalls being sufficiently flexible to deflect outward prior to securely affixing to the plate at the shoulders 172.

FIGS. 30-34 illustrate another embodiment of a slide-on agent-delivery device, generally designated at 180. This embodiment 180 is similar to the embodiment of the agent-delivery device shown in FIGS. 4 and 5 and described above. The agent-delivery device 180 is an elongated member having a substantially rectangular profile and comprises a major base portion 182 having a longitudinal axis and a plurality of openings 183 therethrough spaced along the edges. Side walls 184 depend generally perpendicularly along the length of the edges of the base portion 182. Tabs 186 are punched into the side walls 184 along their length. The tabs 186 extend inwardly substantially in a direction toward the inner surface 188 of the base portion 182. The distal ends of the tabs 186 are tapered forming opposed pointed terminal edges which are disposed substantially parallel with respect to the side walls 184. Short transverse ridges 190 are spaced longitudinally along the inner surface 188 of the base portion 182. The ridges 190 extend inwardly in a direction substantially normal to the plane of the side walls 184.

Figure 30:
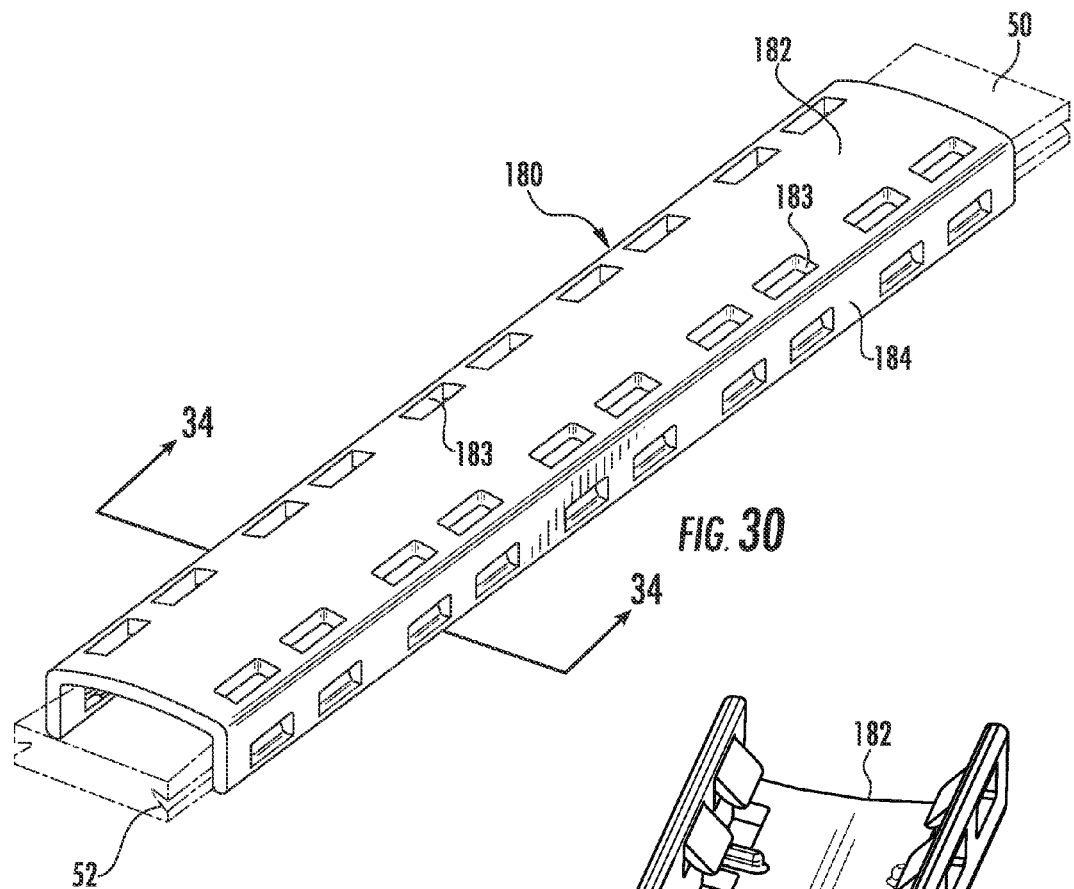
FIG. 30 is a top perspective view of another embodiment of an agent-delivery device adapted to an internal fracture fixation plate.
Figure 31:
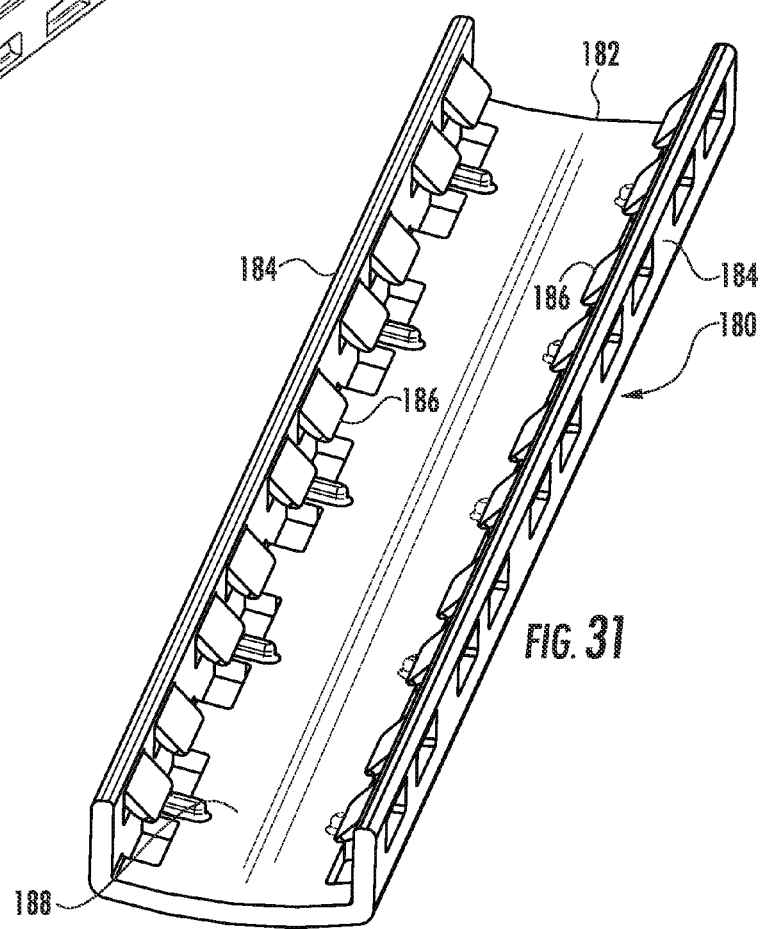
FIG. 31 is a bottom perspective view of the agent-delivery device shown in FIG. 30.
Figure 35:
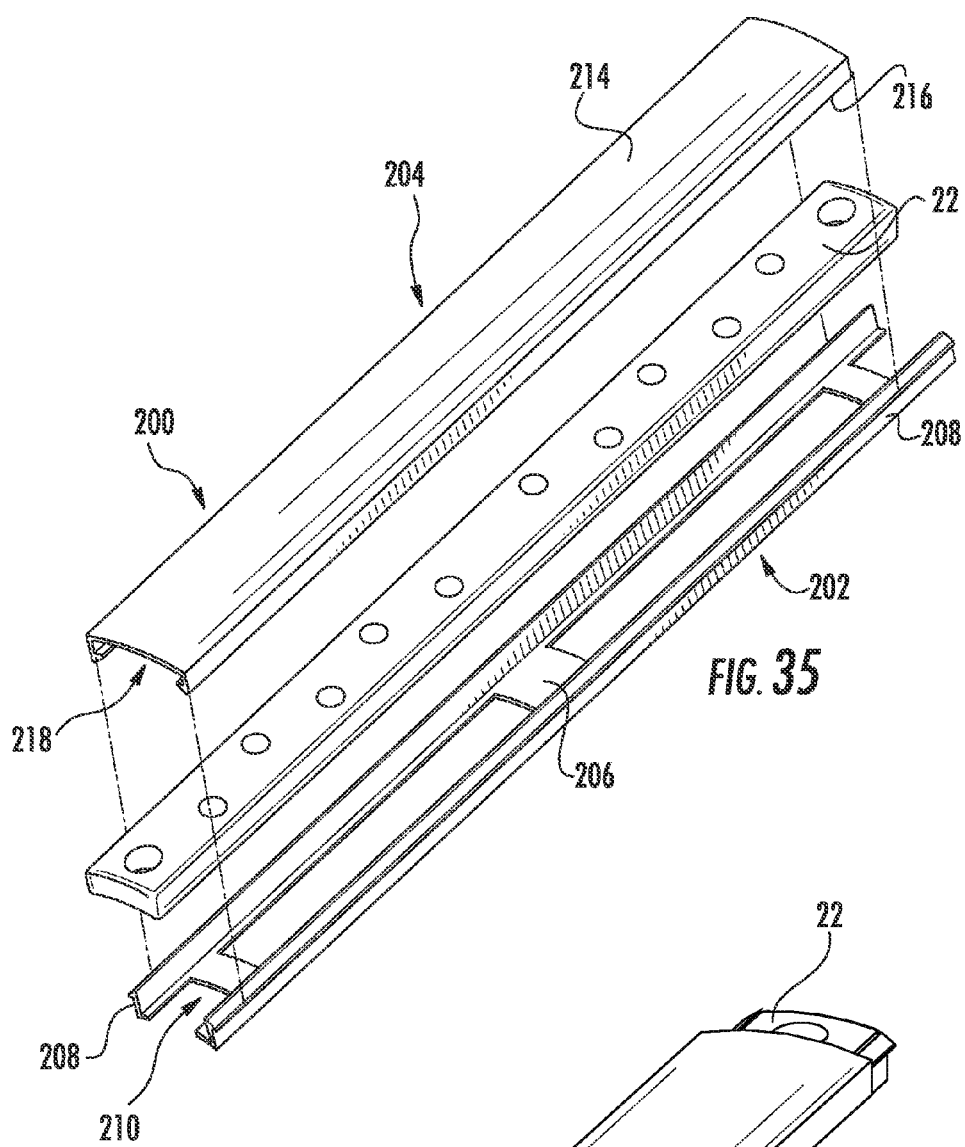
FIG. 35 is an exploded perspective view of a two-part embodiment of an agent-delivery device and an internal fracture fixation plate.

Referring to FIGS. 30 and 33, in use, the agent-delivery device 180 is adapted by sliding the device onto the end of the fracture fixation plate 50 such that the distal ends of the tabs 186 are slidably received in the longitudinal grooves 52 in the sides of the fracture fixation plate 50 for securing the agent-delivery device 180 to the plate 50. The agent-delivery device 180 may be advanced along the length of the plate 50 manually or by an instrument such as facilitated by a blunt tamp. It is understood that the agent-delivery device 180 may be adapted to the fracture fixation plate 50 prior to securing the plate to the bone. It is also understood that the agent-delivery device may be alternatively secured to the plate 50 from a direction perpendicular to the surface, snapping into place. As best seen in FIG. 33, the ridges 190 engage the upper surface of the plate 50 for providing space between the inner surface 188 of the agent-delivery device 180 and the fracture fixation plate 50 for disposing a carrier. The openings 183 through the base portion 182 provide pathways so that the therapeutic agent within the carrier is immediately available to the localized area to deliver the desired therapeutic effect.

An embodiment of an multiple-component agent-delivery device configured to "snap-on" at a desired location on a fracture fixation plate is shown in FIGS. 35-38 and generally designated at 200. The agent-delivery device 200 comprises an inner member 202 and an outer member 204. The inner member 202 includes a web portion 206 and generally planar side walls 208 extending generally perpendicularly from along the length of the edges of the web portion 206. The web portion 206 together with the side walls 208 define an open longitudinal channel 210. The terminal edges of the side walls 208 of the web portion 206 include a continuous outwardly directed flange 212 extending along the length of the associated side walls 208. The inner member 202 is sized and shaped such that the distance between the inner surface of the side walls 208 and the distance between the inner surface of the web portion 206 and the upper surface of the flanges 212 is slightly larger than width and thickness, respectively, of the fracture fixation plate 20.

The outer member 204 comprises a base portion 214 and generally planar side walls 216 depending generally perpendicularly along the length of the edges of the base portion 214. The base portion 214 and the side walls 216 define an open longitudinal channel 218. The terminal edges of the side walls 216 of the base portion 214 include a continuous inwardly directed flange 220 extending along the length of the associated side walls 216.

Figure 36:
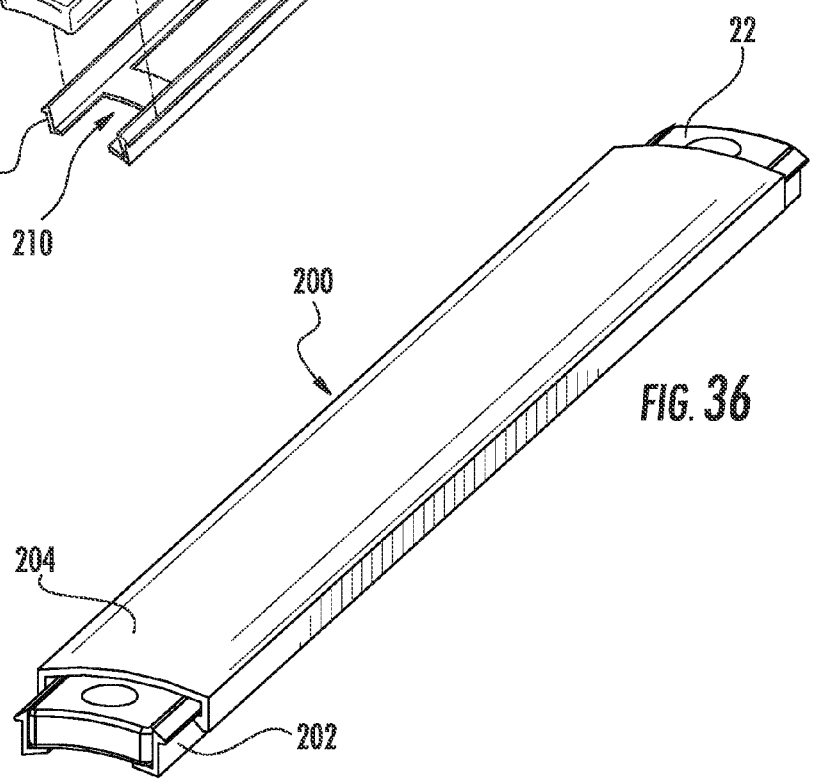
FIG. 36 is a perspective view of the agent-delivery device shown in FIG. 35 adapted to the internal fracture fixation plate.

In use, the inner member 202 of the agent-delivery device 200 receives the fracture fixation plate 20. The outer member 204 is aligned in registry over the inner member 202 and then advanced in a direction toward the fracture fixation plate 20. The flanges 212, 220 on the side walls 208, 216 engage and, because of the angular upper surface of the flanges (FIG. 38), the side walls 216 of the outer member 204 flex outwardly during the movement of the outer member 204 toward the fracture fixation plate 20. The flanges 220 on the outer member 204 eventually pass over the flanges 212 of the inner member 202. The side walls of the outer member 204 flex inwardly and engage the flanges 212 of the inner member 202 for capturing the fracture fixation plate (FIG. 36). In this manner, the agent-delivery device 200 may be fixed around a portion of the fracture fixation plate 200 on either side of a fracture or surgically altered bone.

Figure 47:
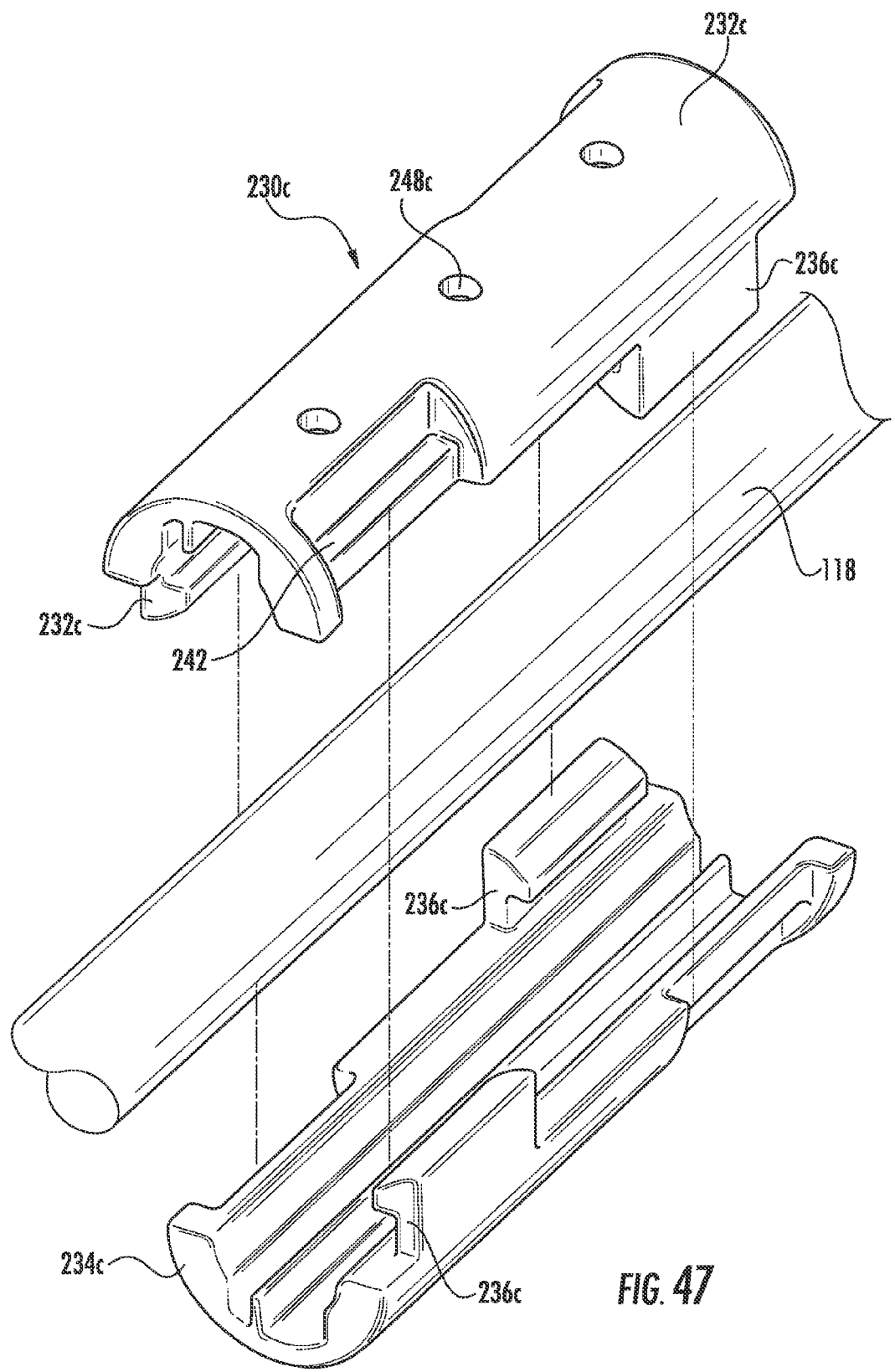
FIG. 47 is an exploded perspective view of another two-part embodiment of an agent-delivery device and a rod for a spinal fusion construct.
Figure 48:
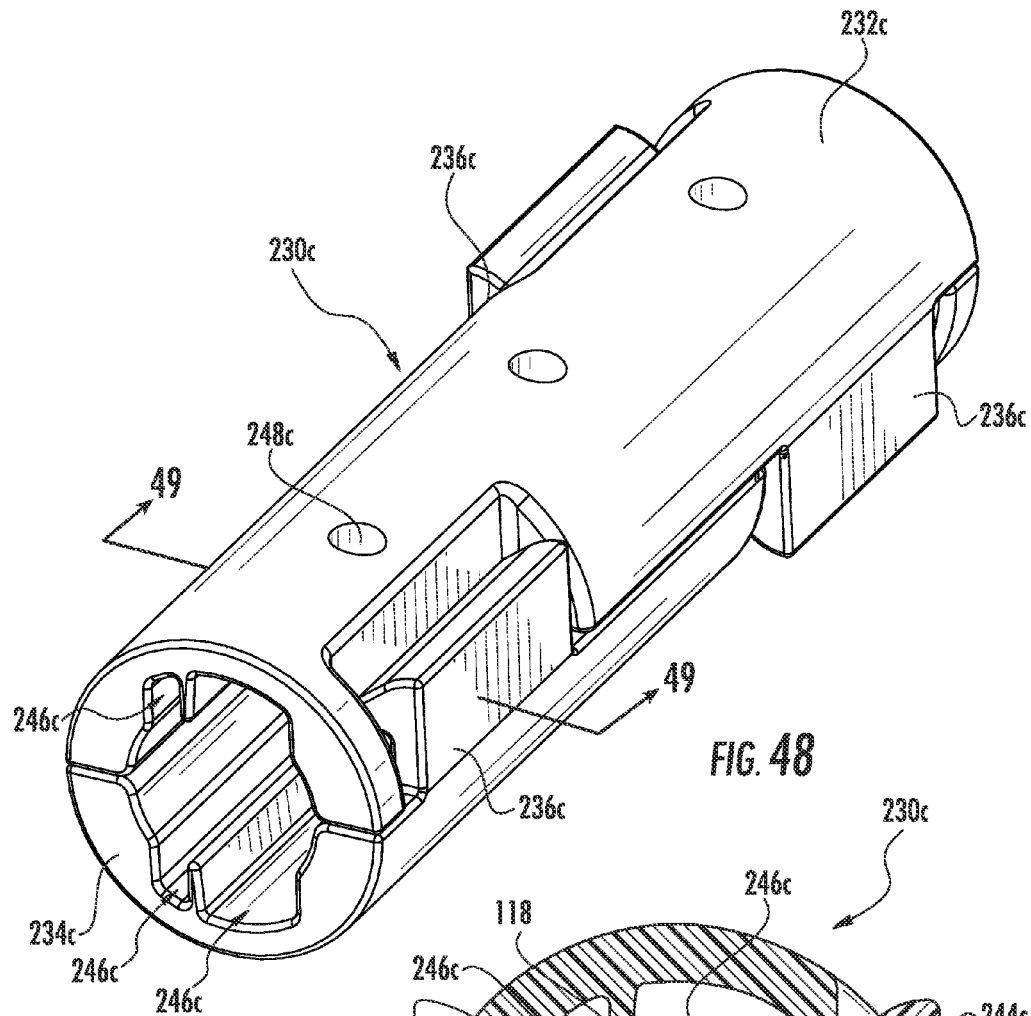
FIG. 48 is a perspective view of the agent-delivery device shown in FIG. 47 adapted to receive the rod when assembled.
Figure 49:
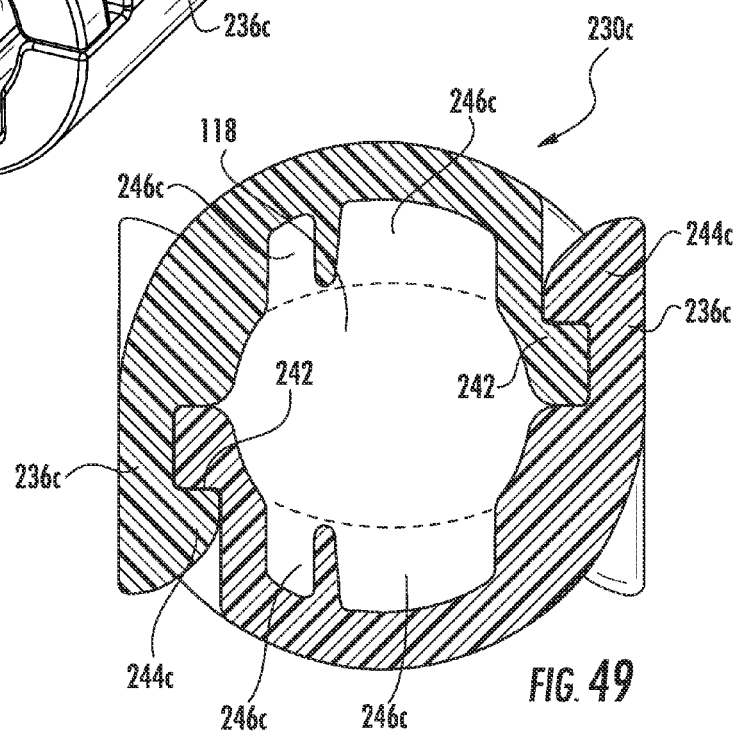
FIG. 49 is a cross-section view of the agent-delivery device shown in FIG. 47 adapted to receive the rod taken along line 49-49.

FIGS. 39-49 show three additional embodiments of a two-piece snap-on agent-delivery device, generally designated at 230a, 230b and 230c. Each embodiment 230a, 230b, 230c comprises a first body portion 232a, 232b, 232c and a second body portion 234a, 234b, 234c, which are substantially mirror images of one another, respectively. Flanges 236a, 236b, 236c extend from the opposite corners of each body portion. In the first two embodiments 230a, 230b shown in FIGS. 39-46, the side walls 238a, 238b at the other opposed corners of each body portion define slots 240a, 240b having an opening for receiving the flanges 236a, 236b. Referring to FIGS. 47-49, shoulders 242 are formed on the outer surface of the body portions for securing the flanges 236c.

Figure 39:
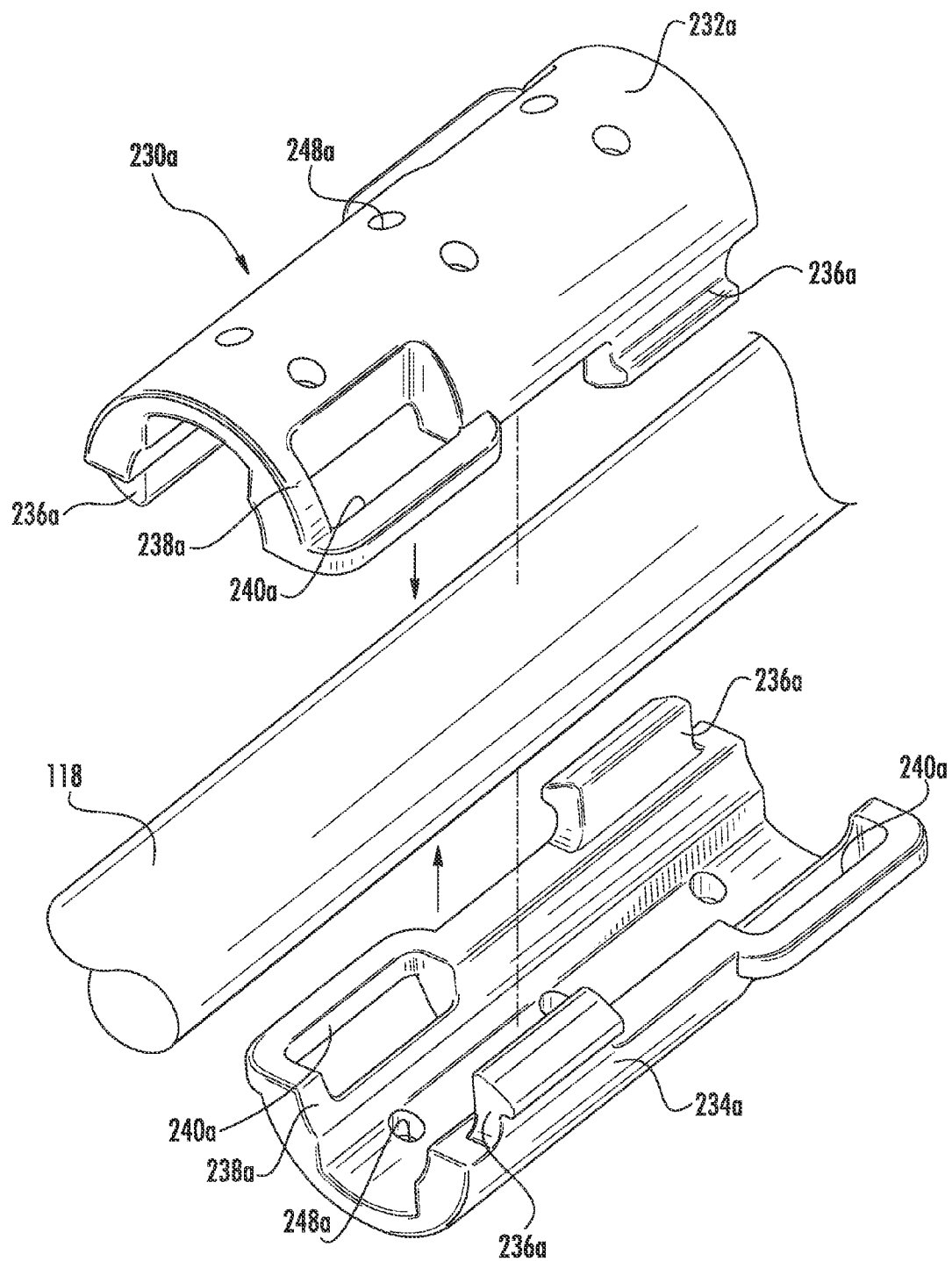
FIG. 39 is an exploded perspective view of a two-part embodiment of an agent-delivery device and a rod for a spinal fusion construct.
Figure 43:
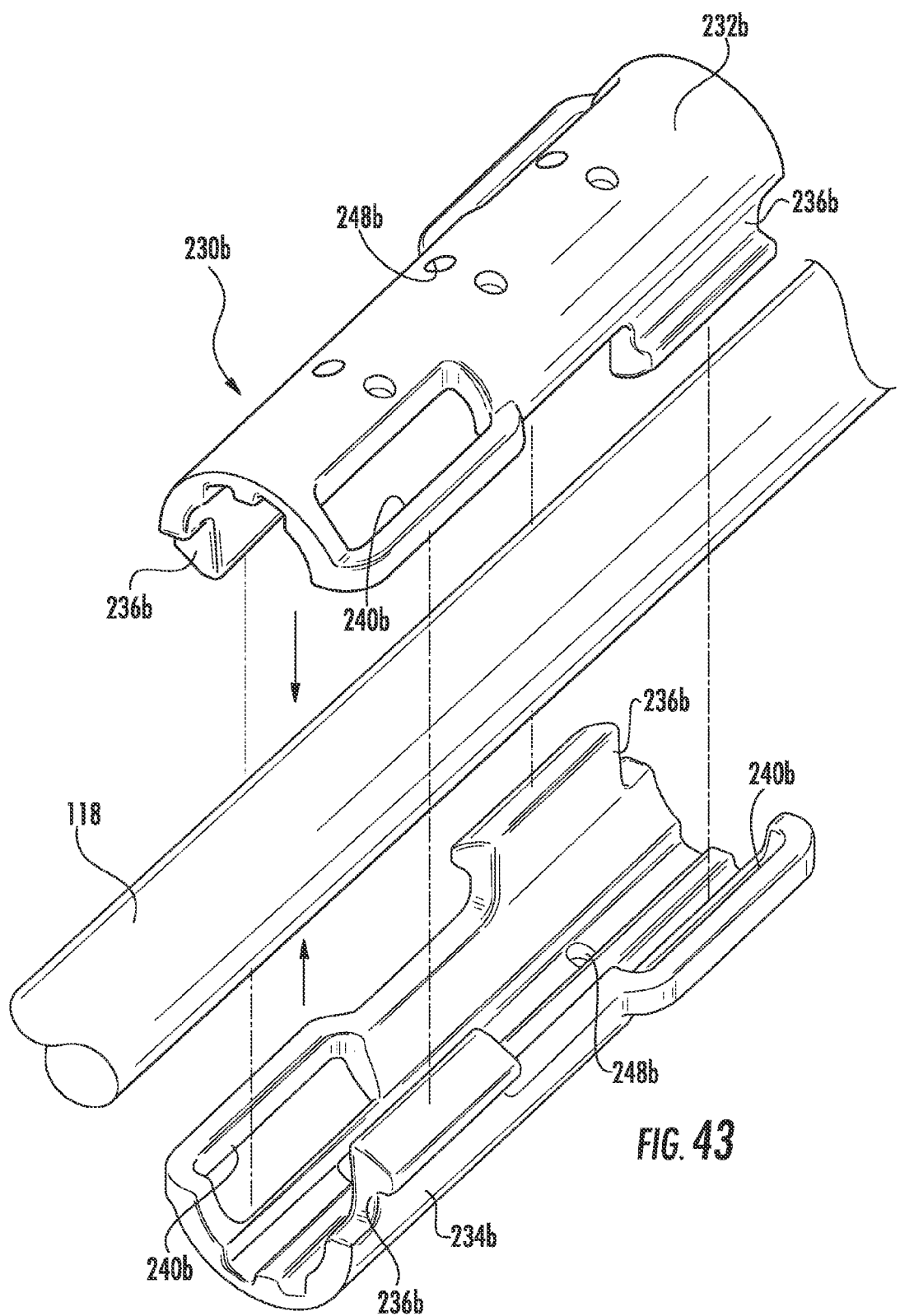
FIG. 43 is an exploded perspective view of another two-part embodiment of an agent-delivery device and a rod for a spinal fusion construct.

In use, the agent-delivery devices 230a, 230b, 230c are configured to snap-on to the rod 118 used for spinal fixation (FIG. 17) or long bone fracture fixation using intra-medullary nails or rods (not shown). As shown in FIGS. 39 and 43, the body portions are positioned such that the flanges 236a, 236b are aligned with the corresponding slots 240a, 240b in the body portions and advanced towards one another in the direction of the arrows until the flanges are received in the slots 240a, 240b. The flanges 236a, 236b of the first two embodiments are provided with outwardly directed lips 244a, 244b. The lips 244a, 244b on the flanges 236a, 236b extend through the slots 240a, 240b and engage the outer edges of the side walls 238a, 238b defining the respective slots 240a, 240b for securely joining the first and second body portions to form a secure fit of the agent-delivery device 230a, 230b on the rod 118 (FIGS. 40 and 44). Referring to FIGS. 47-49, the flanges 236c of the third embodiment of the agent-delivery device 230c are provided with inwardly directed lips 244c. The lips 244c engage the shoulders 242 formed on the outer surface of the body portions for securing the first and second body portions 232c, 234c together around the rod 118.

As shown in FIGS. 41, 45 and 49, each embodiment of the agent-delivery device 230a, 230b, 230c defines a compartment portion 246a, 246b, 246c between the inner surface of the body portions and the rod 118. The defined compartment portions 246a, 246b, 246c are open-ended cavities extending along at least a portion of the compartment for accommodating a carrier. The body portions have one or more openings into the compartment along the length of each body portion. When the user places the carrier within the cavity of the compartment portion 246a, 246b, 246c, therapeutic agents are released via the openings 248a, 248b, 248c into the compartment or through the open ends of the compartment. In this manner, the agents are released into the area of the fracture site, or bony fusion construct site, to deliver the desired therapeutic value.

FIGS. 50-60 show embodiments of the agent-delivery device which are similar to the two-piece snap-on design. However, in these embodiments, the pieces are longitudinally hinged along one side for movement between an open position and a closed position. In one embodiment (FIGS. 50-54), the agent-delivery device, generally designated at 250, comprises a first body portion 252a and a second body portion 254a which are substantially mirror images of one another. The first and second body portions 252a, 254a are joined by a flexible hinge 256 along a common side. The free side of the first body portion 252a includes integral longitudinally spaced pins 258. The free side of the second body portion 254a has longitudinally spaced holes 260 positioned to receive the pins 258. In a second embodiment of the two-piece hinged agent-delivery device 270, shown in FIGS. 55-60, a first body portion 252b and a second body portion 254b are provided that define a different interior profile than in the first embodiment, but the two embodiments are otherwise similar. The pins 258 and holes 260 of the first embodiment are also replaced by longitudinally spaced flanges 272 with outwardly directed lips 273 and corresponding slots 274.

Figure 55:
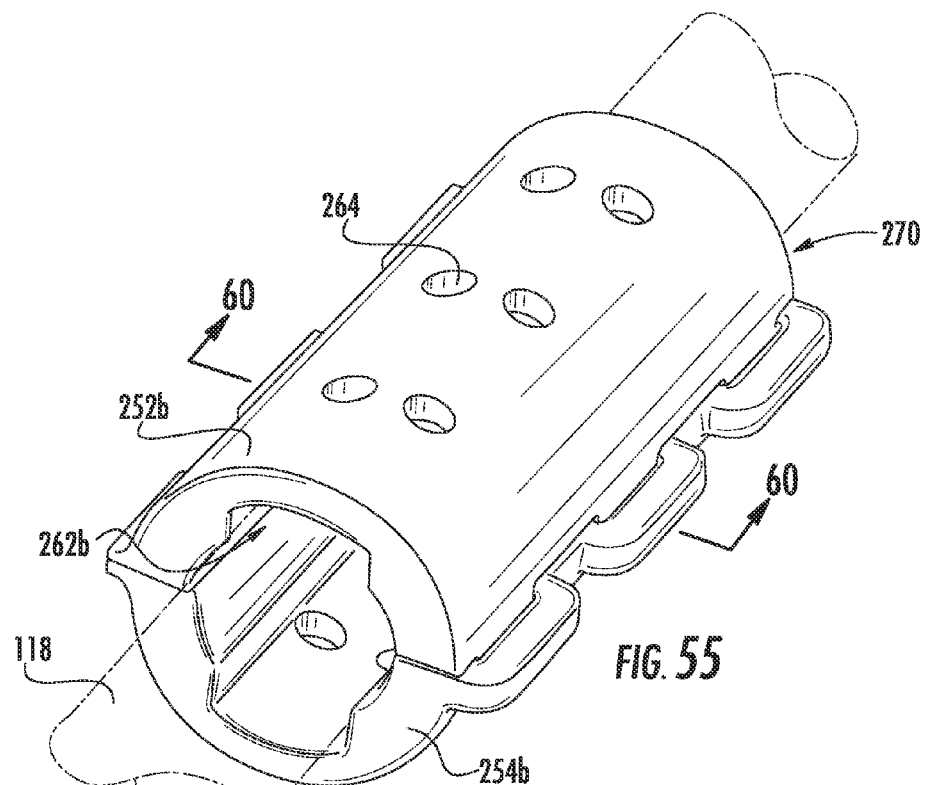
FIG. 55 is a perspective view of another embodiment of an agent-delivery device adapted to a rod for a spinal fusion construct.
Figure 56:
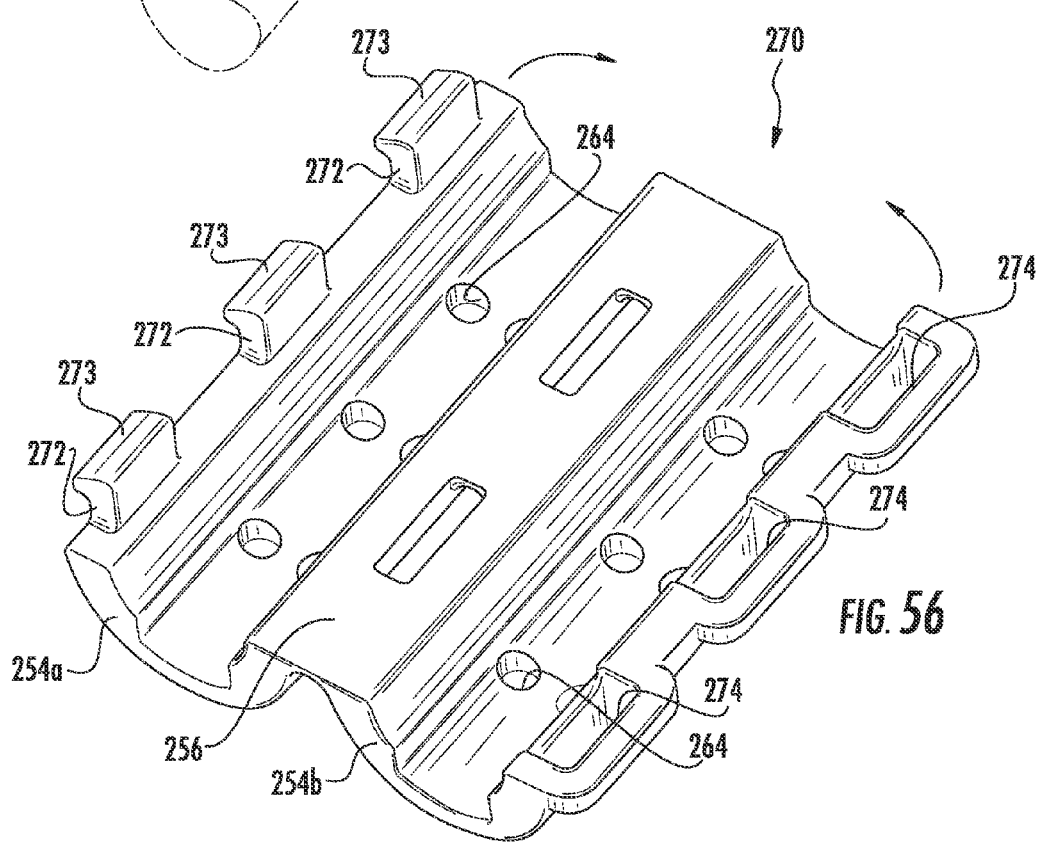
FIG. 56 is a perspective view of the agent-delivery device shown in FIG. 55 when in the open position.

In use, the agent-delivery devices 250, 270 are configured to snap-on to the rod 118 used for spinal fixation (FIG. 17) or long bone fracture fixation (using intra-medullary nails or rods) (figure not shown). The first and second body portions 252a, 254a, 252b, 254b are positioned adjacent the rod 118 and the free sides advanced towards one another in the direction of the arrows toward the closed position (FIGS. 51 and 56). The pins 258 and flanges 272 are received in the holes 260 and slots 274, respectively, to provide a secure fit on the rod 118 (FIGS. 50 and 55).

As shown in FIGS. 53, 54, 59 and 60, each embodiment of the two-piece hinged agent-delivery device 250, 270 defines a compartment portion 262a, 262b between the inner surface of the body portions 252, 254 and the rod 118. The defined compartment portions 262a, 262b are open-ended cavities extending along at least a portion of the compartment for accommodating a carrier. The body portions 252a, 252b, 254a, 254b have one or more openings 264 into the compartment along the length of each body portion. When the user places the carrier within the cavity of the compartment portion, therapeutic agents are released via the openings 264 into the compartment or through the open ends of the compartment. The compartment portion 262a, 262b may be positioned in close proximity to an area in which a bony fusion is desired, such as adjacent vertebrae.

FIGS. 61A-64 show a triple-hinged embodiment of an agent-delivery device, generally designated at 280. In this embodiment, a first body portion 282 comprises an inner half 284 and an outer half 286, which are hingedly connected to one another along their length. A second body portion 288 also comprises an inner half 290 and an outer half 292, which are hingedly connected to one another along their length. The outer edge of the inner half 290 of the second body portion 288 includes integral longitudinally spaced pins 294. The outer edge of the inner half 284 of the first body portion 282 has longitudinally spaced holes 296 positioned to receive the pins 294.

Figure 62:
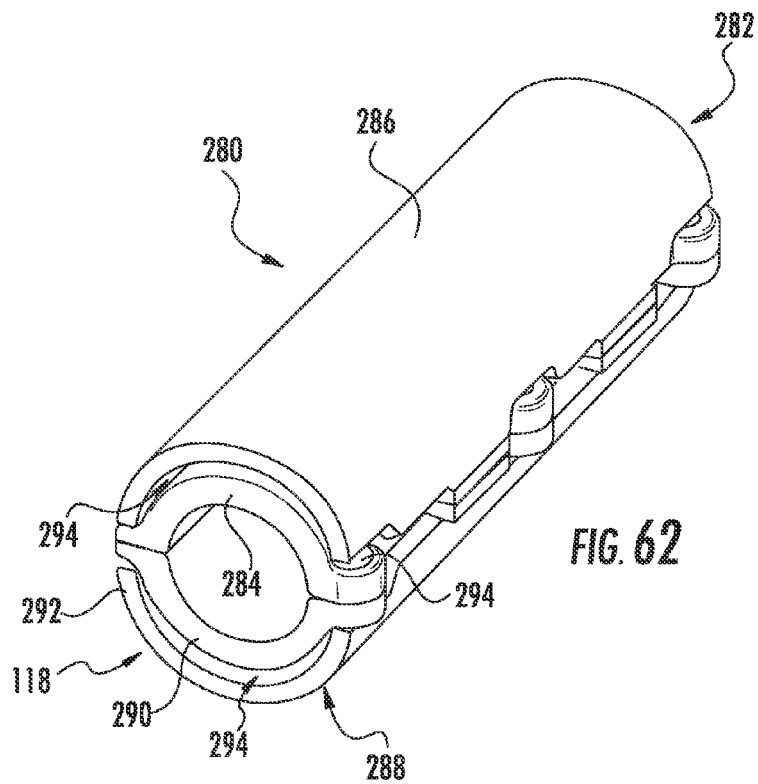
FIG. 62 is a perspective view of the agent-delivery device shown in FIG. 61 adapted to a rod for a spinal fusion construct when in a closed position.
Figure 63A:
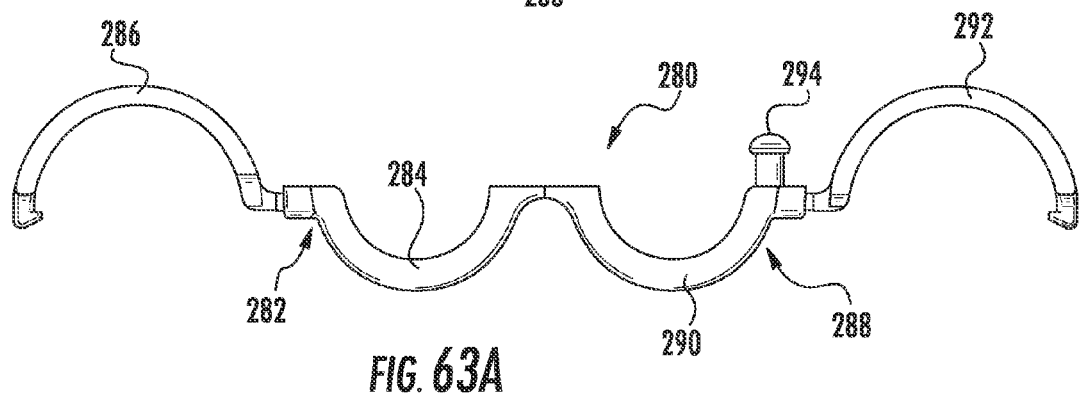
FIG. 63A is an end elevation view of the agent-delivery device shown in FIG. 62 when in the open position.
Figure 63B:
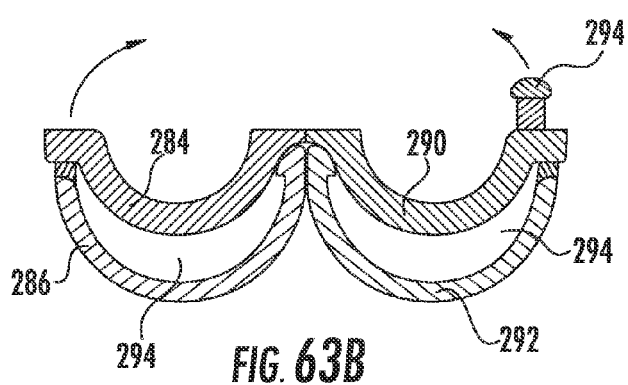
FIG. 63B is an end elevation view of the agent-delivery device as shown in FIG. 63A when in a partially closed position.

In use, the outer halves 286, 292 are folded into the inner halves 284, 290 along their hinged edges. The opposite body portions 282, 288 are then brought together around a rod 118, as described above. The first and second body portions 282, 288 are positioned adjacent the rod 118 and the free sides advanced towards one another in the direction of the arrows toward the closed position (FIG. 63B). The pins 294 are received in the holes 296 to provide a secure fit on the rod (FIG. 62).

Figure 64:
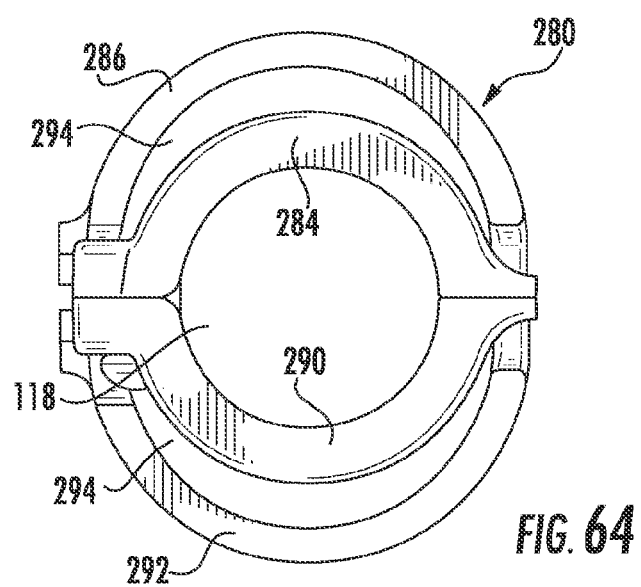
FIG. 64 is an end elevation view of the agent-delivery device shown in FIG. 62 adapted to receive the rod when in the closed position.

As shown in FIG. 64, when the triple-hinged embodiment of an agent-delivery device 280 is in a closed position, the halves of the body portions 282, 288 define compartment portions 294 between the inner halves 284, 290 and the outer halves 286, 292. The defined compartment portions 294 are open-ended cavities extending along at least a portion of the compartment for accommodating a carrier. When the user places the carrier within the cavity of the compartment portion 294, therapeutic agents are released through the open ends of the compartment. Openings through the outer halves 286, 292, similar to openings 248*a* in FIG. 39, may also be provided to release the therapeutic agents. The compartment portion 294 may be positioned in close proximity to an area in which a bony fusion is desired, such as adjacent vertebrae.

Another embodiment of a snap-on agent-delivery device for use with an intramedulary nail is shown in FIGS. 65-67 and generally designated at 300. This embodiment of the agent-delivery device 300 comprises a C-shaped sleeve 302 having a plurality of openings 304 spaced along and opening into the interior of the sleeve 302. The terminal ends of the sleeve 302 include a plurality of opposed arcuate fingers 306.

In use, the agent-delivery device 300 is configured to snap-on to a portion of the length of the intramedullary nail 308 used to be driven into a bone, such as the femur (FIG. 65). The user snaps the sleeve 302 onto the intramedullary nail 308 so that the fingers 306 are engage the circumference of the nail and hold the sleeve 302 in place. As seen in FIG. 67, the distal ends of the fingers 306 are shaped to correspond to longitudinal grooves 310 circumferentially spaced on the periphery of the intramedullary nail 308. Multiple devices 300 may be affixed to the implant 308 as required to deliver one or more therapeutic agents.

Figure 68:
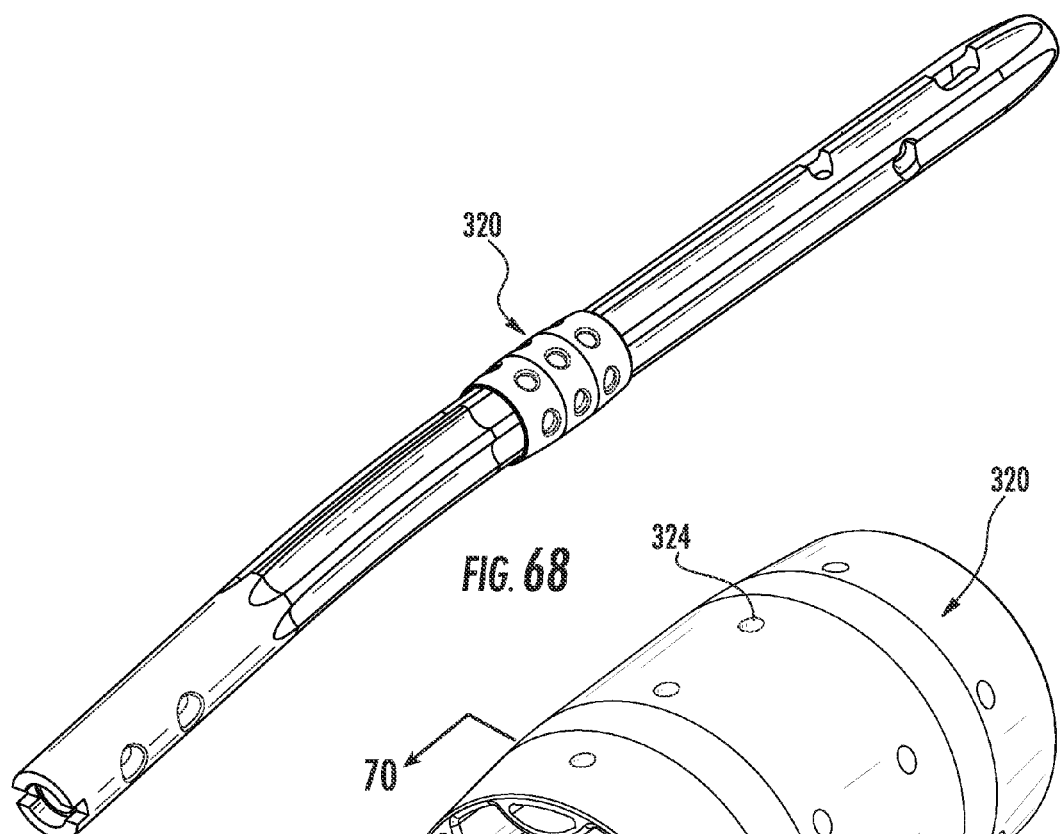
FIG. 68 is a perspective view of an embodiment of an agent-delivery device adapted to an intermedulary nail.
Figure 69:
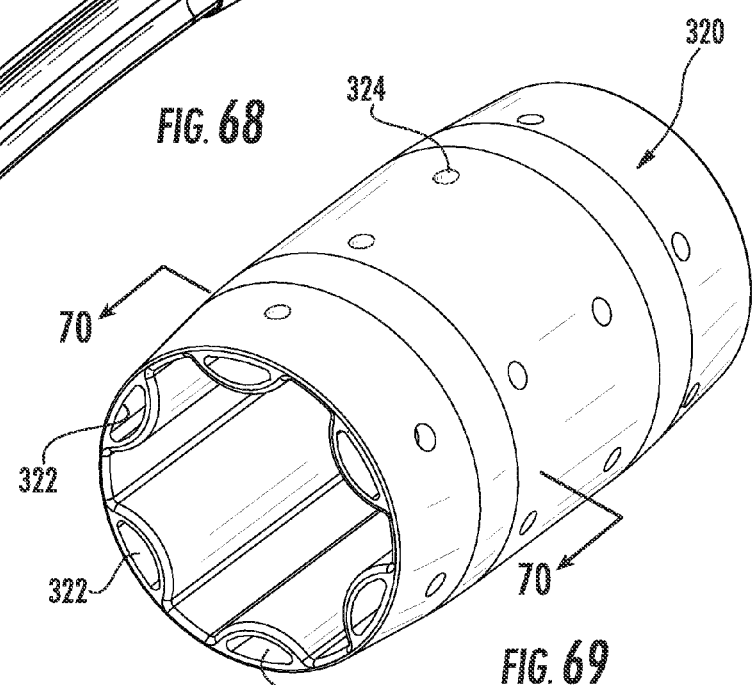
FIG. 69 is a perspective view of the agent-delivery device shown in FIG. 68.
Figure 70:
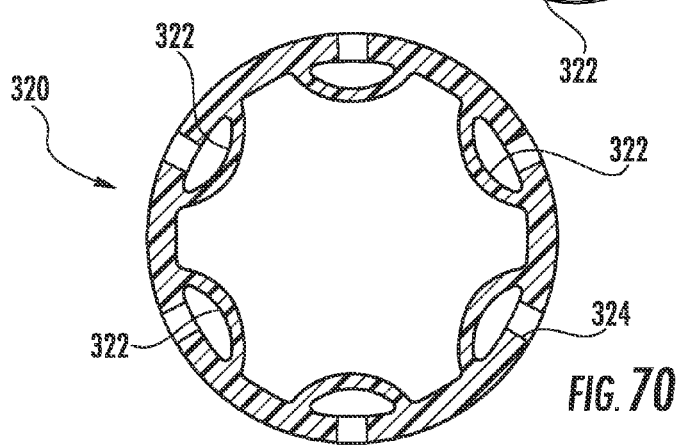
FIG. 70 is a cross-section view of the agent-delivery device shown in FIGS. 68 and 69 taken along line 70-70 adapted to the intermedulary nail.

Another embodiment of a slide-on agent-delivery device for use with the intramedullary nail 308 is shown in FIGS. 68-70 and generally designated at 320. In this embodiment the agent-delivery device 320 is a substantially cylindrical sleeve as best shown in FIG. 69. The agent-delivery device 320 comprises a plurality of longitudinal compartments 322 circumferentially spaced around the inner surface of the sleeve. Each compartment 322 defines an open-ended cavity for accommodating a carrier.

In use, the agent-delivery device 320 is configured to slide-on to the intramedullary nail 308 (FIG. 68). The user places the carrier within the compartment portions 322. The sleeve is then slid onto a portion of the length of the intramedullary nail 308, the interior surface gripping the circumference of the nail and holding the sleeve in place. The intramedullary nail is then set in place within the bone, for example the femur, to accelerate bone healing or in order to treat (or prevent) infection. Therapeutic agents within the carrier are released through the open ends of the compartments 322 and also via the outlet holes 324 as shown in FIG. 70. In this manner, the agents are released into the area of the fracture site, or fusion construct site, to deliver the desired therapeutic value.

Figure 71:
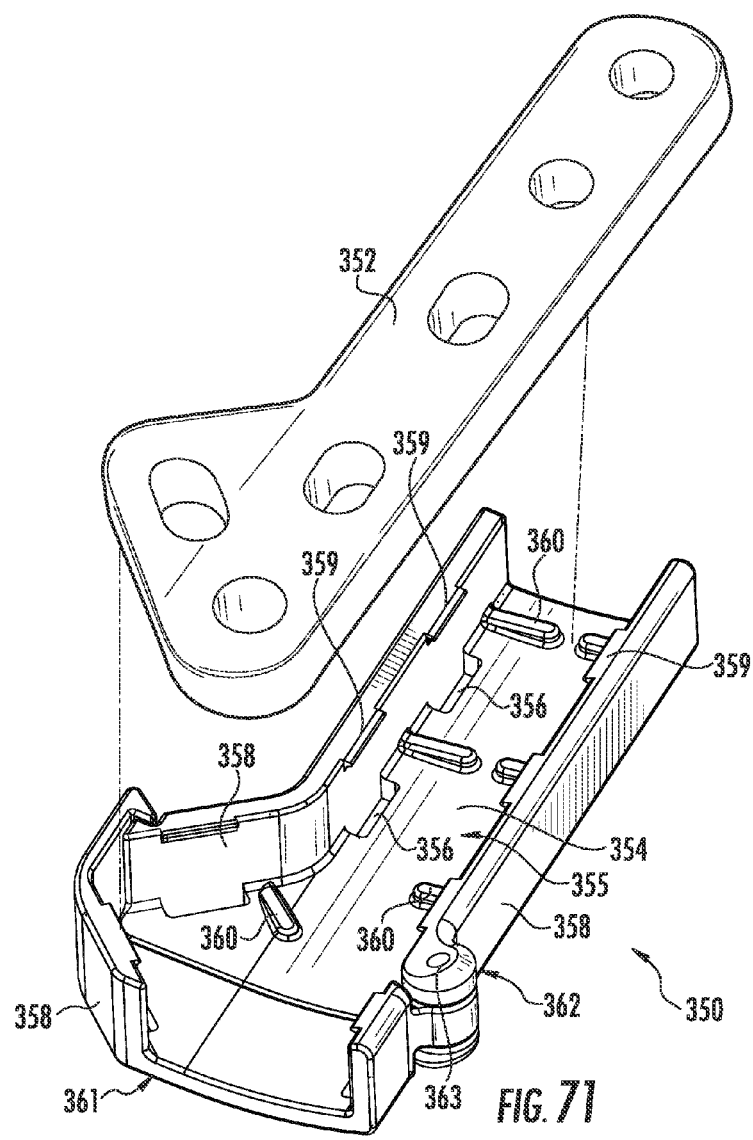
FIG. 71 is an exploded perspective view of another embodiment of an agent-delivery device adapted in a closed position to an internal fracture fixation plate.
Figure 72:
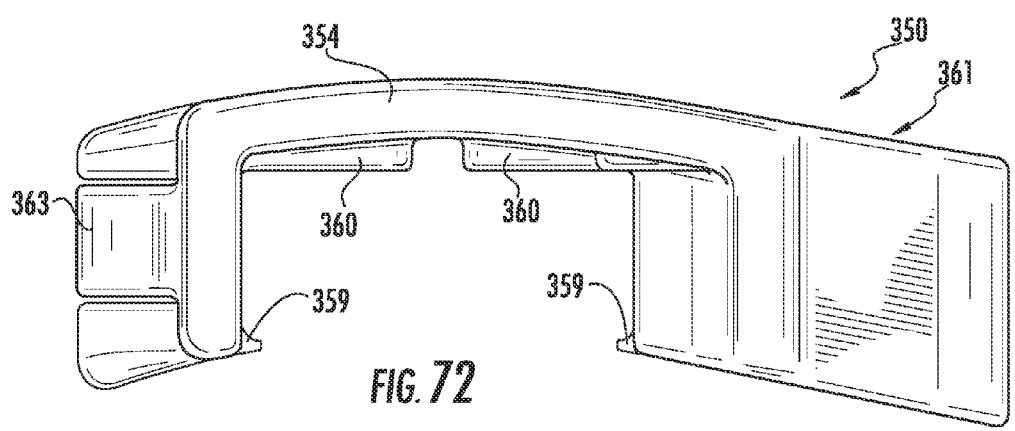
FIG. 72 is an end elevation view of the agent-delivery device shown in FIG. 71.

FIGS. 71-75 illustrate another embodiment of a snap-on agent-delivery device, generally designated at 350. This embodiment of the agent-delivery device 350 has particular application in veterinary orthopedics. Referring to FIG. 71, the agent-delivery device 350 is an elongated member having a profile substantially corresponding to a fracture fixation plate 352. The device 350 comprises a major base portion 354 having a longitudinal axis and a plurality of openings 356 spaced along the edges. Side walls 358 depend generally perpendicularly along the length of the edges of the base portion 354. Flanges 359 are spaced along the length of the edges of the side walls 358. The flanges 359 extend inwardly in a direction substantially perpendicular to the side walls 358 (FIG. 72). The distal ends of the flanges 359 are disposed substantially parallel with respect to the side walls 358. Short transverse ridges 360 are spaced longitudinally along the inner surface 355 of the base portion 354. The ridges 360 extend inwardly in a direction substantially normal to the plane of the side walls 358. The agent-delivery device is segmented in two portions 361, 362 at a hinged connection 363 that facilitates adapting the device 350 to the fracture fixation plate 352.

Figure 73:
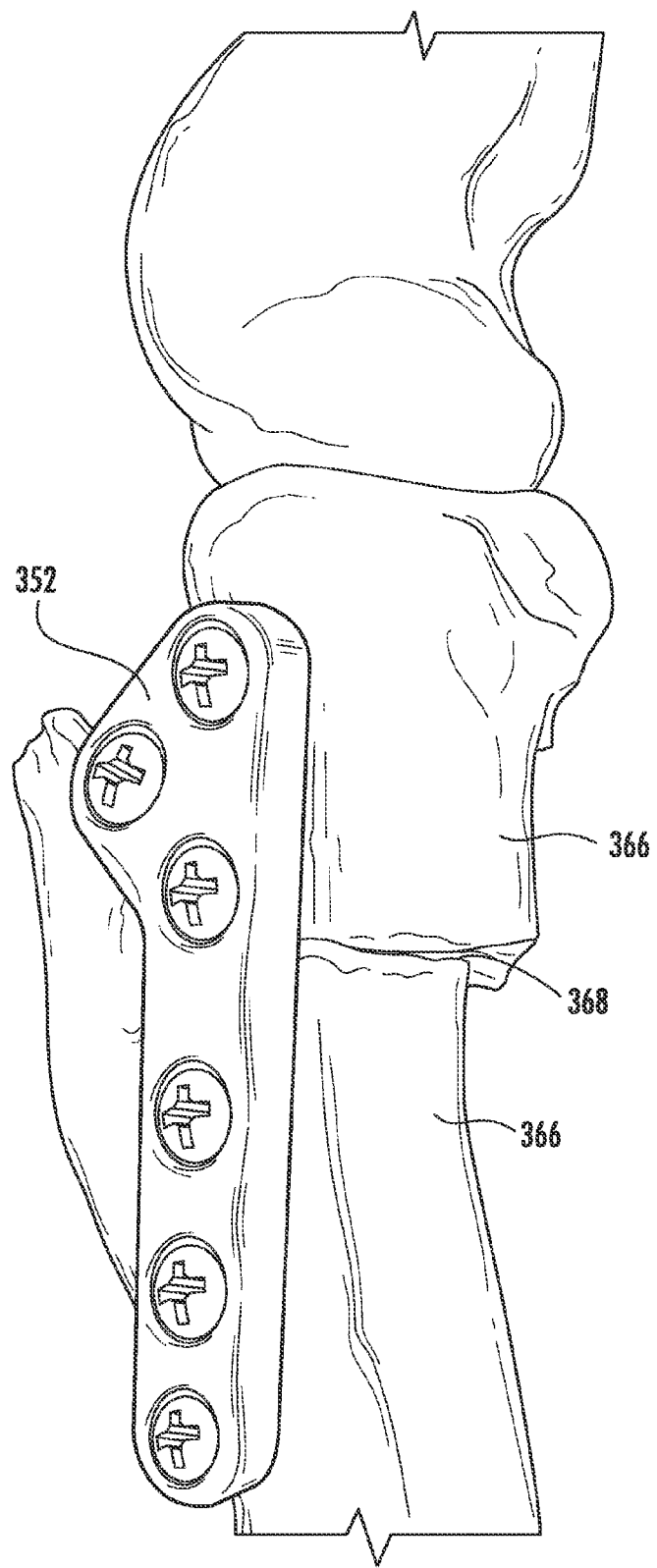
FIG. 73 is a perspective view of the internal fracture fixation plate secured to a bone fracture or osteotomy location.
Figure 74:
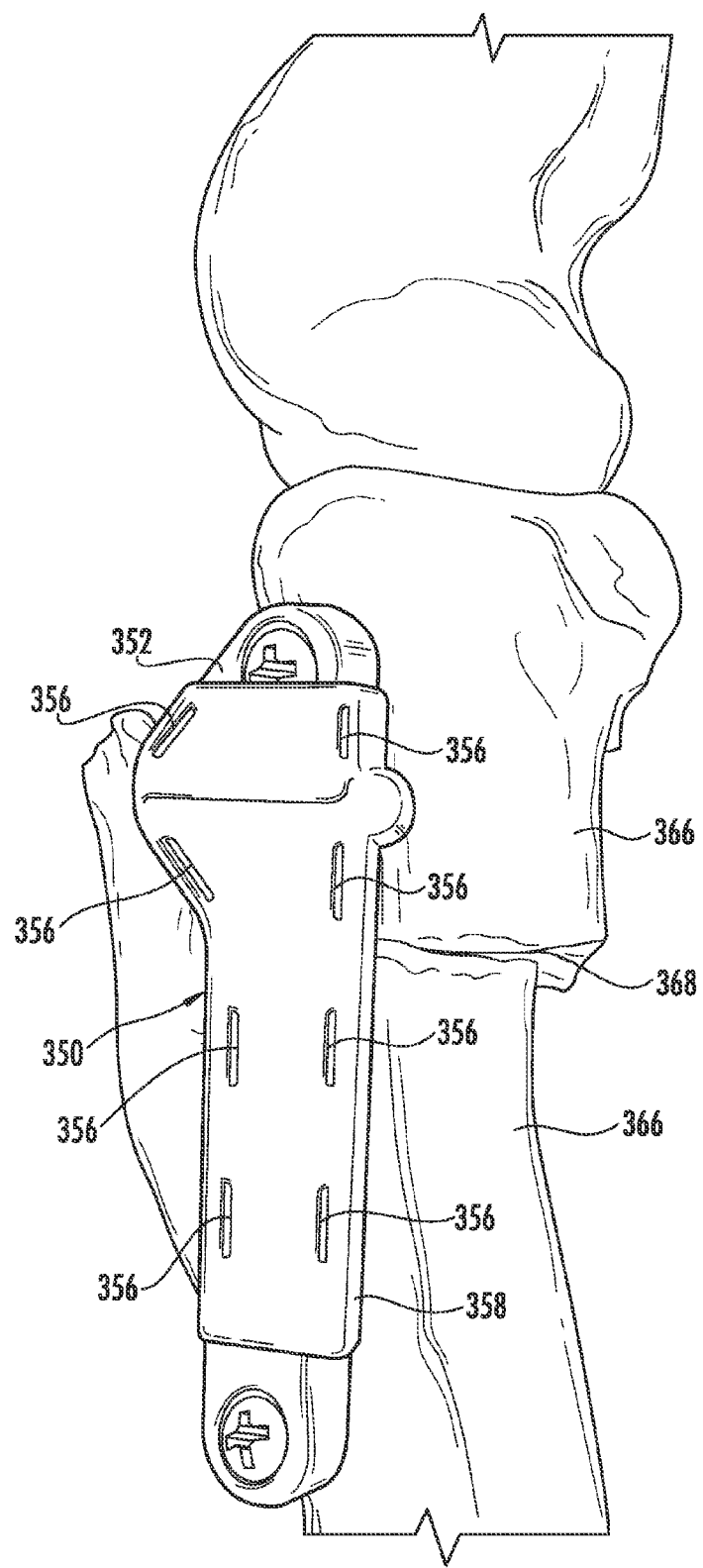
FIG. 74 is a perspective view of the embodiment of the agent-delivery device shown in FIG. 71 adapted to the internal fracture fixation plate secured to a bone fracture.
Figure 75:
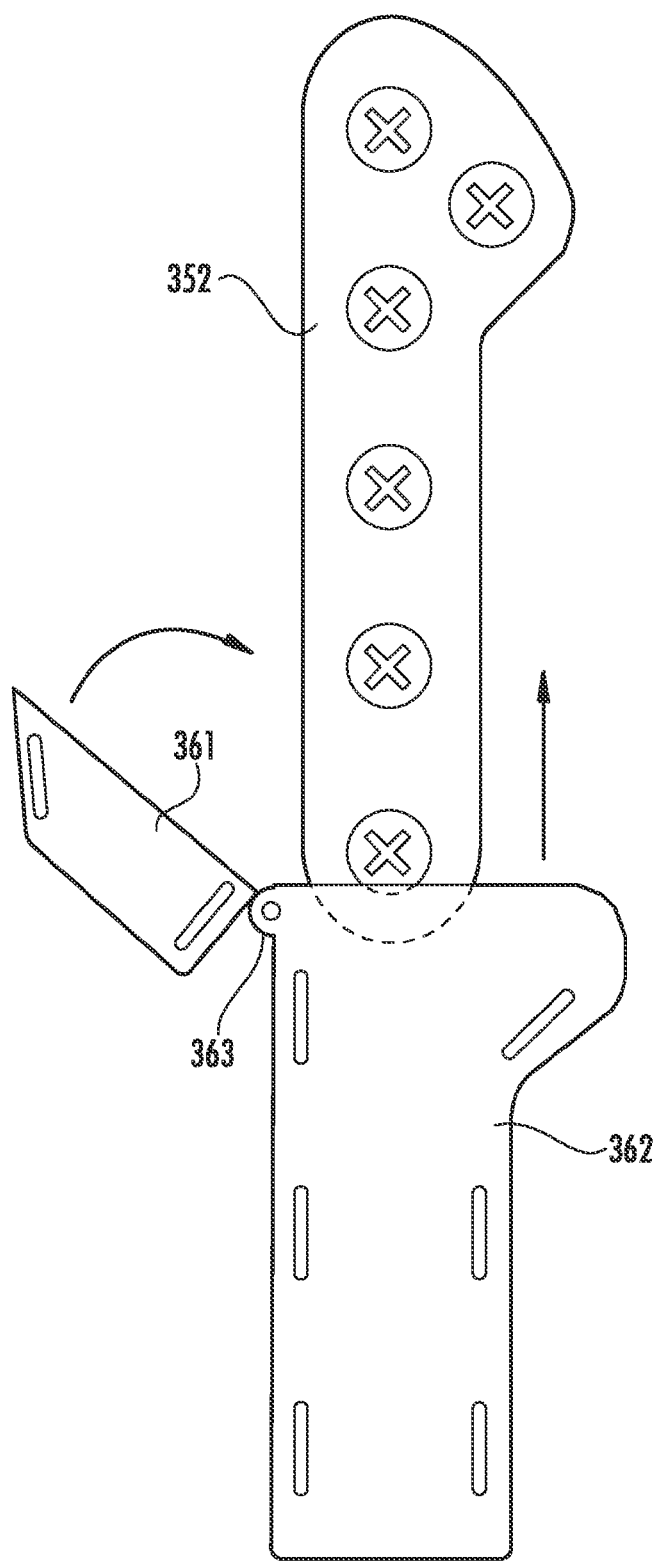
FIG. 75 is an exploded rear elevation view of the agent-delivery device shown in FIG. 71 and the internal fracture fixation plate.
Figure 76:
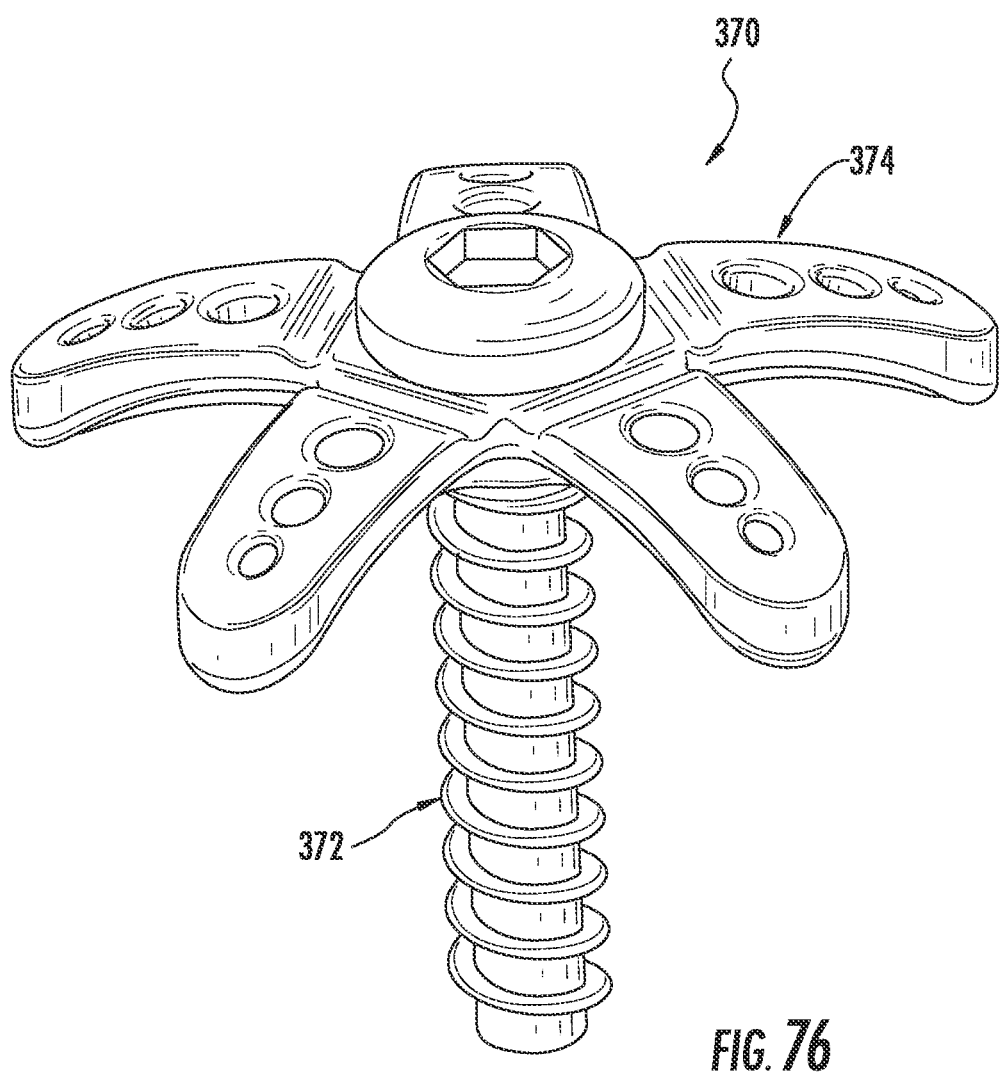
FIG. 76 is a perspective view of another embodiment of an agent-delivery device for use with an anchoring assembly.
Figure 77:
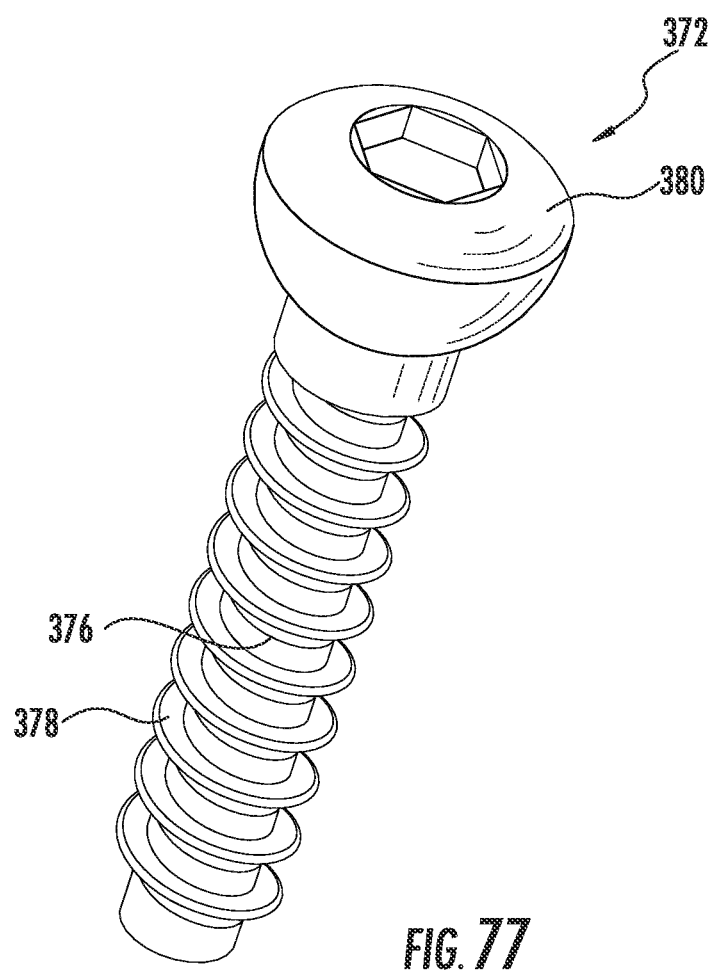
FIG. 77 is a perspective view of an embodiment of an anchor for use with the agent-delivery device shown in FIG. 76.

Referring to FIGS. 73-75, in use, the fracture fixation plate 352 is secured to a bone 366 across a fracture site 368. The agent-delivery device 350 is adapted to the fracture fixation plate 352 by opening the end segment 361 around the hinged connection 363 and sliding the device 350 over the fracture fixation plate 352. Then the end portion 361 is snapped closed in the direction of the arrow (FIG. 75), with the lip 364 extending form the sidewall 368 of the end portion 361 engaging a recess 365 in the sidewall 360 of the major portion 362. The distal ends of the flanges 359 are disposed against the inner surface of the plate 352 for securing the agent-delivery device 350 to the plate 352. The ridges 360 engage the upper surface of the plate 352 for providing space between the inner surface 355 of the agent-delivery device 350 and the fracture fixation plate 352 for disposing a carrier. The openings 356 through the base portion 354 provide pathways so that the therapeutic agent within the carrier is immediately available to the localized area to deliver the desired therapeutic effect.

An embodiment of a delivery device and a retaining assembly for use as an agent-delivery device is shown in FIGS. 76-81, and generally designated at 370. The retaining assembly 370 comprises an anchor element 372 and a carrier element 374. The anchor element 372 is configured for anchoring in bone and can be selected from the group consisting of a screw, staple, nail, hook, pin, or combinations thereof. In one embodiment, the anchor element 372 is a screw (FIG. 77) configured for threading into bone for securing the carrier element 374. The screw 372 includes a shank 376 defining a longitudinal axis and an external thread 378 for screwing into bone, and a screw head 380. The screw head 380 is circular in cross-section and functions as a retaining device by means of which the carrier element is fixed in place. Various bone screws of this kind are known and can, for example, be used to stabilize bones, or fix bones in place relative to each other in that the respective bone screws are screwed into the bones to be fixed.

Figure 78:
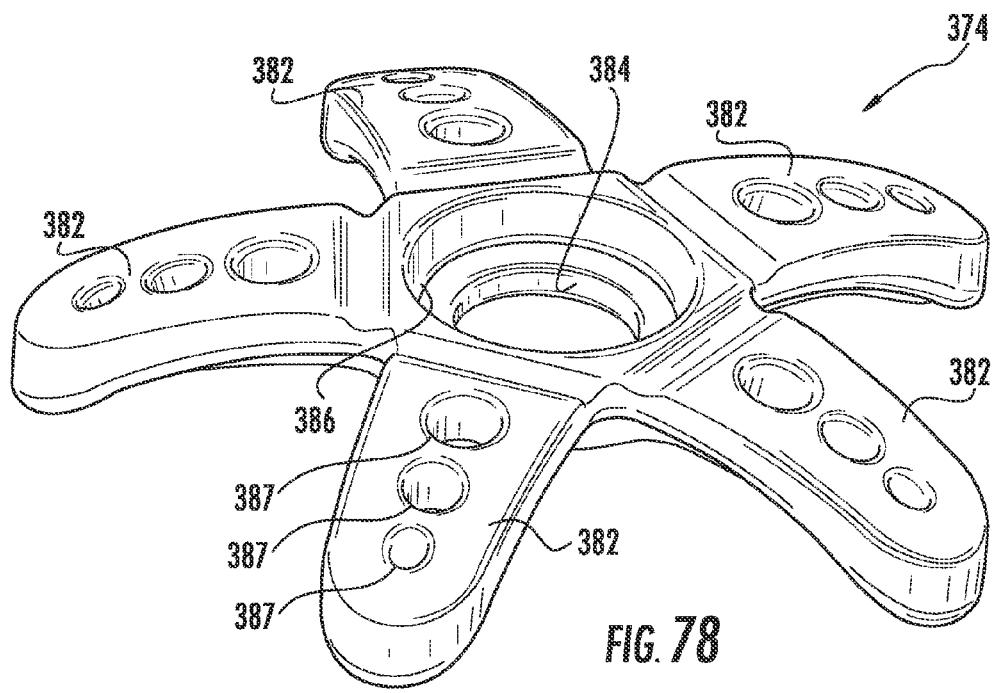
FIG. 78 is a top perspective view of a carrier element for use with agent-delivery device shown in FIG. 76.
Figure 79:
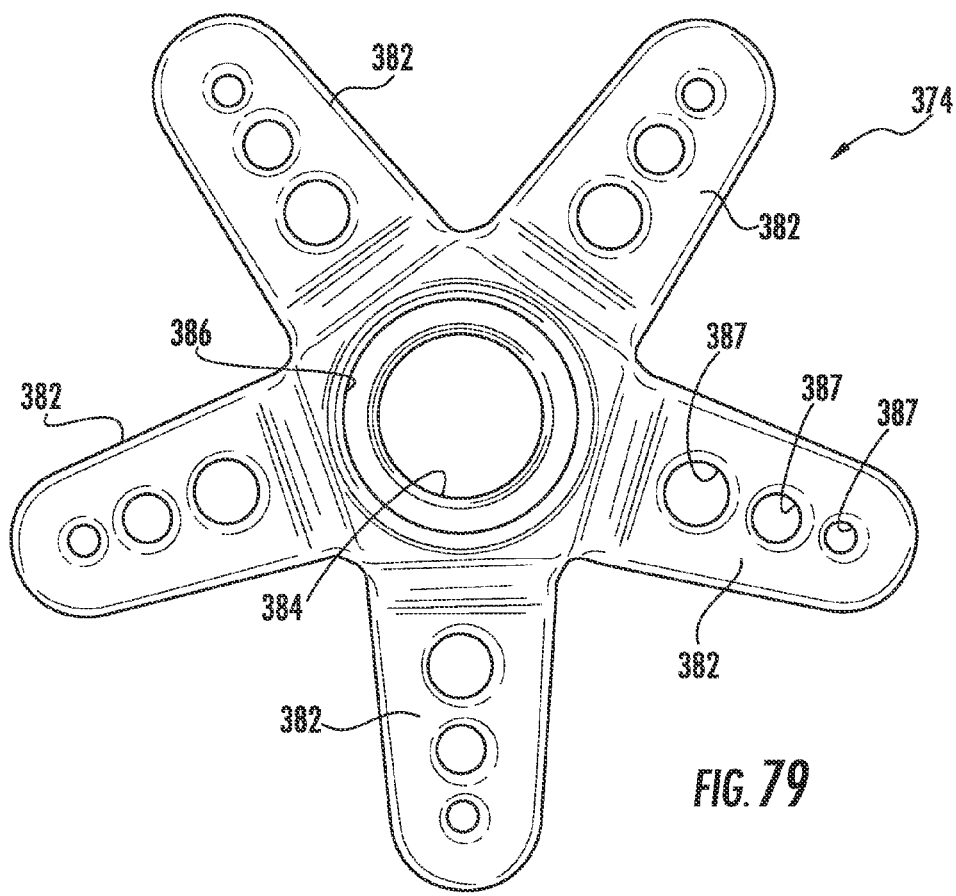
FIG. 79 is a bottom plan view of the embodiment of the agent retaining component of the agent-delivery device shown in FIG. 78.

Referring to FIGS. 78 and 79, the carrier element 374 is generally star-shaped, including five arms 382 extending radially outwardly from the center of the carrier element 374. The carrier element 374 defines a central opening 384. The inside diameter of the opening 384 is larger than the outside diameter of the screw shank 376. The upper surface of the carrier element 374 defines a recess 386 concentric with the central opening 384 for at least partially accommodating the screw head 380. Each arm 382 includes three openings 387, or chambers, in which therapeutic agent may be deposited.

The components of the retaining assembly 370 can be made of materials that are durable and that can be implanted in a body, including titanium, stainless steel, carbon fiber, and the like. In one embodiment, the screw 372 is made of titanium. In another embodiment, the carrier element 374 is made of a biocompatible material, a reabsorbable material or a combination of any of the foregoing materials.

Figure 80:
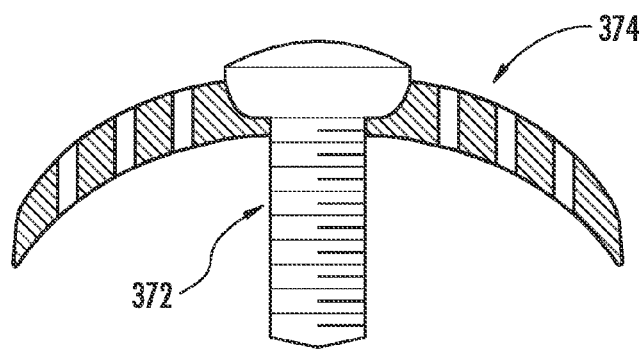
FIG. 80 is a cross-section view of the agent-delivery device shown in FIG. 76.
Figure 81:
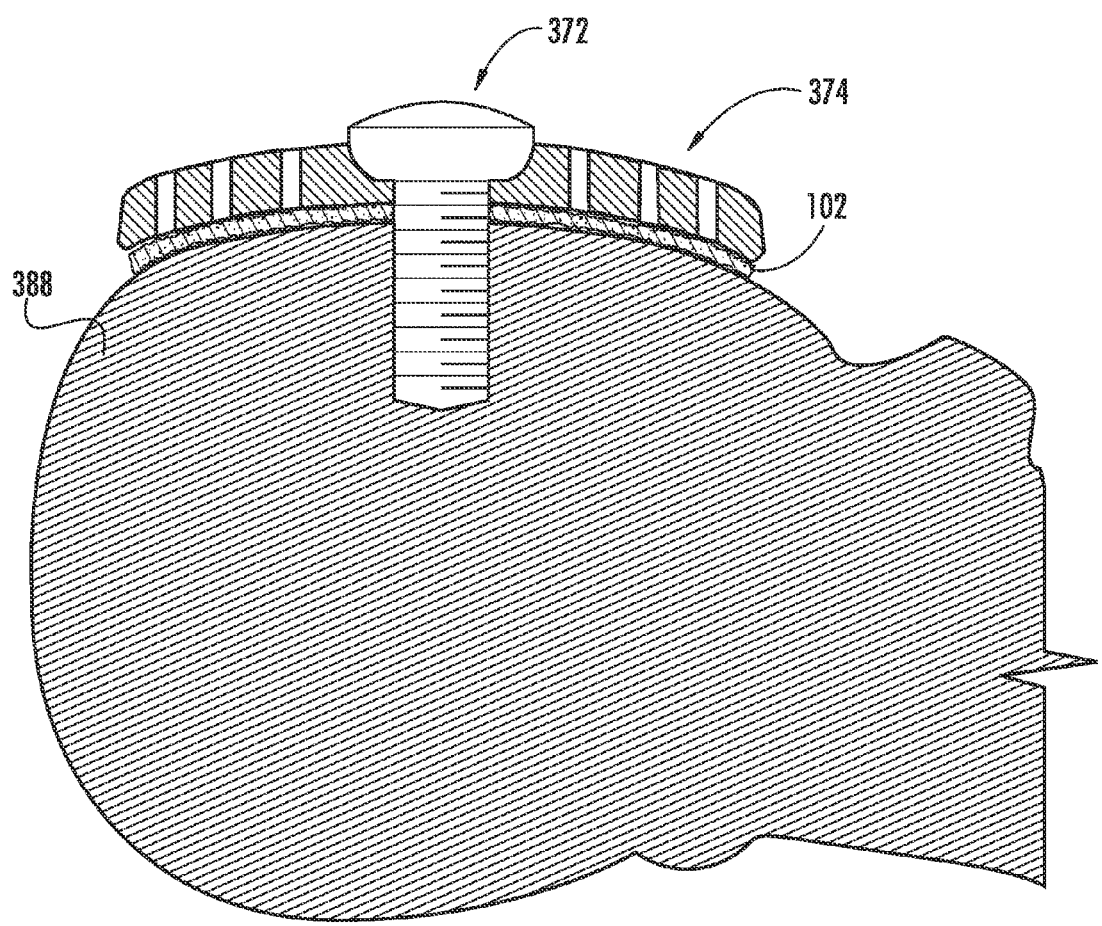
FIG. 81 is a cross-section view of the agent-delivery device as shown in FIG. 80 secured to a bone at a fracture location.
Figure 82:
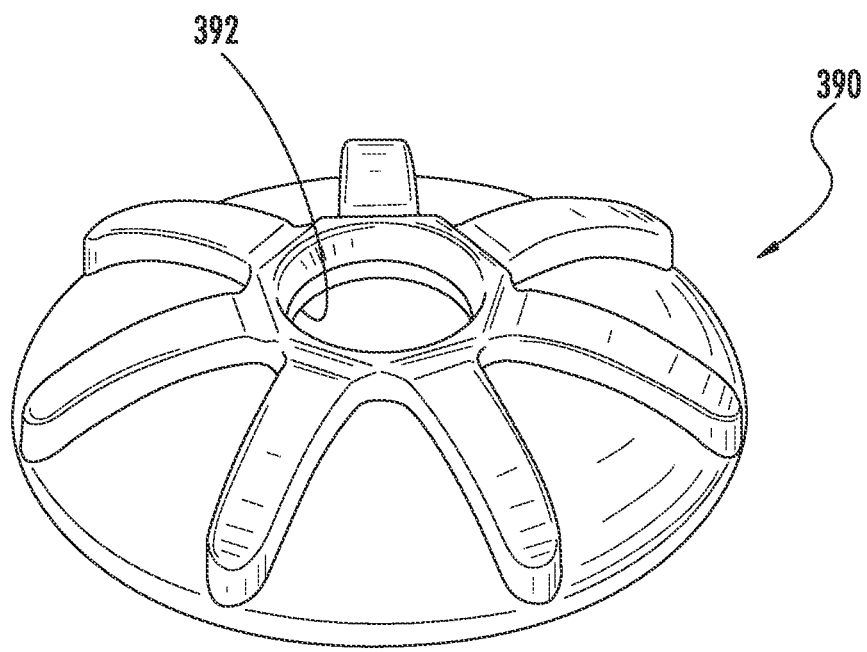
FIG. 82 is a top perspective view of an embodiment of an agent retaining component for use with the embodiment of an anchor shown in FIG. 77.
Figure 83:
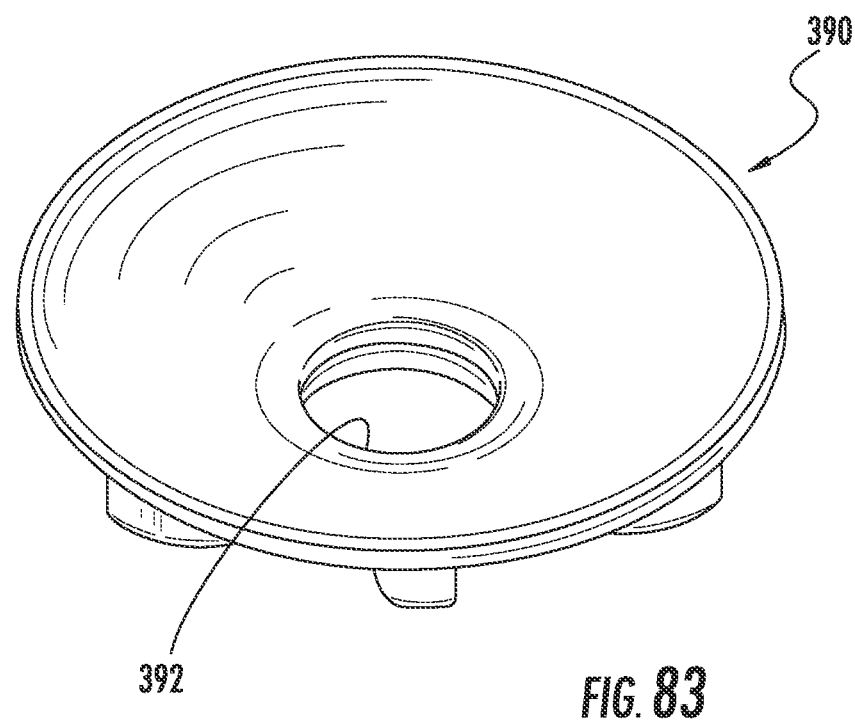
FIG. 83 is a bottom perspective view of the embodiment of an agent retaining component shown in FIG. 82.

The retaining assembly 370 is configured for attachment to bone or another structure in a patient. Referring to FIGS. 80 and 81, in use, the carrier element 374 receives the screw 372 to form the retaining assembly 370. In one implementation, the carrier element 374 is combined with the screw 372 just prior to deployment of the assembly in the patient, and in another implementation, the retaining assembly 370 is pre-assembled. The screw 372 is then threaded into the bone or another structure to secure the carrier element 374 in place. The depth of the recess 386 in the carrier element is sufficient to extend at least partially over the screw head 380. When the screw 372 is seated in the bone the arms 382 are in a position adjacent an area of the outer surface of the bone 388. In one embodiment, the arms 382 flexible and resilient and are configured to define a smaller a smaller diameter when not seated on the bone. When in use, the arms 382 engage the bone and flex outwardly into position over a circumference of an area of the bone in an essentially circular outer contour.

The retaining assembly 370 can be used to support the carrier element against a bony structure, which can include a femur or other bones of the leg (e.g. tibia and fibula), bones of the arm and wrist (e.g. humerus, radius and ulna), and other bones such as the calcaneous, pelvis, spine (vertebrae) and the like. A single retaining assembly 370 may be provided on the bone, or a plurality along a single long bone such as the femur, tibia, humerus, or for more than one bone (i.e. vertebrae). In addition, as shown in FIG. 81, the retaining assembly 370 may be used to capture between the carrier element 374 and the bone a carrier for therapeutic agent, such as a therapeutic agent-eluting sponge 102 or a gel. In this application, the resiliently flexible arms 382 function to provide a biasing force for holding the carrier against the bone.

Two circular embodiments of the carrier element for use with the retaining assembly 370 are shown in FIGS. 82-85, and generally designated at 390 and 400, respectively. Both embodiments of the carrier element 390, 400 comprise cup-shaped members that, when positioned to an adjacent structure, such as bone, define an interior chamber. Each of the carrier elements 390, 400 define a central opening 392 therethrough, and the upper surfaces of the upper portions define a recess 394 concentric with the central opening 392 for receiving the screw head 380. In one embodiment 400 (FIGS. 84 and 85), the carrier element 400 has a plurality of openings 402 formed axially through therethrough. The openings 402 provide communication between the interior chamber and the exterior of the carrier element 400. In use, a carrier for delivering therapeutic agent, such as a therapeutic agent-eluting sponge or a gel (not shown), is placed in the interior cavity defined by the carrier element 390, 400 and the screw 372 is passed through the central opening 392 and threaded into bone for securing the carrier element 390, 400 in place and holding the carrier in the cavity against the bone.

Figure 84:
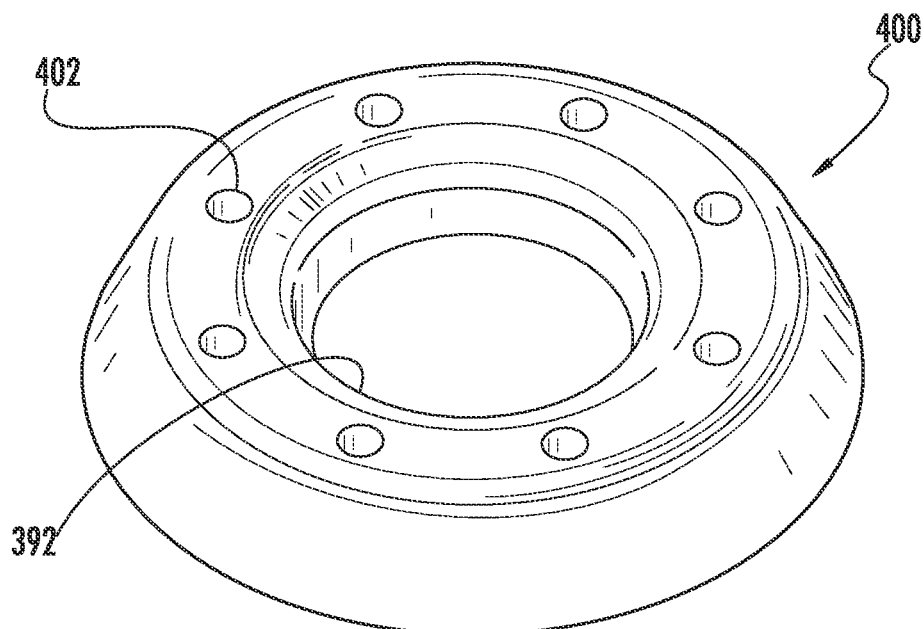
FIG. 84 is a top perspective view of another embodiment of an agent retaining component for use with the embodiment of a screw shown in FIG. 77.
Figure 85:
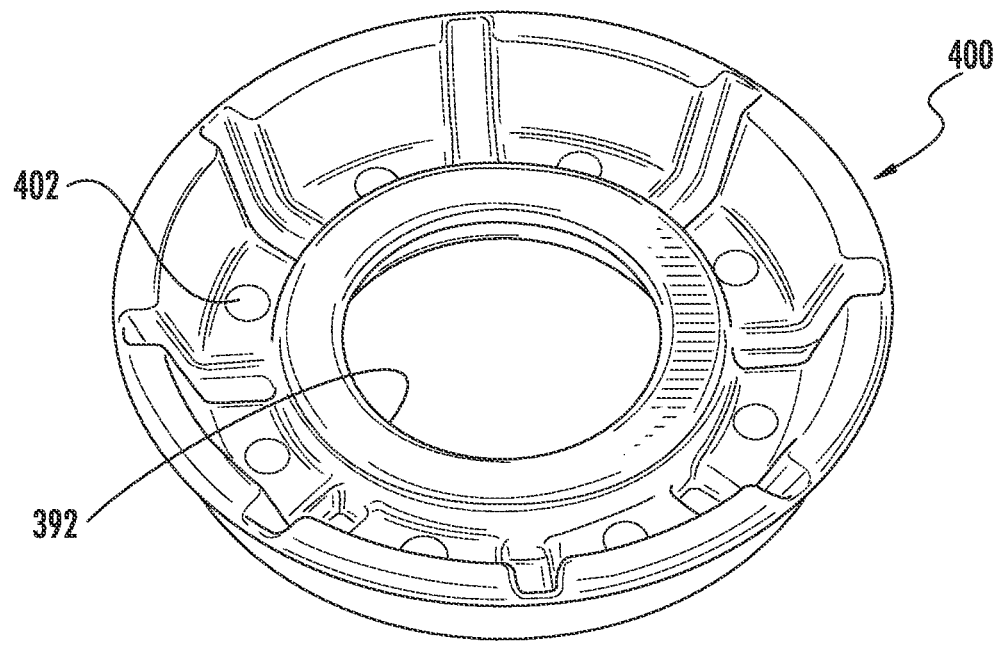
FIG. 85 is a bottom perspective view of the embodiment of an agent retaining component shown in FIG. 84.

It is understood that the retaining assembly 370 is intended for use in a wide variety of sizes. The dimensions of the retaining assembly 370 will vary necessarily with the application in which the device is used. A common feature of the carrier elements 374, 400 shown in FIGS. 78 and 84 is that they include hollow parts to create chambers for delivery of a therapeutic agent. The carrier element 390 shown in FIG. 82 features a simple retaining assembly that holds the carrier in place and, as with other agent-delivery devices, can also deliver its own therapeutic agent and resorb over time.

As described herein, the agent-delivery device allows for a highly localized delivery of one or more therapeutic agents. Without being bound by any particular theory, it is believed that the therapeutic agent associated with the device is released into the body locally proximate to a fracture site. The mechanism of action in a fracture repair is generally the diffusion of the therapeutic agent inward, toward the separated bony regions and the central intramedullary canal. This is the site at which primary or secondary healing of the separated bony surfaces will occur during the fracture repair and bone fusion process. The diffusion process may be facilitated by the holes in the fracture fixation device at the fracture site, for example, those which are not occupied by anchoring screws. In addition to diffusion of the agent toward the fracture healing site, diffusion may also occur outward along the outer periosteal surface of the bone and the outer surface of the fracture callus that forms at the site of fracture repair. Thus, the therapeutic agent is delivered with maximum efficiency to the needed area to enhance bone growth, decrease swelling, minimize pain, fight infection, or any number of other therapeutic achievements.

A plurality of therapeutic agents may be utilized depending on the particular situation or as determined by a healthcare provider. The agent-delivery device may be configured to provide diffusion from specific portions, or surfaces, thereof of one or more therapeutic agents in proximity to one or more specific tissues. For example, an antibiotic may be allowed to diffuse outward into a region around the plate in order to prevent infection at the site of the fracture, while a growth factor may diffuse inwards to accelerate the recruitment of bone precursor cells needed for bone formation and fracture incorporation.

The agent-delivery devices and methods described herein have many advantages, including allowing the surgeon to achieve intra-operative antibiotic resistance, such as in open fractures or other environments of high risk for infection. Alternatively, the agent-delivery device may be easily affixed to an implant at a later time, such as during a debridement and exploration of an infected implant. The local or sustained delivery via the described technology is cost effective. For example, when a fixation device with an agent-delivery device comprising a reservoir is employed, the ability to easily and conveniently affix or replenish the agent-delivery device or the reservoir will likely not delay the operative procedure or increase the operating room time and expense. Cost savings may be achieved via reduced post-operative hospitalization time, reduced likelihood of a revision surgery, for either infection or pseudoarthrosis, and more rapid patient recovery and return to work. Drugs or protein therapies may be conserved by locally delivering a targeted dosage of the therapeutic agent desired. More rapid healing should result in reduced narcotic usage by the patient, and the fixation device with an agent-delivery device may also allow for local delivery of pain-relieving substances into the local environment as opposed to high dosages of systemic narcotics or NSAIDs.

The agent-delivery device is easily adapted to or incorporated into an implant system already in clinical use. Commercially available fracture fixation plates are suitable for use with the agent-delivery device. The device is able to be adapted to affix to a wide range of off-the-shelf medical devices without a requirement to significantly modify the implant for receipt of the local delivery agent. At the same time, agent-delivery devices described herein may be fabricated that adapt to atypical or custom fixation plates with little or no modification to the plate required. The agent-delivery device may be configured to securely adapt to the geometry of the fixation device.

Because the agent-delivery device is entirely separate from the, usually, metallic fixation implant. The two components of a delivery system may be separately constructed, packaged, stored and processed. This allows for separate sterilization of the two systems, should each require differing means of packaging and sterilization. For example, metallic devices are robust and can be sterilized using high doses of radiation or heat and steam. Polymeric materials and therapeutic agents are more fragile and may require low doses of ionizing radiation or gas for sterilization. A therapeutic drug may be processed aseptically rather than undergo a terminal sterilization step. The therapeutic drug, for example a protein growth factor, may be added to the agent-delivery device either in advance of the surgery or at the time of surgery. This will allow the healthcare practitioner to select the agent of interest and dosing required that will be tailored to the patient and the implant environment.

Surgeons may utilize the implants in a standard fashion, including rather vigorous handling of the devices during templating, sizing and implant insertion. In some cases, the implant may be shaped or bent to conform to the body at the time of surgery. The agent-delivery device may be fixed to the implant at the time of surgery or at a later time, such as in the case of revision for infection or non-fusion. In some embodiments, a reservoir containing the therapeutic agent is filled at the time of surgery (or at later follow-up), allowing the surgeon great intra-operative flexibility to select the required antibiotic, growth factor or other agent at the time of surgery.

Although the agent-delivery device has been shown and described in considerable detail with respect to only a few exemplary embodiments thereof, it should be understood by those skilled in the art that we do not intend to limit the invention to the embodiments since various modifications, omissions and additions may be made to the disclosed embodiments without materially departing from the novel teachings and advantages of the invention, particularly in light of the foregoing teachings. For example, the agent-delivery devices described herein are generally applicable to other implant devices in addition to internal fracture fixation devices. Accordingly, we intend to cover all such modifications, omission, additions and equivalents as may be included within the spirit and scope of the invention as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

We claim:

1. An agent-delivery device for delivering an agent to a designated site of action adjacent to a bone in a body of a patient, the agent-delivery device comprising:
    a medical implant including a fracture fixation plate having a lateral dimension and a depth dimension, the fracture fixation plate adapted to be secured to the bone;
    an elongated body member having a longitudinal axis and an inner surface, the body member comprising
        a base portion terminating in longitudinal edges, a distance between the longitudinal edges of the base portion being substantially equal to the lateral dimension of the fracture fixation plate, and
        legs extending from the longitudinal edges of the base portion, the legs terminating in longitudinal edges, the base portion and legs defining an open longitudinal channel for receiving the fracture fixation plate;
    a projection on an inner surface of the base portion, wherein a distance the projection extends from the inner surface of the base portion is less than a distance from the longitudinal edges of the base portion to the longitudinal edges of the legs, the distance from the longitudinal edges of the base portion to the longitudinal edges of the legs being substantially equal to the distance the projection extends from the inner surface of the base portion plus the depth dimension of the fracture fixation plate; and
    an agent-delivery medium associated with the body member, the agent-delivery medium including a therapeutic agent for treating the body of the patient, and a carrier for the therapeutic agent,
    wherein the body member is adapted to be secured to the fracture fixation plate such that the projection operatively engages the fracture fixation plate for spacing the inner surface of the base portion from the fracture fixation plate forming a channel between the inner surface of the base portion and the fracture fixation plate for accommodating the carrier, and wherein the agent-delivery medium is configured to release the therapeutic agent after implantation in the body of the patient.

2. An agent-delivery device as recited in claim 1, wherein the projection extends longitudinally along the body member.

3. An agent-delivery device as recited in claim 2, wherein the projection extends along the longitudinal axis of the body member.

4. An agent-delivery device as recited in claim 2, wherein the body member has a first end and a second end, and the projection extends from the first end to the second end.

5. An agent-delivery device as recited in claim 4, wherein the projection extends along the longitudinal axis of the body member.

6. An agent-delivery device as recited in claim 1, wherein the carrier is a sponge.

7. An agent-delivery device as recited in claim 1, wherein the carrier is a gel.

8. An agent-delivery device as recited in claim 1, wherein the projection extends transversely to the longitudinal axis of the body member.

9. An agent-delivery device as recited in claim 1, wherein the body member has at least one passage opening into the inner surface of the body member.

* * * * *